US008742152B2

(12) United States Patent
Yaghi et al.

(10) Patent No.: US 8,742,152 B2
(45) Date of Patent: Jun. 3, 2014

(54) PREPARATION OF METAL-CATECHOLATE FRAMEWORKS

(75) Inventors: Omar M. Yaghi, Los Angeles, CA (US);
Felipe Gandara-Barragan, Los Angles, CA (US); Zheng Lu, Knoxville, TN (US); Shun Wan, Santa Monica, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 13/363,792

(22) Filed: Feb. 1, 2012

(65) Prior Publication Data

US 2012/0215015 A1  Aug. 23, 2012

Related U.S. Application Data

(60) Provisional application No. 61/439,748, filed on Feb. 4, 2011.

(51) Int. Cl.
*C07F 1/08* (2006.01)
*C07F 1/10* (2006.01)

(52) U.S. Cl.
USPC .......................................... 556/113; 556/110

(58) Field of Classification Search
USPC .................................................. 556/110, 113
See application file for complete search history.

(56) References Cited

U.S. PATENT DOCUMENTS

| | | | |
|---|---|---|---|
| 2,684,967 A | 7/1954 | Berg | |
| 4,532,225 A | 7/1985 | Tsao et al. | |
| 5,064,804 A | 11/1991 | Soo et al. | |
| 5,160,500 A | 11/1992 | Chu et al. | |
| 5,208,335 A | 5/1993 | Ramprasad et al. | |
| 5,648,508 A | 7/1997 | Yaghi et al. | |
| 5,733,505 A | 3/1998 | Goldstein et al. | |
| 6,479,447 B2 | 11/2002 | Bijl et al. | |
| 6,501,000 B1 | 12/2002 | Stibrany et al. | |
| 6,617,467 B1 | 9/2003 | Mueller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,637,983 B1 | 12/2009 | Liu et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 | 10/2010 | Mueller et al. | |
| 2003/0004364 A1 | 1/2003 | Yaghi et al. | |
| 2003/0078311 A1 | 4/2003 | Mueller et al. | |
| 2003/0148165 A1 | 8/2003 | Mueller et al. | |
| 2003/0222023 A1 | 12/2003 | Mueller et al. | |
| 2004/0081611 A1 | 4/2004 | Mueller et al. | |
| 2004/0225134 A1 | 11/2004 | Yaghi et al. | |
| 2004/0249189 A1 | 12/2004 | Mueller et al. | |
| 2004/0265670 A1 | 12/2004 | Mueller et al. | |
| 2005/0004404 A1 | 1/2005 | Mueller et al. | |
| 2005/0014371 A1 | 1/2005 | Tsapatsis | |
| 2005/0124819 A1 | 6/2005 | Yaghi et al. | |
| 2005/0154222 A1 | 7/2005 | Mueller et al. | |
| 2005/0192175 A1 | 9/2005 | Yaghi et al. | |
| 2006/0057057 A1 | 3/2006 | Mueller et al. | |
| 2006/0135824 A1 | 6/2006 | Mueller et al. | |
| 2006/0154807 A1 | 7/2006 | Yaghi et al. | |
| 2006/0185388 A1 | 8/2006 | Mueller et al. | |
| 2006/0252641 A1 | 11/2006 | Yaghi et al. | |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |
| 2007/0202038 A1 | 8/2007 | Yaghi et al. | |
| 2007/0248575 A1 | 10/2007 | Connor et al. | |
| 2008/0017036 A1 | 1/2008 | Schultink et al. | |
| 2008/0184883 A1 | 8/2008 | Zhou et al. | |
| 2009/0155588 A1 | 6/2009 | Hesse et al. | |
| 2010/0132549 A1 | 6/2010 | Yaghi et al. | |
| 2010/0143693 A1 | 6/2010 | Yaghi et al. | |
| 2010/0186588 A1 | 7/2010 | Yaghi et al. | |
| 2010/0286022 A1 | 11/2010 | Yaghi et al. | |
| 2011/0137025 A1 | 6/2011 | Yaghi et al. | |

FOREIGN PATENT DOCUMENTS

| | | |
|---|---|---|
| DE | 102005023856 A1 | 11/2006 |
| DE | 102005054523 A1 | 5/2007 |
| EP | 1674555 A1 | 6/2006 |
| KR | 10-2010-0055350 | 5/2010 |
| WO | 2004101575 A2 | 11/2004 |

(Continued)

OTHER PUBLICATIONS

Barman et al., "Incorporation of active metal sites in MOFs via in situ generated ligand deficient metal-linker complexes" Chem. Commun. 47:11882-11884 (Oct. 11, 2011.

Burrows et al., "Post-Synthetic Modivication fo Tagged Metal-Organic Frameworks," Angew. Chem Int'l., 2008, pp. 8482-8486, vol. 47.

Chen et al., "Noncovalently Netted, Photoconductive Sheets with Extremely High Carrier Mobility and Conduction Anisotropy from Triphenylene-Fused Meetal Trigon Conjugates," In. J. Am. Chem. Soc. 131:7287-7297 (2009).

Choi et al., "Reversible Interpenetration in a Metal-Organic Framework Triggered by Ligand Removal and Addition," Angew. Chem. Int. Ed. 51:8791 -8795 (2012).

Coskun et al., "Metal-Organic Frameworks Incorporating Copper-Complexed Rotaxanes," Angew. Chem. Int. Ed., 51:2160-2163 (2012).

(Continued)

*Primary Examiner* — Golam M M Shameem
(74) *Attorney, Agent, or Firm* — Joseph R. Baker, Jr.; Gavrilovich, Dodd & Lindsey LLP

(57) ABSTRACT

The disclosure provides for metal catecholate frameworks, and methods of use thereof, including gas separation, gas storage, catalysis, tunable conductors, supercapacitors, and sensors.

11 Claims, 16 Drawing Sheets

(56) References Cited

FOREIGN PATENT DOCUMENTS

| | | | |
|---|---|---|---|
| WO | 2006047423 A2 | 5/2006 | |
| WO | 2006072573 A2 | 7/2006 | |
| WO | 2006116340 A1 | 11/2006 | |
| WO | 2007101241 A2 | 9/2007 | |
| WO | 2007111739 A2 | 10/2007 | |
| WO | 2008091976 A1 | 7/2008 | |
| WO | 2008138989 A1 | 11/2008 | |
| WO | 2008140788 A1 | 11/2008 | |
| WO | 2009020745 A9 | 2/2009 | |
| WO | 2009042802 A1 | 4/2009 | |
| WO | 2009056184 A1 | 5/2009 | |
| WO | 2009149381 A3 | 12/2009 | |
| WO | 2010056092 A9 | 5/2010 | |
| WO | 2010078337 A1 | 7/2010 | |
| WO | 2010080618 A1 | 7/2010 | |
| WO | 2010083418 A1 | 7/2010 | |
| WO | 2010088629 A1 | 8/2010 | |
| WO | 2010090683 A1 | 8/2010 | |
| WO | 2010148276 A3 | 12/2010 | |
| WO | 2010148296 A3 | 12/2010 | |
| WO | 2010148374 A3 | 12/2010 | |
| WO | 2011014503 A1 | 2/2011 | |
| WO | 2011038208 A2 | 3/2011 | |
| WO | 2011146155 A9 | 11/2011 | |
| WO | 2012012495 A3 | 1/2012 | |
| WO | 2012082213 A2 | 6/2012 | |
| WO | 2012100224 A3 | 7/2012 | |
| WO | 2012106451 A2 | 8/2012 | |

OTHER PUBLICATIONS

Cui et al., "IIn Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).

Demessence, A et al., "Strong CO2 Bnding in a Water-Stable, Triazolate-Bridged Metal-Organic Framework Functionalized with Ethylenediamine," J. Am. Chem. Soc. 131:8784-8786 (2009).

Deng et al., "Large-Pore Apertures in a Series of Metal-Organic Frameworks," Science 336:1018-1023 (May 25, 2012).

Li et al., "Synthesis and Structural Characterization of a New 3D Lead Coordination Polymer with a Tetrazole-1-acetate Ligand," Chinese J. Struct. Chem. 30(7):1049-1053 (2011).

Galli et al., "Adsorption of Harmful Organic Vapors by Flexible Hydrophobic Bis-pyrazolate Based MOFs," Chem. Mater. 22(5):1664-1672 (2010).

Natarajan et al., "Non-carboxylate based metal-organic frameworks (MOFs) and related aspects," Current Opinion in Solid State and Materials Science 13(3-4):46-53 (2009).

Nickitas-Etienne, Athina, International Preliminary Report on Patentability for PCT/US2009/068731. Date of Issuance of the Report: Jun. 21, 2011.

Peterson et al., "Ammonia Vapor Removal by Cu3(BTC)2 and Its Characterization by MAS NMR," J. Phys. Chem. C. 113(32):13906-13917 (2009).

Seo et al., "A homochiral metal-organic porous material for enantioselective separation and catalysis," Nature 404:982-986 (2000).

Song et al., "Hydrothermal Synthesis and Structural Characterization of Three-dimensional Metal-organic Framework [Zn3(C2H2N3)2(C7H5O2)4]," Chem. Res. Chinese Universities 25(1):1-4 (2009).

Vitillo et al., "Role of Exposed Metal Sites in Hydrogen Storage in MOFs," J. Am. Chem. Soc. 130(26):8386-8396 (2008).

Wang et al., "Postsynthetic Covalent Modification of a Neutral Metal-Organic Framework," J. Am. Chem. Soc. 129 (41):12368-12369 (2007).

Wang et al., "Tandem Modification of Metal-Organic Frameworks by a Postsynthetic Approach," Angew. Chem. Int. 47:4699-4702 (2008).

Yaghi, Omar., "Porous Crystals for Carbon Dioxide Storage," slide presentation at the Fifth Annual Conference on Carbon Capture & Sequestration, US Department of Energy on May 10,2006 http://www.netl.doe.gov/publications/proceedings/06/carbon-seq/Tech%20Session%20193.pdf.

Fracaroli et al., "Isomers of Metal-Organic Complex Arrays," Inorg. Chem. 51: 6437-6439 (Jun. 5, 2012).

Furukawa et al., "Isoreticular Expansion of MetalOrganic Frameworks with Triangular and Square Building Units and the Lowest Calculated Density for Porous Crystals," Inorg. Chem. 50:9147-9152 (2011).

Gadzikwa, T. et al., "Selective Bifunctional Modification of a Non-catenated Metal-Organic Framework Material via Click Chemistry," J. Am. Chem. Soc. 131:13613-13615 (2009).

Gandara et al., "Porous, Conductive Metal-Triazolates and Their Structural Elucidation by the Charge-Flipping Method," Chem. Eur. J. 18:10595-10601 (2012).

Gassensmith et al., "Strong and Reversible Binding of Carbon Dioxide in a Green Metal-Organic Framework," J. Am. Chem. Soc. 133:15312-15315 (Aug. 30, 2011).

Goto, Y et al., "Clickable Metal-Organic Framework," J. Am. Chem. Soc. 130:14354-14355 (2008).

Hmadeh et al., "New Porous Crystals of Extended Metal-Catecholates," J. Chem. Mater. 24:3511-3513 (Aug. 28, 2012).

Koh et al., "A Crystalline Mesoporous Coordination Copolymer with High Microporosity," Angew Chem Int'l, 2008, pp. 677-680, vol. 47.

Li, Y et al., "Hydrogen Storage in Metal-Organic and Covalent-Organic Frameworks by Spillover," AIChe Journal 54 (1):269-279 (2008).

McKeown et al., "Phthalocyanine-Based Nanoporous Network Polymers," Chem. Comm. 23:2780-2781 (Oct. 31, 2002).

McKeown et al., "Porphyrin-Based Nanoporous Network Polymers," Chem. Comm. 23:2782-2783 (Oct. 31, 2002).

Morris et al., "Framework mobility in the metal-organic framework crystal IRMOF-3: Evidence for aromatic ring and amine rotation," Journal of Molecular Structure 1004:94-101 (2011).

Morris et al., "NMR and X-ray Study Revealing the Rigidity of Zeolitic Imidazolate Frameworks," J. Phys. Chem. 116 (24):13307-13312 (Jun. 1, 2012).

Morris et al., "Synthesis, Structure, and Metalation of Two New Highly Porous Zirconium Metal-Organic Frameworks," Inorg. Chem. 51:6443-6445 (Jun. 7, 2012).

O'Keeffe et al., "Deconstructing the Crystal Structures of Metal-Organic Frameworks and Related Materials into Their Underlying Nets," Chem. Rev. 112(2):675-702 (Feb. 8, 2012).

Park, H. et al., "Synthesis, Structure Determination and Hydrogen Sorption Studies of New Metal-Organic Frameworks Using Triazole and Naphthalenedicarboxylic Acid," Chem. Natur. 19:1302-1308 (2007).

Queen et al., "Site-Specific CO2 Adsorption and Zero Thermal Expansion in an Anisotropic Pore Network," J. Phys. Chem. C, 115:24915-24919 (Nov. 8, 2011).

Spitler et al., "Lewis Acid Catalyzed Formation of Two-Dimensional Phthalocyanine Covalent Organic Framewokrs." Nature Chem. 2:672-677 (Jun. 20, 2010).

Tilford et al., "Facile Synthesis of a Highly Crystalline, Covalently Porous Boronate Network," 18(22):5296-5301 (Oct. 11, 2006).

Tranchemontagne et al., "Hydrogen Storage in New Metal-Organic Frameworks," J. Phys. Chem. C 116 (24):13143-13151 (May 24, 2012).

Wan et al, "A Belt-Shaped, Blue Luminescent, and Semiconducting Covalent Organic Framework." Angew. Chem. Int. Ed. 47:8826-8830 (2008).

Wan et al., "Covalent Organic Frameworks with High Charge Carrier Mobility," Chem. Mater. 23:4094-4097 (Aug. 22, 2011).

Yang, E. et al. "Four NovelThree-Dimensional Triazole-Based Zind(II) Metal-Organic Frameworks Controlled by the Spacers of Dicarboxylate Ligands: Hydrotermal Synthesis, Crystal Strucutre, and Luminescence Properties," Cryst. Growth & Design. 7:2009-2015 (2007).

Zhang, J. et al., "Exceptional Framework Flexibility and Sorption Behavior of a Multifunctional Porous Cuprous Triazolate Framework," J. Am. Chem. Soc. 130:6010-6017 (2008).

(56) References Cited

OTHER PUBLICATIONS

Zhou, X et al., "Hydrothermal Syntheses and Structures of Three Novel Coordination Polymers Assembled from 1,2,3-Triazolate Ligands," CrystEngComm. 11:1964-1970 (2009).
Zhou et al., "Introduction to Metal-Organic Frameworks," Chemical Reviews 112:673-674 (Jan. 26, 2012).
Zhu, A et al., "Isomeric Zinc(II) Triazolate Frameworks with 3-Connected Networks: Syntheses, Structures, and Sorption Properties," Inorg. Chem. 48:3882-3889 (2009).
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Uribe-Romo et al., "A Crystalline Imine-Linked 3-D Porous Covalent Organic Framework," J. Am. Chem. Soc. 131:4570-4571 (2009).
Uribe-Romo et al., "Crystalline Covalent Organic Frameworks with Hydrazone Linkages," J. Am. Chem. Soc. 133: 11478-11481 (2011).
Vairaprakash et al., "Synthesis of Metal-Organic Complex Arrays," J. Am. Chem. Soc. 133:759-761 (2011).
Valente et al., "Metal-organic Frameworks with Designed Chiral Recognition Sites," Chem. Commun. 46: 4911-4913 (2010).
Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)," J. Am. Chem. Soc.124 (18):4942-4943 (2002).
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Colossal Cages in Zeolitic Imidazolate Frameworks as Selective Carbon Dioxide Reservoirs," Nature 453:207-211 (2008).
Wong-Foy, AG et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'- Bipyridine)CI," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks,"Mater. Res. Soc. Symp. Proc., 1995, 371, 15.
Yaghi et al., "Hydrothermal Synthesis of a Metal-Organic Framework Containing Large Rectangular Channels," J. Am. Chem. Soc., 1995, 117, 10401-10402.
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "T-Shaped Molecular Building Units in the Porous Structure of Ag(4,4'-bpy) NO3," J. Am. Chem. Soc., 1996, 118, 295-296.
Yaghi et al., "Construction of Porous Solids from Hydrogen-Bonded Metal Complexes of 1,3,5-Benzenetricarboxylic Acid," J. Am. Chem. Soc., 1996, 118, 9096-9101.
Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.
Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(CI04)2•1.5 (4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthesis and Structure of a Metal-Organic Solid Having the Cadmium (II) Sulfate Net," Mater. Res. Soc. Symp. Proc. 453:127 , (1997).
Yaghi et al., "Designing Microporosity in Coordination Solids," Modular Chemistry, J. Michl, Ed., Kluwer: Boston, p. 663 (1997).
Yaghi et al., "Synthetic Strategies, Structure Patterns, and Emerging Properties in the Chemistry of Modular Porous Solids," Acc. Chem. Res. 31:474-484 (1998).
Yaghi et al., "Transformation of Germanium Dioxide to 4-Connected Porous Germanate Net," J. Am. Chem. Soc., 20:10569-10570 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi et al., "Metal-Organic Frameworks: A Tale of Two Entanglements," Nature materials 6:92-93 (2007).
Yaghi et al., "Reticular Chemistry and Metal-Organic Frameworks for Clean Energy," MRS Bulletin 34:682-690 (2009).
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Young, Jung Doo. International Search Report for PCT/US2010/050170. Date of Mailing: Jun. 8, 2011.
Zhang et al., "Docking in Metal-Organic Frameworks," Science 325:855-859 (2009).

(56) References Cited

OTHER PUBLICATIONS

Zhao et al., "Rigid-Strut-Containing Crown Ethers and [2]Catenanes for Incorporation into Metal-Organic Frameworks," Chem. Eur. J. 15:13356-13380 (2009).

Zhofu et al., "A Nearly Planar Water Sheet Sandwiched between Strontium-Imidazolium Carboxylate Coordination Polymers," Inorg. Chem. 44:5200-5202 (2005).

Ferragut et al., "Positronium Formation in Porous Materials for Antihydrogen Production,"J. Phys. Conf. Ser. 225:1-8 (2010).

Furukawa et al., "Crystal Structure, Dissolution, and Deposition of a 5 nm Functionalized Metal-Organic Great Rhombicuboctahedron," J. Am. Chem. Soc. 128:8398-8399 (2006).

Furkawa et al., "Independent verification of the saturation hydrogen uptake in MOF-177 and establishment of a benchmark for hydrogen adsorption in metal-organic frameworks," J. Mater. Chem. 17:3197-3204 (2007).

Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).

Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).

Furukawa et al., "Ultra-High Porosity in Metal-Organic Frameworks," Science 239:424-428 (2010).

Glover et al., "MOF-74 building unit has a direct impact on toxic gas adsorption," J. Chem. Eng. Sci. 66:163-170 (2011).

Gould et al., "The Amphidynamic Character of Crystalline MOF-5: Rotational Dynamics in a Free-Volume Environment," J. Am. Chem. Soc. 130:3246-3247 (2008).

Goebel, Matthias, Supplemental European Search Report and Written Opinion for EP08826913. Date of Completion of Search and Written Opinion: Nov. 10, 2010.

Goebel, Matthias, Supplemental European Search Report and Written Opinion for EP08754337. Date of Completion of Search and Written Opinion: Dec. 3, 2010.

Gonzalez-Arellano et al., "Homogeneous and heterogeneous Au(III) Schiff base-complexes as selective and general catalysts for self-coupling of aryl boronic acids," Chem. Comm. 15:1990-1992 (2005).

Grzesiak et al., "Polymer-Induced Heteronucleation for the Discovery of New Extended Solids," Angew. Chem. Int. Ed. 45:2553-2556 (2006).

Halper et al., "Topological Control in Heterometallic Metal-Organic Frameworks by Anion Templating and Metalloligand Design," J. Am. Chem. Soc. 128:15255-15268 (2006).

Han, SS et al., "Improved designs of metal-organic frameworks for hydrogen storage" Angew. Chem. Int. Ed. 2007, 46, pp. 6289-6292.

Han et al., "Covalent Organic Frameworks as Exceptional Hydrogen Storage Materials," J. Am. Chem. Soc. 130: 11580-11581 (2008).

Hayashi et al., "Zeolite A Imidazolate Frameworks," Nature Materials 6:501-506 (2007).

Hexiang et al., "Multiple Functional Groups of Varying Rations in Metal-Organic Frameworks," Science 327 (5967):846-850 (2010).

Holler et al., "The first dinitrile frameworks of the rare earth elements: [LnCI3(1,4-Ph(CN)2] and [Ln2CI6(1,4Ph(CN) 2], Ln = Sm, Gd, Tb, Y; Access to novel metal-organic frameworks by solvent free synthesis in molten 1,4-benodinitrile," Inorganic Chemistry 47(21): 10141-9 (2008).

Honda, Masashi, International Preliminary Report on Patentability for PCT/US2008/051859. Date of Issuance of the Report: Jul. 28, 2009.

Howe, Patrick. International Search Report and Written Opinion for PCT/US2010/022777. Date of Mailing: Jun. 7, 2010.

Huang et al., "Thermal Conductivity of Metal-Organic Framework 5 (MOF-5): Part II. Measurement," Int. J. Heat Mass Transfer 50:405-411 (2007).

Hunt et al., "Reticular Synthesis of Covalent Organic Borosilicate Frameworks," J. Am. Chem. Soc. 130: 11872-11873 (2008).

Isaeva et al., "Metal-organic frameworks-new materials for hydrogen storage," Russian Journal of General Chemistry 77(4):721-739 (2007).

Jeong et al., "Asymmetric Catalytic Reactions by NbO-Type Chiral Metal-Organic Frameworks," Chem. Sci. 2:877-882 (2011).

Kaderi et al., "Designed Synthesis of 3D Covalent Organic Frameworks," Science 316:268-272 (2007).

Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).

Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).

Kim, Su Mi, International Search Report and Written Opinion for PCT/US2009/068731. Date of Mailing: Aug. 19, 2010.

Kim, Su Mi, International Search Report and Written Opinion, Date of Mailing: Feb. 24, 2010, International Application No. PCT/US09/46463.

Kim, Su Mi. International Search Report for PCT/US2010/039154. Date of Mailing: Feb. 23, 2011.

Kirai et al., "Homocoupling of arylboronic acids catalyzed by 1,10-phenanthroline—ligated copper complexes in air," European Journal of Organic Chemistry 12:1864-1867 (2009).

Klaes, Daphne. International Search Report and Written Opinion for PCT/US2010/021201. Date of Mailing: Apr. 27, 2010.

Koza et al., "An efficient High Yielding Approach for the Homocoupling of Aryl Boronic Acids," Synthesis 15:2183-2186 (2002).

Kyoungmoo et al., "A Crystalline Mesoporous Coordination Copolymer with High Microporosity," Angew. Chem. Int. Ed. 47(4):689-92 (2008).

Lee, Ji Min. International Search Report for PCT/US2010/039284. Date of Mailing: Feb. 22, 2011.

Li et al., "Coordinatively Unsaturated Metal Centers in the Extended Porous Framewokr of Zn3(BDC)3-6CH3OH (BDC= 1,4-Benzenedicarboxylate)," J. Am. Chem. Soc. 2186-2187 (1998).

Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).

Li et al., "Porous Germanates: Synthesis, Structure and Inclusion Properties of Ge7O14.5F2-[(CH3)2NH2]3(H2O) O.86," J. Am. Chem. Soc. 120:8567-8568 (1998).

Li et al., "Transformation of Germanium Dioxide to 4-Connected Porous Germanate Net," J. Am. Chem. Soc. 10569-10570 (1998).

Li et al., "An Open-Framework Germanate with Polycubane-Like Topology," Angew. Chem. INt. Ed., 38:653-655 (1999).

Li et al., "Supertetrahedral Sulfide Crystals with Giant Cavities and Channels," Science 283:1145-1147 (1999).

Li et al., "Non-interpenetrating Indium Sulfide with a Supertetrahedral Cristobalite Famework," J. Am. Chem. Soc. 121:6096-6097 (1999).

Li et al., "Design and Synthesis of an Exceptionally Stable and Highly Porous Metal-Organic Framework," Science 402:276-279 (1999); Featured in (1) Chemical and Engineering News (Nov. 22, 19999) and (2) Science News (Nov. 20, 1999).

Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).

Li et al., "20 A [Cd4In16S35]14- Supertetrahedral T4 Clusters as Building Units in Decorated Cristobalite Frameworks," J. Am. Chem Soc. 123:4867-4868 (2001).

Li et al., "[Cd16In64S134]44-: 31-Å Tetrahedron with a Large Cavity," Angew. Chem. Int. Ed 42:1819-1821 (2003).

Li et al., "A metal-organic framework replete with ordered donor-acceptor catenanes," Chem. Commun. 46:380-382 (2010).

Li et al., "A Catenated Strut in a Catenated Metal-Organic Framework," Angew. Chem. Int. Ed. 49:6751-6755 (2010).

Linder, Nora. International Preliminary Report on Patentability for PCT/US2010/022777. Date of Mailing: Aug. 11, 2011.

Andrew et al., "Post-Synthetic Modification of Tagged MOFs," Angew. Chem. Int. Ed. 47:8482-8486 (2008).

(56) References Cited

OTHER PUBLICATIONS

Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions Within Metal-Organic Frameworks," Inorg. Chem. 49:6387-6389 (2010).
Carlucci et al., "Nanoporous three-dimensional networks topologically related to cooperite from the self-assembly of copper(I)centres and 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature 427, 523-527 (2004); Featured in (1) Chemical & Engineering News magazine, Feb. 9, 2004, (2) BBC World Service, Feb. 4, (3) New Scientist, Feb. 4.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Demir et al., "Role of Copper Species in the Oxidative Dimerization of Arylboronic Acids: Synthesis of Symmetrical Biaryls," Journal of Organic Chemistry 68(26):10130-10134 (2003).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Doonan et al., "Exceptional ammonia uptake by a covalent organic framework," Nature Chem. 2:235-238 (2010).
Duren et al., "Design of New Materials for Methane Storage," Langmuir 20:2683-2689 (2004).
Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2]2(H2O)2•(DMF)8(H2O)2: A Framework Deliberately Designed to have the NbO Structure Type," J. Am. Chem. Soc. 124:376-377 (2002).
Loeb, SJ, "Rotaxanes as ligands: from molecules to materials" Chemical Society reviews, 2007, 36, pp. 226-235.
Long et al., "The Pervasive Chemistry of Metal-Organic Frameworks," Chem. Soc. Rev. 38:1213-1214 (2009).

(56) References Cited

OTHER PUBLICATIONS

Lu et al., "Synthesis and Structure of Chemically Stable Metal-Organic Polyhedra," J. Am. Chem. Soc. 131:(35) 12532-12533 (2009).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No. PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Ni et al. "Porous Metal-Organic Truncated Octahedron Constructed from Paddle-Wheel Squares and Terthiophene Links," J. Am. Chem. Soc. 127:12752-12753 (2005).
Nickitas-Etienne, Athina International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068849. Date of Mailing: Jun. 30, 2011.
Niu et al., "Synthesis and structural characterization of the one dimensional polymers [Rh2(OAc)4(NCPhCN)S, S = CH3COCH3, CH3OH, C2H5OH, C4H8O, and C6H6," Polyhedron 17(23-24):4079-89 (1998).
Novoa, Carlos, International Search Report and Written Opinion for PCT/US2010/021201, European Patent Office. Date of Mailing: Apr. 27, 2010.
Oisaki et al., "A Metal-Organic Framework with Covalently Bound Organometallic Complexes," J. Am. Chem. Soc. 132:9262-9264 (2010).
O'Keefe et al., "Structural Study of New Hydrocarbon Nano-Crystals by Energy-Filtered Electron Diffraction," Ultramicroscopy 98:145-150 (2004).
O'Keefe et al., "Germanate Zeolites: Contrasting the Behavior of Germanate and Silicate Structures Built from Cubic T8O20 units (T = Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeeffe et al., "Reticular Chemistry—Present and Future Prospects—Introduction,"J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).
Phan et al., "Synthesis, Structure, and Carbon Dioxide Capture Properties of Zeolitic Imidazolate Frameworks," Acc. Chem. Res 43:58-67 (2009).
Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,OH,F)19 Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).
Reineke et al., "Large Free Volume In Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44: 4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Chen, L. et al., "Noncovalently Netted, Photoconductive Sheets with Extremely High Carrier Mobility and Conduction Anisotropy from Triphenylene-Fused Metal Trigon Conjugates," J. Am. Chem. Soc., 2009, vol. 131, pp. 7287-7292.
Young, Jung Doo, International Search Report and Written Opinion, PCT/US2012/023516, Korean Intellectual Property Offic, Oct. 19, 2012.
Becamel, Philippe, International Preliminary Report on Patentability, PCT/US2012/023516, The International Bureau of WIPO, Aug. 6, 2013.

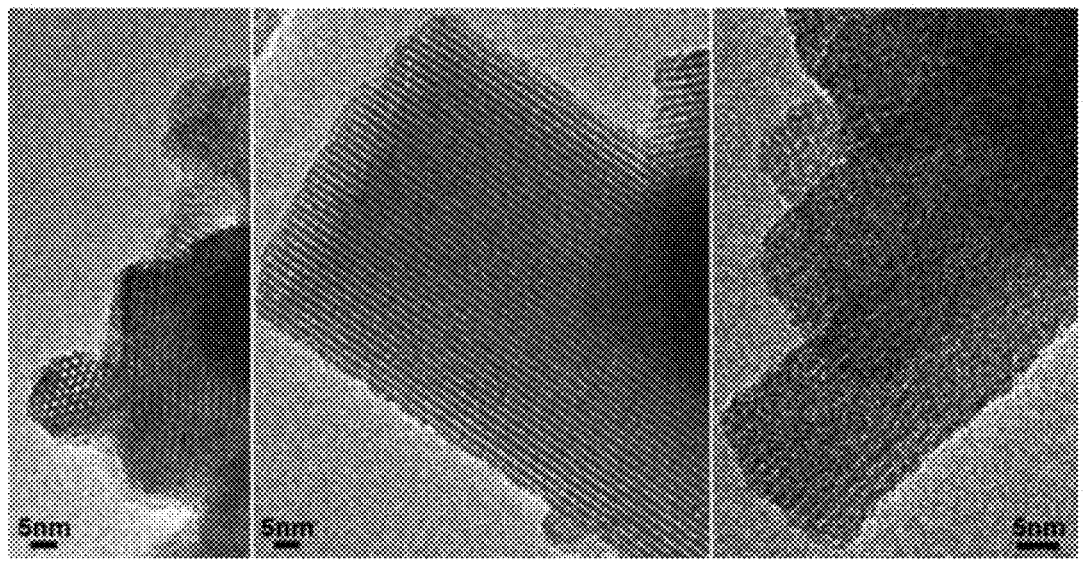
FIGURE 23
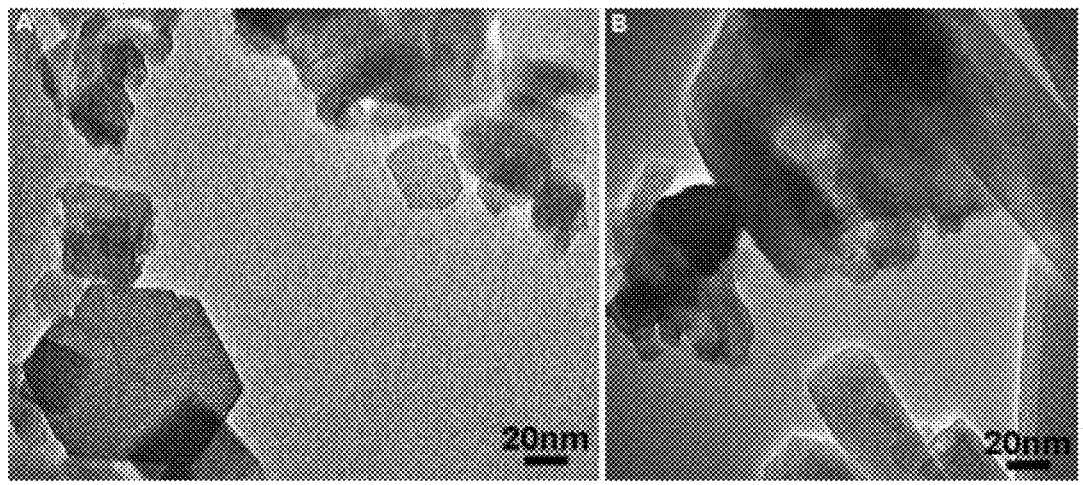
FIGURE 24A-B

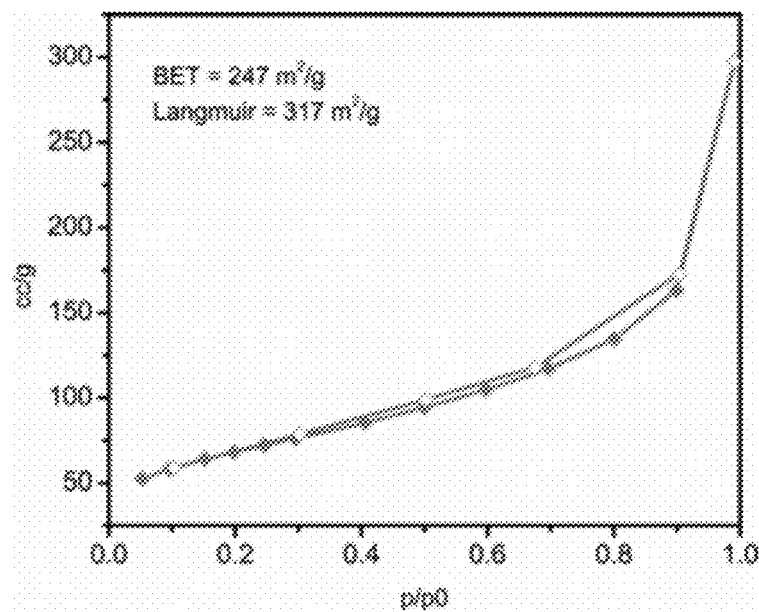
FIGURE 29
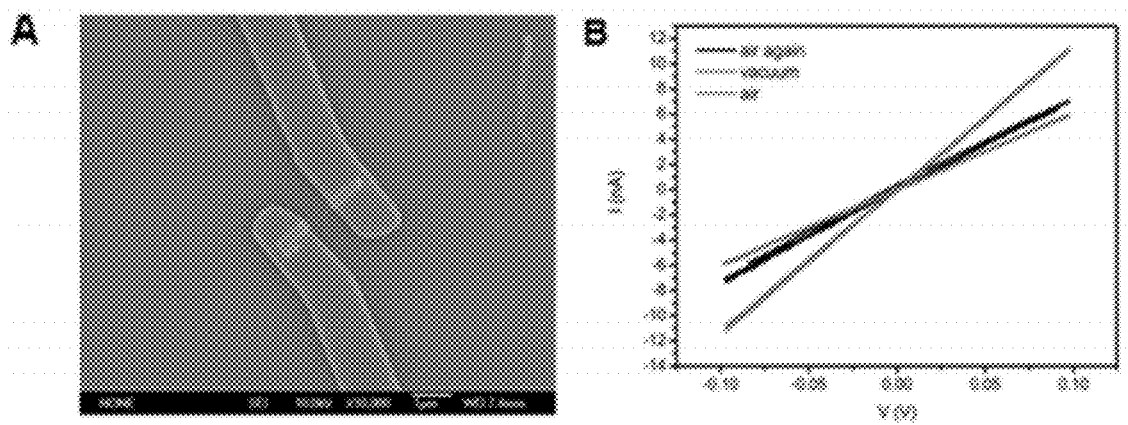
FIGURE 30A-B

PREPARATION OF METAL-CATECHOLATE FRAMEWORKS

STATEMENT REGARDING FEDERALLY SPONSORED RESEARCH

This invention was made with Government support of Grant No. DE-FG36-08GO18141 and DE-SC0001342, awarded by the United States Department of Energy. The Government has certain rights in this invention.

CROSS REFERENCE TO RELATED APPLICATIONS

This application claims priority under 35 U.S.C. §119 to U.S. Provisional Application Ser. No. 61/439,748, filed Feb. 4, 2011, the disclosure of which is incorporated herein by reference in its entirety.

FIELD OF THE INVENTION

This invention relates to porous metal organic frameworks and uses thereof.

BACKGROUND

A large segment of the global economy ($350 billion) is based on the use of metal porous frameworks in petrochemical cracking, ion-exchange for water softening and purification, and in the separation of gases.

SUMMARY

The disclosure provides various metal catecholate (CAT) frameworks. In a certain embodiment, the disclosure provides a CAT framework comprising one or more cores having the general structure of Formula I:

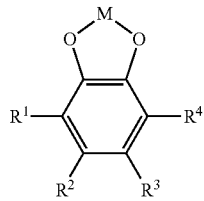

wherein M is a metal, a metal ion, or a metal containing complex; $R^1$-$R^4$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$-$R^4$ comprises one or more covalently bound functional groups that have denticity.

In another embodiment, the disclosure provides a CAT framework comprising one or more cores having the general structure of Formula I:

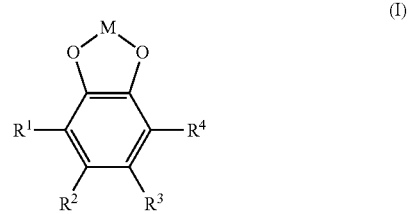

wherein, M is a metal, metal ion, or metal containing complex; $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(R_9SH)_2$, $C(R_5SH)_3$, $CH(R_5NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In yet another embodiment, the disclosure provides a CAT framework comprising one or more cores having the general structure of Formula I:

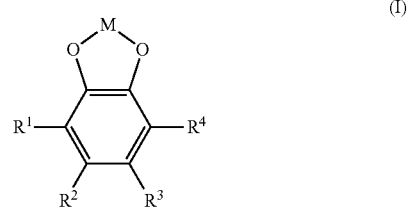

wherein M is a metal, metal ion, or metal containing complex; $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, mixed ring system, and catechol; $X^1$ is an alkyl group having from 1 to 5 carbon atoms, or an aryl group consisting of 1 to 2 phenyl rings; and wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(R_9SH)_2$, $C(R_5SH)_3$, $CH(R_5NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$.

In a further embodiment, the disclosure provides for a CAT framework, comprising one or more core units comprising Formula IV(a):

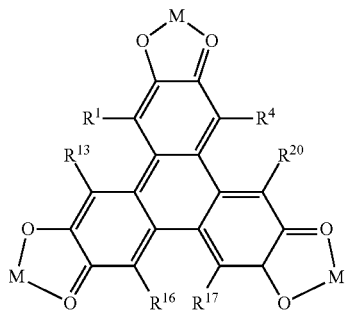

IV(a)

wherein M is each individually a metal, metal ion, or metal containing complex; $R^1$, $R^4$, $R^{13}$, $R^{16}$-$R^{17}$, and $R^{20}$ are each individually selected from the group comprising H, D, optionally substituted FG, optionally substituted $(C_1$-$C_6)$ alkyl, optionally substituted $(C_1$-$C_5)$heteroalkyl, optionally substituted $(C_1$-$C_6)$alkenyl, optionally substituted $(C_1$-$C_5)$ heteroalkenyl, optionally substituted $(C_1$-$C_6)$alkynyl, and optionally substituted $(C_1$-$C_5)$heteroalkynyl.

In an additional embodiment, the disclosure provides for a CAT framework comprising one or more core units comprising Formula IV(b):

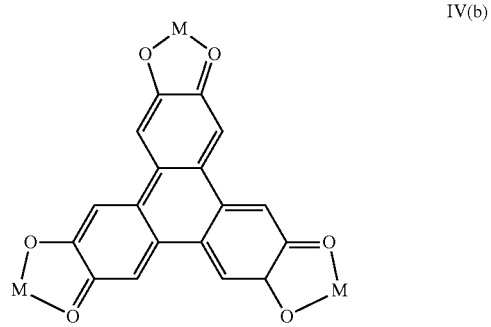

IV(b)

wherein, M is each individually a metal, metal ion, or metal containing complex.

In yet another embodiment, the disclosure provides for a CAT framework comprising one or more core units comprising Formula V:

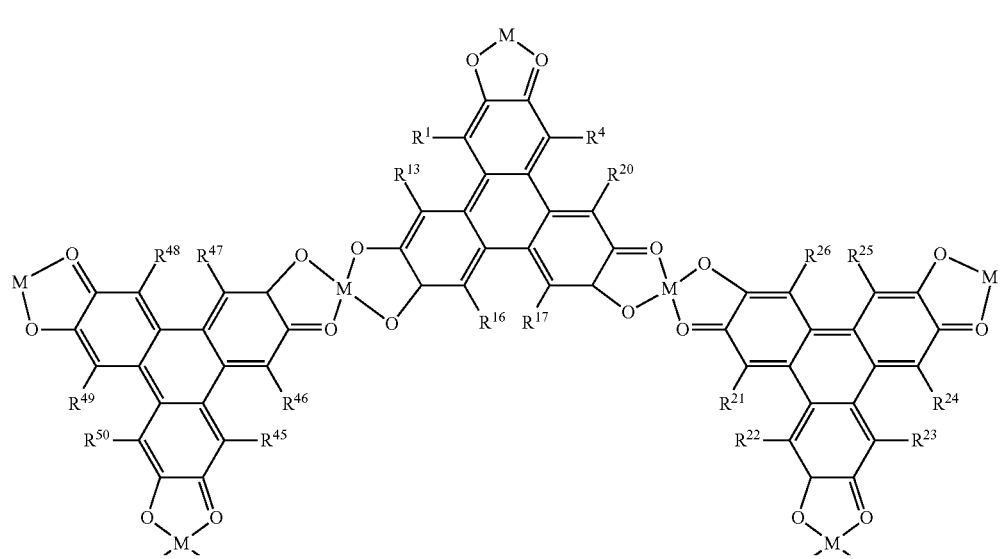

(V)

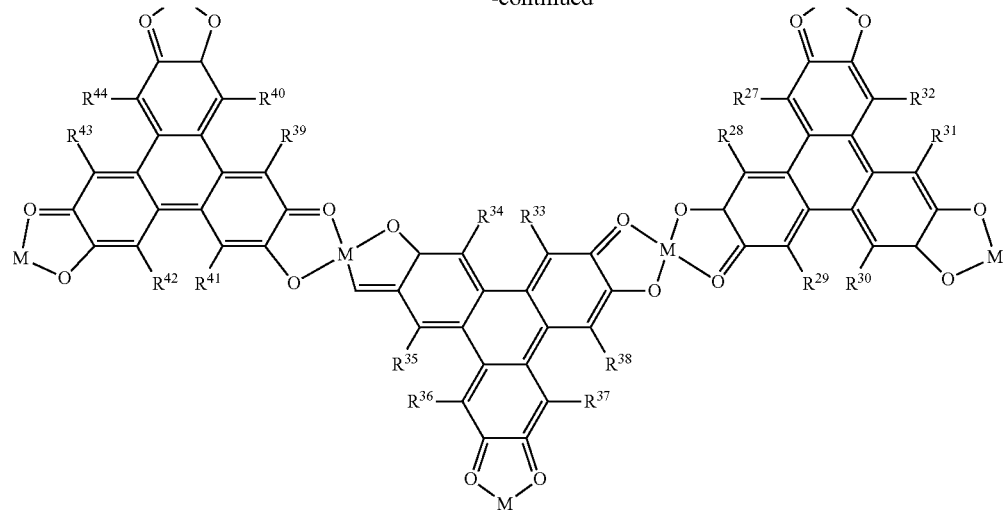

wherein M is each individually a metal, metal ion, or metal containing complex; $R^1$, $R^4$, $R^{13}$, $R^{16}$, $R^{17}$, and $R^{20}$-$R^{50}$ are independently selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, optionally substituted ($C_1$-$C_5$)heteroalkynyl, optionally substituted ($C_1$-$C_6$)cycloalkyl, optionally substituted ($C_1$-$C_6$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, $R^{13}$, $R^{16}$-$R^{17}$, and $R^{20}$-$R^{50}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 2 carbon atoms.

In a certain embodiment, the disclosure provides for a CAT framework comprising one or more core units comprising Formula V(a):

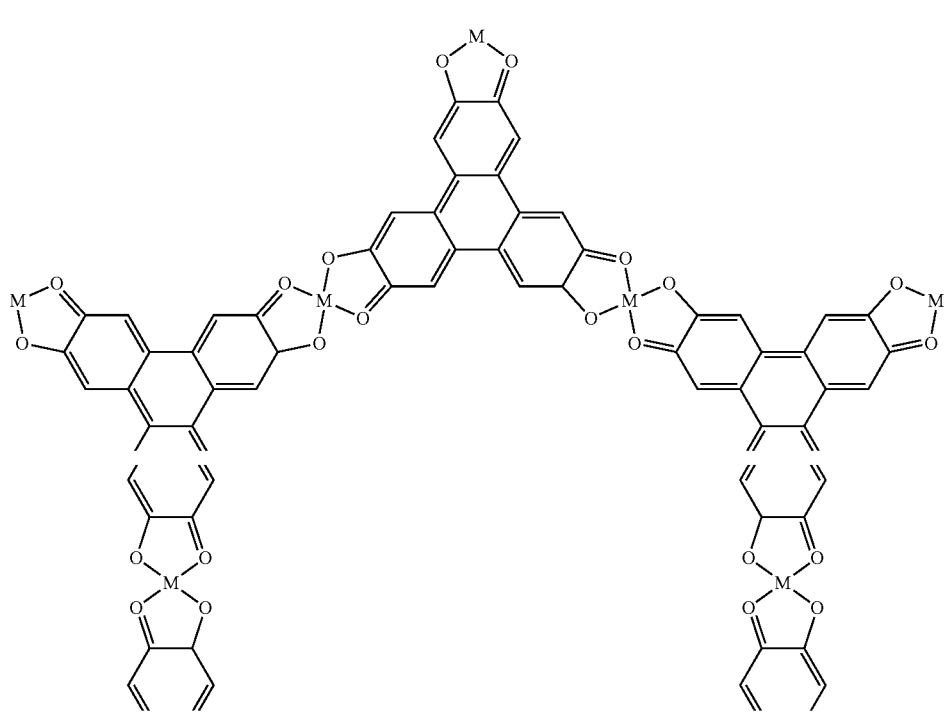

V(a)

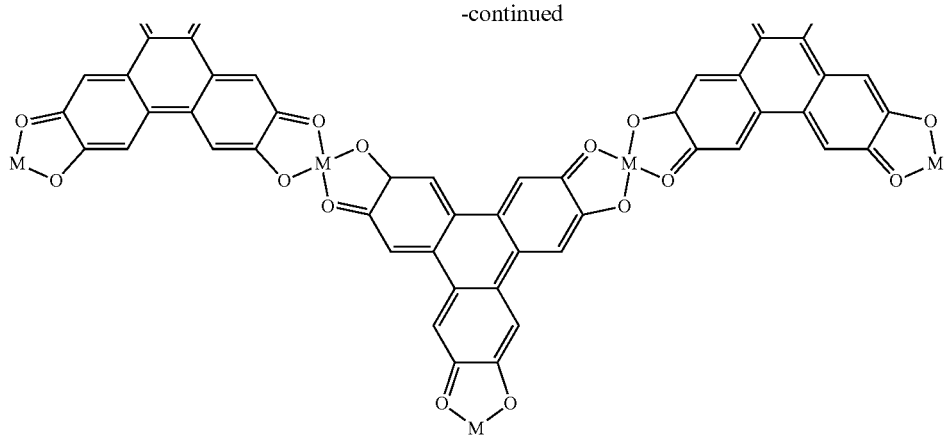

wherein, M is each individually a metal, metal ion, or metal containing complex.

The disclosure also provides for CAT frameworks that are comprised of homogenous or heterogeneous cores. For example, a CAT framework can be comprised of a core selected from the group comprising Formulas I(a), II(a), III(a), IV(a), V(a), or VI(a). Alternatively, a CAT framework can be comprised of two or more cores selected from the group comprising Formulas I(a), II(a), III(a), IV(a), V(a), or VI(a). In a certain embodiment, a CAT framework which comprises a core of Formula IV(a), further comprises one or more cores selected from the group comprising Formula I(a), II(a), III(a), or VI(a):

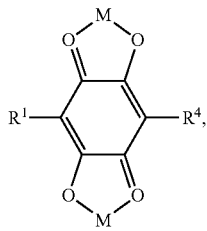

I(a)

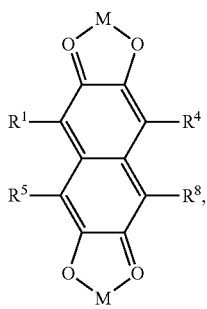

II(a)

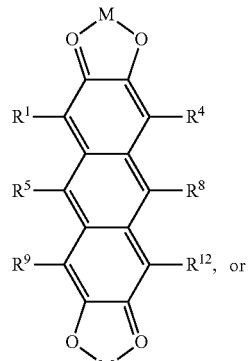

III(a)

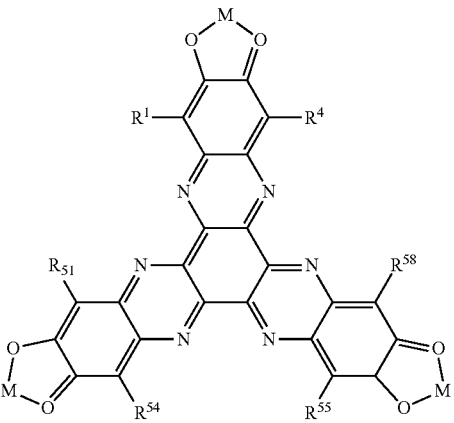

VI(a)

wherein M is each individually a metal, metal ion, or metal containing complex; $R^1$, $R^4$-$R^5$, $R^8$-$R^9$, $R^{12}$, $R^{51}$, $R^{54}$-$R^{55}$ and $R^{58}$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, and optionally substituted ($C_1$-$C_5$)heteroalkynyl.

The disclosure also provides that one or more cores contain one or more metal, metal ions, or metal containing complexes. The metal, metal ion or metal containing complex typically comprises a transition metal, but the disclosure also provides for metal, metal ion, or metal containing complexes comprised of alkali metals, alkaline earth metals, lanthanides, actinides, and post-transition metals. In a particular embodiment, a CAT framework is comprised of one or more cores which contain metals or metal ions selected from the group comprising $Li^+$, $Na^+$, $K^+$, $Rb^+$, $Cs^+$, $Be^{2+}$, $Mg^{2+}$, $Ca^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$. In another embodiment, a CAT framework is comprised of one or more cores which contain one metals or metal ions selected from the group comprising $Li^+$, $Mg^{2+}$, $Ca^{2+}$, $Ba^{2+}$, $Zr^{4+}$, $Zr^{3+}$, $Zr^{2+}$, $Mn^{3+}$, $Mn^{2+}$, $Mn^+$, $Fe^{3+}$, $Fe^{2+}$, $Fe^+$, $Ni^{3+}$, $Ni^{2+}$, $Ni^+$, $Ni$, $Cu^{4+}$, $Cu^{3+}$, $Cu^{2+}$, $Cu^+$, $V^{5+}$, $V^{4+}$, $V^{3+}$, $V^{2+}$, $Co^{3+}$, $Co^{2+}$, $Co^+$, $Zn^{2+}$, $Zn^+$, $Ce^{4+}$, $Ce^{3+}$, and $Ce^{2+}$. In yet another embodiment, a CAT framework is comprised of one or more cores which contain one or more metal ions selected from the group comprising $Li^+$, $Mg^{2+}$, $Ca^{2+}$, $Ba^{2+}$, $Zr^{2+}$, $Mn^2$, $Fe^{2+}$, $Ni^{2+}$, $Cu^{2+}$, $V^{2+}$, $Co^{2+}$, $Zn^{2+}$, and $Ce^{2+}$. In a further embodiment, a CAT framework is comprised of cores which contain either $Ni^{2+}$ or $Co^{2+}$ metal ions.

The disclosure provides for the preparation of CAT frameworks by reacting framework metals, metal ions, or metal containing complexes with linking moieties which contain at least one catechol-based linking cluster and at least one additional catechol-based or non-catechol-based linking cluster. In a preferred embodiment, the framework metals, metal ions, or metal containing complexes are reacted with linking moieties which contain exclusively catechol-based linking clusters. In such a case, the linking moieties may have at least two, or at least three catechol-based linking clusters. In a certain embodiment, the disclosure provides for a CAT framework comprised of one or more cores that are comprised of one or more linking moieties having a structure of Formula IX(a):

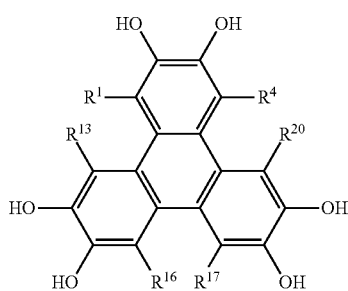

wherein, $R^1$, $R^4$, $R^{13}$, $R^{16}$-$R^{17}$, and $R^{20}$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$) alkenyl, optionally substituted ($C_1$-$C_5$)heteroalkenyl, optionally substituted ($C_1$-$C_6$)alkynyl, and optionally substituted ($C_1$-$C_5$)heteroalkynyl.

In a particular embodiment, the disclosure provides for a CAT framework, wherein one or more cores is comprised of one or more linking moieties having a structure of Formula IX(b):

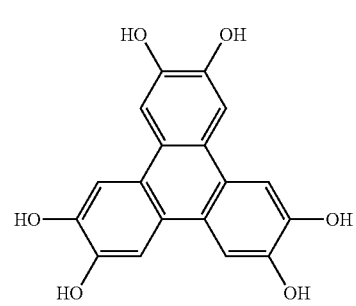

The disclosure also provides for CAT frameworks that are comprised of homogenous cores derived from one type of linking moiety, such as VII(a), VIII(a), IX(a), X(a), or XI(a). Moreover, the disclosure also provides for CAT frameworks that are comprised of heterogeneous cores, such as a combination of VII(a), VIII(a), IX(a), X(a), or XI(a). In a certain embodiment, a CAT framework which is comprised of one or more cores prepared from a linking moiety having Formula X(a), is further comprised of one or more cores prepared from one or more linking moieties selected from the group comprising Formula VII(a), VIII(a), IX(a), or XI(a):

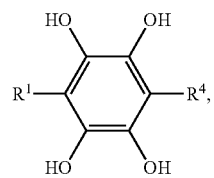

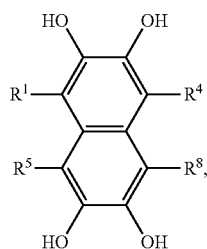

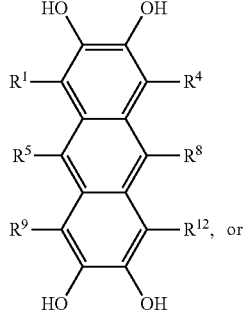

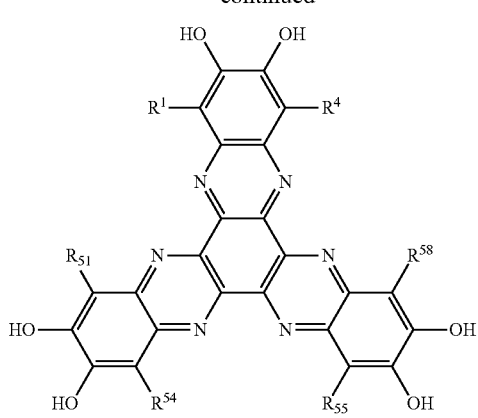

wherein, $R^1$, $R^4$-$R^5$, $R^8$-$R^9$, $R^{12}$, $R^{51}$, $R^{54}$-$R^{55}$ and $R^{58}$ are each individually selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, and optionally substituted ($C_1$-$C_5$)heteroalkynyl.

The disclosure also provides for CAT frameworks, wherein the pores of the framework are activated by being substantially free of any guest molecules. Alternatively, the disclosure provides for CAT frameworks, wherein the pores of the framework are not activated in that the pores are not free of guest molecules.

In a certain embodiment, the disclosure provides that the CAT framework is not reacted with one or more post framework reactants. Alternatively, in another embodiment, the disclosure also provides that the synthesized CAT framework is reacted with one or more post framework reactants. The post framework reactants can modify or add functionality and/or characteristics of the CAT framework by adding at least one effect or alternatively at least two effects to the CAT framework. Examples of such effects include: modulating the gas storage ability of the CAT framework; modulating the sorption properties of the CAT framework; modulating the pore size of the CAT framework; modulating the catalytic activity of the CAT framework; modulating the conductivity of the CAT framework; and modulating the sensitivity of the CAT framework to the presence of an analyte of interest.

The disclosure provides that the CAT frameworks described herein exhibit a variety of useful properties, including, but not limited to, gas separation, gas storage, catalysis, tunable conductors, supercapacitors, and sensors. In a certain embodiment, the disclosure provides for a CAT framework that is further comprised of one or more absorbed or adsorbed chemical species. Examples of such chemical species include, but are not limited to, gases, optionally substituted ($C_1$-$C_{25}$) organic molecules, inorganic molecules, and combinations thereof. In further embodiment, the disclosure provides for a CAT framework which is further comprised of one or more adsorbed or absorbed chemical species selected from the group comprising argon, ammonia, carbon dioxide, carbon monoxide, hydrogen, amines, oxygen, ozone, nitrogen, nitrous oxide, organic dyes, polycyclic organic molecules, hydrogen sulfide, carbonyl sulfide, carbon disulfide, mercaptans, hydrocarbons, formaldehyde, diisocyanates, trichloroethylene, fluorocarbons, and combinations thereof. In yet a further embodiment, the disclosure provides for a CAT framework which is further comprised of one or more adsorbed or absorbed chemical species selected from the group comprising argon, carbon dioxide, carbon monoxide, hydrogen, nitrogen, hydrogen sulfide, carbonyl sulfide, carbon disulfide, mercaptan, and combinations thereof. In another embodiment, the disclosure provides for a CAT framework which is further comprised of one or more adsorbed or absorbed chemical species selected from the group comprising hydrogen, carbon dioxide, carbon monoxide, or a combination thereof.

The disclosure also provides that one of the many useful properties of the CAT frameworks disclosed herein is that the CAT frameworks can be used to separate or store one or more gases from a mixed gas mixture by, for example, coming into contact with the gas mixture. In a certain embodiment, the disclosure provides a method of separating and/or storing one or more high electron density gases by, for example, having a CAT framework described herein coming into contact with the gas mixture. In another embodiment, the disclosure provides a method of separating and/or storing one or more gases from a fuel gas stream, for example, by having a CAT framework described herein coming into contact with a fuel gas stream. Examples of fuel gas streams, include, but are not limited to, natural gas, town gas, syngas, and biogas. In respect to a natural gas stream, a CAT framework disclosed herein can be used to separate and/or store one or more acid gases from a natural gas stream by having one or more CAT frameworks come into contact with the natural gas stream.

The disclosure also provides for methods to separate or store one or more gases from the exhaust of a combustion engine comprising contacting the exhaust with one or more CAT frameworks disclosed herein. In a certain embodiment, the disclosure provides a method to separate or store one or more gases from flue-gas comprising contacting the flue-gas with one or more CAT frameworks disclosed herein.

The disclosure also provides for various types of devices which comprise one or more CAT frameworks disclosed herein. Examples of such devices, include, but are not limited to, a gas storage device, and a gas separation device. In a particular embodiment, the disclosure provides for CAT frameworks disclosed herein comprising part of a gas storage or a gas separation device selected from the group comprising purifiers, filters, scrubbers, pressure swing adsorption devices, molecular sieves, hollow fiber membranes, ceramic membranes, cryogenic air separation devices, and hybrid gas separation devices. In another embodiment, the disclosure provides for CAT frameworks disclosed herein comprising part of carbon monoxide detectors, air purifiers, fuel gas purifiers, and devices to measure emissions from combustion engines.

The disclosure also provides for a chemical sensor, catalyst, tunable conductor or supercapcitor, comprising a CAT framework of the disclosure.

DESCRIPTION OF DRAWINGS

FIG. 23 provides HRTEM images of an activated Ni-CAT-1 specimen observed at 30 kV. The images show that the specimens are damaged most easily under 30 kV even when the beam densities are the same.

FIG. 24 provides HRTEM images of an activated Ni-CAT-1 specimen observed at 60 kV; (A) HRTEM images of Ni-CAT-1 in mother liquid specimen observed at 60 kV; and (B) demonstrates that there is less damage of the specimens at 60 kV.

FIG. 29 presents a $N_2$ isotherm curve of Zr-CAT-1. Adsorption and desorption points are represented by filled and empty circles, respectively.

FIG. 30A-B provides (A) an Electron Microscope image of Cu-CAT-1 connected to electrodes; and (B) presents a conductivity measurement plot of Cu-CAT-1 in the indicated environments.

DETAILED DESCRIPTION

Figure 1:
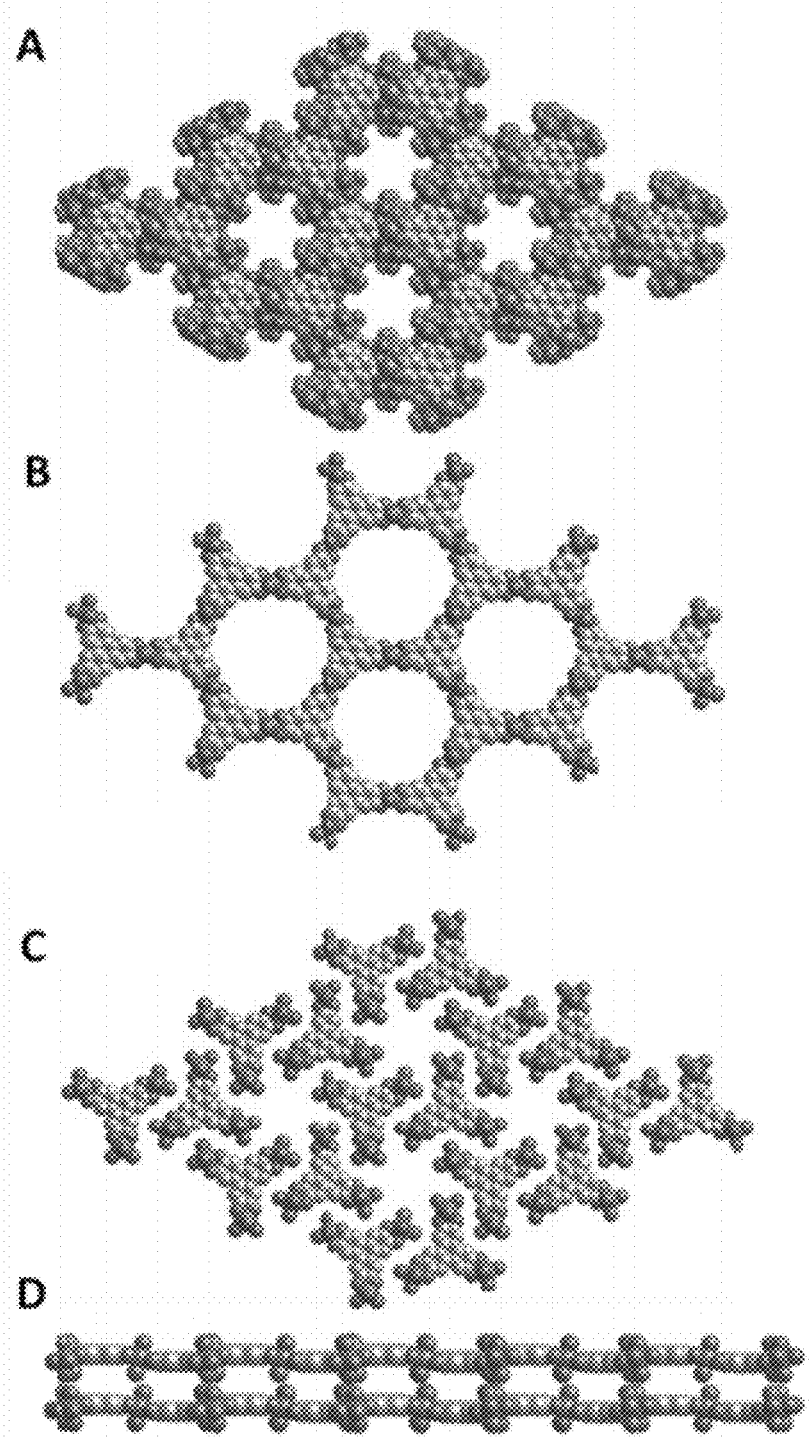
FIG. 1A-D presents space filing drawings of single-crystal structure of the Co-CAT structure. (A) View of the Co-CAT structure along the c axis. (B) Extended layer of Co-CAT. (C) Layer formed by the trinuclear complexes $CO_3HTTP$ $(H_2O)_{12}$. (D) View of the two extended corrugated layers along the [110] direction. Code: Co, larger dark grey spheres; C, light gray spheres; and O, smaller dark grey spheres. The hydrogen atoms have been omitted for clarity.

As used herein and in the appended claims, the singular forms "a," "and," and "the" include plural referents unless the context clearly dictates otherwise. Thus, for example, reference to "a pore" includes a plurality of such pore and reference to "the metal" includes reference to one or more metals known to those skilled in the art, and so forth.

Also, the use of "or" means "and/or" unless stated otherwise. Similarly, "comprise," "comprises," "comprising" "include," "includes," and "including," and "have," "haves," and "having," are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

All publications mentioned throughout the disclosure are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

A "metal catecholate framework", as used herein, refers to a framework of repeating cores having a plurality of metals, metal ions, or metal containing complexes linked by a plurality of catechol-based linking moieties.

A "catecholate", as used herein, refers to a metal containing complex, metal, or metal ion which is coordinated to a catechol moiety. While it is preferable that the catechol moiety links a single metal containing complex, metal, or metal ion in a multidentate manner, the disclosure also provides for linkages of two metal containing complexes, metals, or metal ions linked to each oxygen atom of a single catechol in either a syn or anti manner.

A "catechol", as used herein, refers to a substituted or unsubstituted 1,2-dihydroxybenzene-based compound or moiety which may be optionally substituted.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

A "metal containing complex" refers to complexes of a metal or metal ion, wherein the metal or metal ion is centrally located and surrounded by a number of other molecules or ions. These molecules or ions are generally interacting with the central metal or metal ion through one or more coordinate bonds.

The term "cluster" refers to identifiable associations of 2 or more atoms. Such associations are typically established by some type of bond-ionic, covalent, Van der Waal, coordinate and the like.

A "linking moiety" refers to a parent chain that contains at least one catechol moiety or derivative thereof that can bind at least one metal, metal ion, or metal containing complex. A linking moiety may be further substituted post synthesis of the metal catecholate framework by reacting with one or more post-framework reactants.

The term "linking cluster" refers to one or more atoms capable of forming an association, e.g. covalent bond, polar covalent bond, ionic bond, and Van Der Waal interactions, with one or more atoms of another linking moiety, and/or one or more metal, metal ions, or metal containing complexes. A linking cluster can be part of the parent chain itself, e.g. the oxygen atoms in catechol, and/or additionally can arise from functionalizing the parent chain, e.g. adding carboxylic acid groups to the catechol-based parent chain. For example, a linking cluster can comprise OH, 1,2-diols, NN(H)N, N(H)NN, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Generally for a metal catecholate framework disclosed herein, the linking cluster(s) that bind one or metal or metal ions and/or associate with one or more atoms of another linking moiety comprise at least one, and preferably two of the oxygen atoms of the catechol-based parent chain. The catechol-based parent chain may be further substituted with one or more linking clusters, however, and can therefore form associations with one or more metal or metal ions and/or one or more atoms of another linking moiety in addition to, or alternatively to, the oxygen atom-based linking cluster(s) of the catechol-based parent chain. Generally, the linking clusters disclosed herein are Lewis bases, and therefore have lone pair electrons available and/or can be deprotonated to form stronger Lewis bases. The deprotonated version of the linking clusters, therefore, are encompassed by the disclosure and anywhere a linking cluster that is depicted in a non-de-protonated form, the de-protonated form should be presumed to be included, unless stated otherwise. For example, although the structural Formulas presented herein are illustrated as having hydroxyls, for the purposes of this disclosure, these illustrated structures should be interpreted as including both hydroxyls and de-protonated hydroxyls.

The term "coordination complex" refers to a central metal or a metal ion that is coordinated by one or more linking clusters of one or more linking moieties by forming coordinate bonds with the central metal or metal ion. For purposes of this disclosure a "coordination complex" includes complexes arising from linking moieties that have monodentate and/or polydentate linking clusters.

The term "alkyl", refers to an organic group that is comprised of carbon and hydrogen atoms that contains single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "aryl", as used in this disclosure, refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle", as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo [2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing a hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but are not limited to, quinuclidinyl, diazabicyclo[2.2.1]heptyl; and 7-oxabicyclo[2.2.1]heptyl.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2, 4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

As used herein, a "core" refers to a repeating unit or units found in a metal catecholate framework. Such a metal catecholate framework can comprise a homogenous repeating core, a heterogeneous repeating core or a combination of homogenous and heterogeneous cores. A core comprises a metal, metal ion, and/or metal containing complex or a cluster of metals, metal ions, and/or metal containing complexes and a linking moiety. Various cores are depicted as structures throughout the disclosure as Formulas. The coordinate bonds, however, between metals and/or metal ions to various ligands that arise from reagents or solvents have been omitted for clarity. Therefore, a person of skill in the art should assume that the metal and/or metal ions can and do form coordinate bonds with these ligands even though they are not visually depicted in the Formulas.

The term "post framework reactants" refers to all known substances that are directly involved in a chemical reaction. Post framework reactants typically are substances, molecules, or compounds which have not reached the optimum number of electrons in their outer valence levels, and/or have not reached the most favorable energetic state due to ring strain, bond length, low bond dissociation energy, and the like. Some examples of post framework reactants include, but are not limited to:

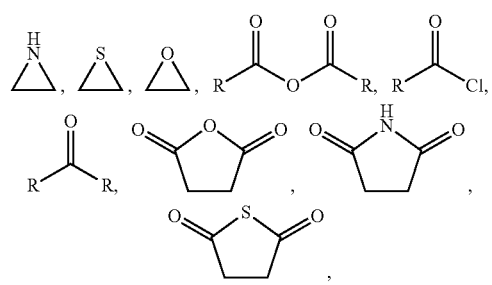

I—R, Br—R, $CR_3$—Mg—Br, $CH_2R$—Li, $CR_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. $CO_2$ is corrosive in the presence of water, and it can form dry ice, hydrates and can cause freeze-up problems in pipelines and in cryogenic equipment often used in processing natural gas. Also, by not contributing to the heating value, $CO_2$ merely adds to the cost of gas transmission.

In addition, removal of carbon dioxide from the flue exhaust of power plants, currently a major source of anthropogenic carbon dioxide is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake. However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level finetuning can be achieved for optimized uptake capacities.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

As society at-large has become more dependent on electrical devices, there has been a growing demand to develop low cost and/or high density electronic components. While inorganic materials, specifically silicon, has been the traditional choice, new materials are being investigated and developed. Research has focused on three classes of new materials: materials based on hybridizing inorganic metals/metal ions in an organic framework, metallic nanoparticles, and organic semiconductors.

While organic semiconductors are lighter and more tunable than their inorganic counterparts, they are less efficient at conducting electricity. Materials composed of inorganic and organic components, however, can take advantage of both the inorganic components lower electrical resistance and the organic components better tunability, to give superior tunable conductors.

A supercapacitor device typically comprises a pair of electrodes separated by a non-conductive porous separator. The space between the electrodes is filled with a liquid electrolyte, which can either be aqueous or non-aqueous. One key ways to improve the energy storage of supercapacitors is to optimize the interactions between the electrodes and electrolyte. Double-layer supercapacitors typically consist of high surface area carbon structures that store energy in a polarized liquid layer. The larger the area of solid/liquid interface, the more energy that can be stored. One of the key ways to maximize the area of solid/liquid interface is to optimize pore size. One of the major drawbacks of carbon frameworks now used in double-layer supercapacitors is poor capacitance. This poor capacitance results from pores in the carbon framework being too large.

Metal-organic frameworks (MOFs) are extended porous structures composed of transition metal ions (or clusters) that are joined by organic links via bridging units. These coordination units afford a wide variety of binding strength and directionality. To date, most of the anionic coordination units used in the extended structures are based on carboxylate, imidazolate, tetrazolate or pyrazolate. The disclosure describes the successful incorporation of a tricatecholate, planar and highly conjugated link, namely 2,3,6,7,10,11-Hexahydroxytriphenylene (HHTP), into a two-dimensional extended framework. These new crystalline materials, termed metal catecholates (CATs), exhibit high thermal and chemical stability as well as permanent porosity.

The disclosure provides metal catecholate frameworks comprising a network of homogenous metals, homogeneous metal ions, heterogeneous metals, or heterogeneous metal ions linked by a homogenous or heterogeneous linking moiety.

The disclosure provides for the preparation of metal catecholate (CAT) frameworks. Scheme I presents a generalized scheme for forming one or more cores of the disclosure by coordinating one or more linking clusters of a linking moiety with a metal ion disclosed herein.

Scheme I

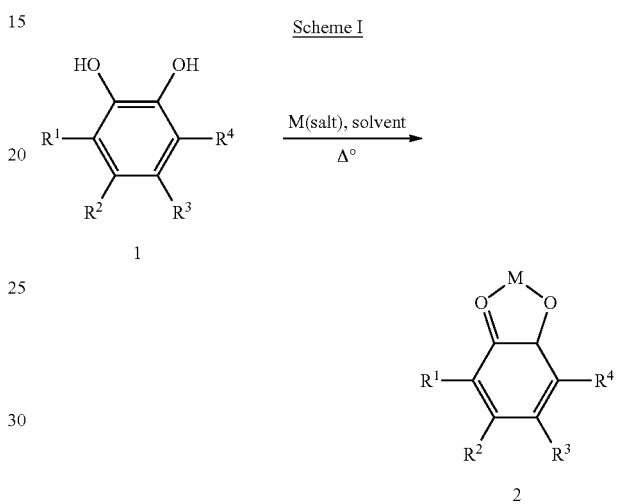

A catechol-based linking moiety 1 coordinates with the metal ion of a metal containing salt under solvothermal reaction conditions to afford core 2 of the disclosure.

In a certain embodiment, the disclosure provides a CAT framework comprising one or more cores having the general structure of Formula I:

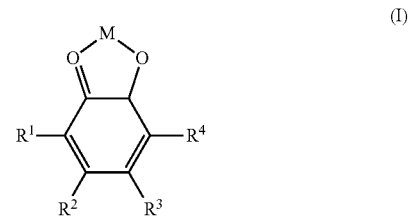

(I)

M is each individually a metal, metal ion, or metal containing complex; $R^1$-$R^4$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$-$R^4$ comprises one or more covalently bound functional groups that have denticity.

In another embodiment, the disclosure provides a framework comprising one or more cores having the general structure of Formula I:

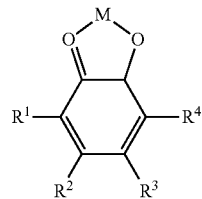

(I)

wherein M is each individually a metal, metal ion, or metal containing complex; $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In yet another embodiment, the disclosure provides a framework comprising one or more cores having the general structure of Formula I:

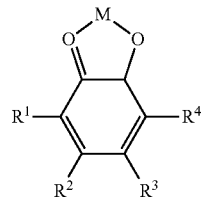

(I)

wherein M is each individually a metal, metal ion, or metal containing complex; $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, mixed ring system, and catechol; wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a further embodiment, the disclosure provides a framework comprising one or more cores having the general structure of Formula I(a):

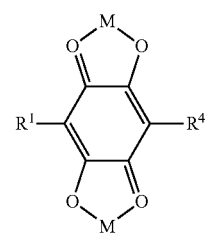

I(a)

wherein M is each individually a metal, metal ion, or metal containing complex; $R^1$ and $R^4$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, and optionally substituted ($C_1$-$C_5$) heteroalkynyl.

In a certain embodiment, the disclosure provides a framework comprising one or more cores having the general structure of Formula I(b):

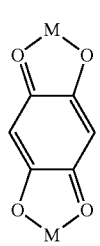

I(b)

wherein, M is each individually a metal, metal ion, or metal containing complex.

In yet a further embodiment, the disclosure provides a framework comprising one or more cores having the general structure of Formula II:

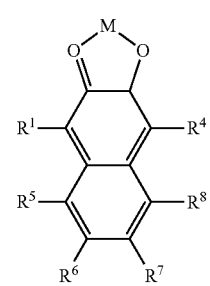

(II)

wherein M is each individually a metal, metal ion, or metal containing complex; $R^1$, $R^4$, and $R^5$-$R^8$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$, and $R^5$-$R^8$ comprises one or more covalently bound functional groups that have denticity.

In yet a further embodiment, the disclosure provides a framework comprising one or more cores having the general structure of Formula II:

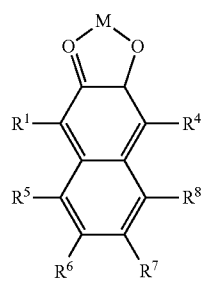

(II)

M is each individually a metal, metal ion, or metal containing complex; $R^1$, $R^4$, and $R^5$-$R^8$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, and $R^5$-$R^8$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a further embodiment, the disclosure provides a framework comprising one or more cores having the general structure of Formula II(a):

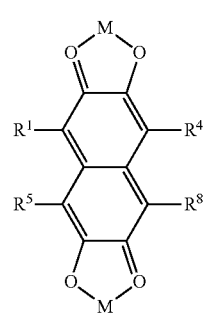

(II(a))

wherein M is each individually a metal, metal ion, or metal containing complex;
$R^1$, $R^4$-$R^5$, and $R^8$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, and optionally substituted ($C_1$-$C_5$)heteroalkynyl.

In yet a further embodiment, the disclosure provides a framework comprising one or more cores having the general structure of Formula II(b):

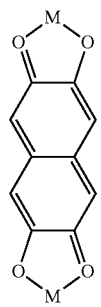

(II(b))

wherein, M is each individually a metal, metal ion, or metal containing complex.

In yet a further embodiment, the disclosure provides a framework comprising one or more cores having the general structure of Formula III:

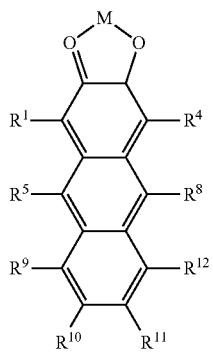

(III)

wherein M is each individually a metal, metal ion, or metal containing complex; $R^1$, $R^4$-$R^5$, $R^8$-$R^{12}$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$-$R^5$, $R^8$-$R^{12}$ comprises one or more covalently bound functional groups that have denticity.

In yet a further embodiment, the disclosure provides a framework comprising one or more cores having the general structure of Formula III:

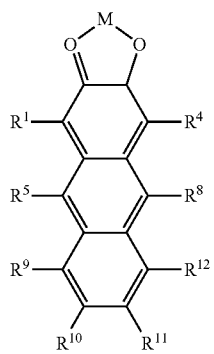

(III)

M is each individually a metal, metal ion, or metal containing complex; $R^1$, $R^4$-$R^5$, $R^8$-$R^{12}$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$-$R^5$, $R^8$-$R^{12}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a further embodiment, the disclosure provides a framework comprising one or more cores having the general structure of Formula III(a):

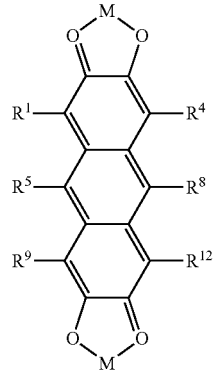

III(a)

wherein M is each individually a metal, metal ion, or metal containing complex; $R^1$, $R^4$-$R^5$, $R^8$-$R^9$, and $R^{12}$ are each individually selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, and optionally substituted ($C_1$-$C_5$)heteroalkynyl.

In yet a further embodiment, the disclosure provides a framework comprising one or more cores having the general structure of Formula III(b):

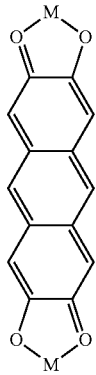

III(b)

wherein, M is a metal, metal ion, or metal containing complex.

In yet a further embodiment, the disclosure provides a framework comprising one or more cores having the general structure of Formula IV:

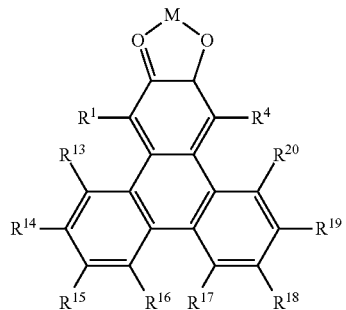

(IV)

wherein M is each individually a metal, metal ion, or metal containing complex; $R^1$, $R^4$, and $R^{13}$-$R^{20}$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$, and $R^{13}$-$R^{20}$ comprises one or more covalently bound functional groups that have denticity.

In yet a further embodiment, the disclosure provides a framework comprising one or more cores having the general structure of Formula IV:

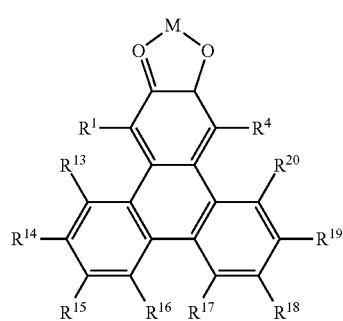

(IV)

M is each individually a metal, metal ion, or metal containing complex; $R^1$, $R^4$, and $R^{13}$-$R^{20}$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, and $R^{13}$-$R^{20}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1OH)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a further embodiment, the disclosure provides a framework comprising one or more cores having the general structure of Formula IV(a):

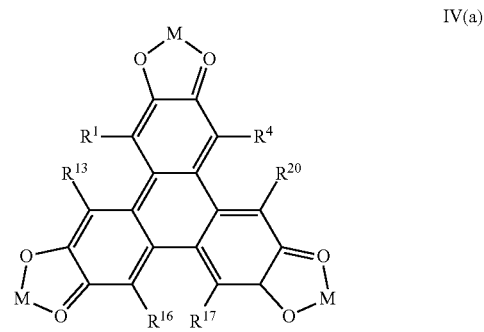

IV(a)

wherein M is each individually a metal, metal ion, or metal containing complex; $R^1$, $R^4$, $R^{13}$, $R^{16}$-$R^{17}$, and $R^{20}$ are each individually selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, and optionally substituted ($C_1$-$C_5$)heteroalkynyl.

In a certain embodiment, the disclosure provides a framework comprising one or more cores having the general structure of Formula IV(b):

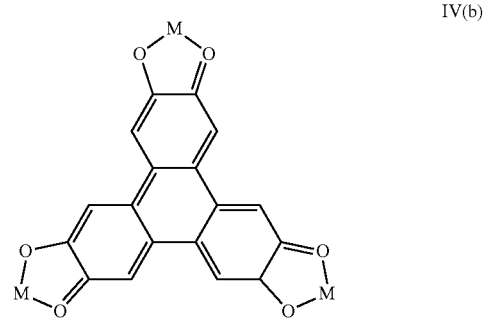

IV(b)

wherein, M is each individually a metal, metal ion, or metal containing complex.

In another embodiment, the disclosure provides a framework comprising one or more cores having the general structure of Formula V:

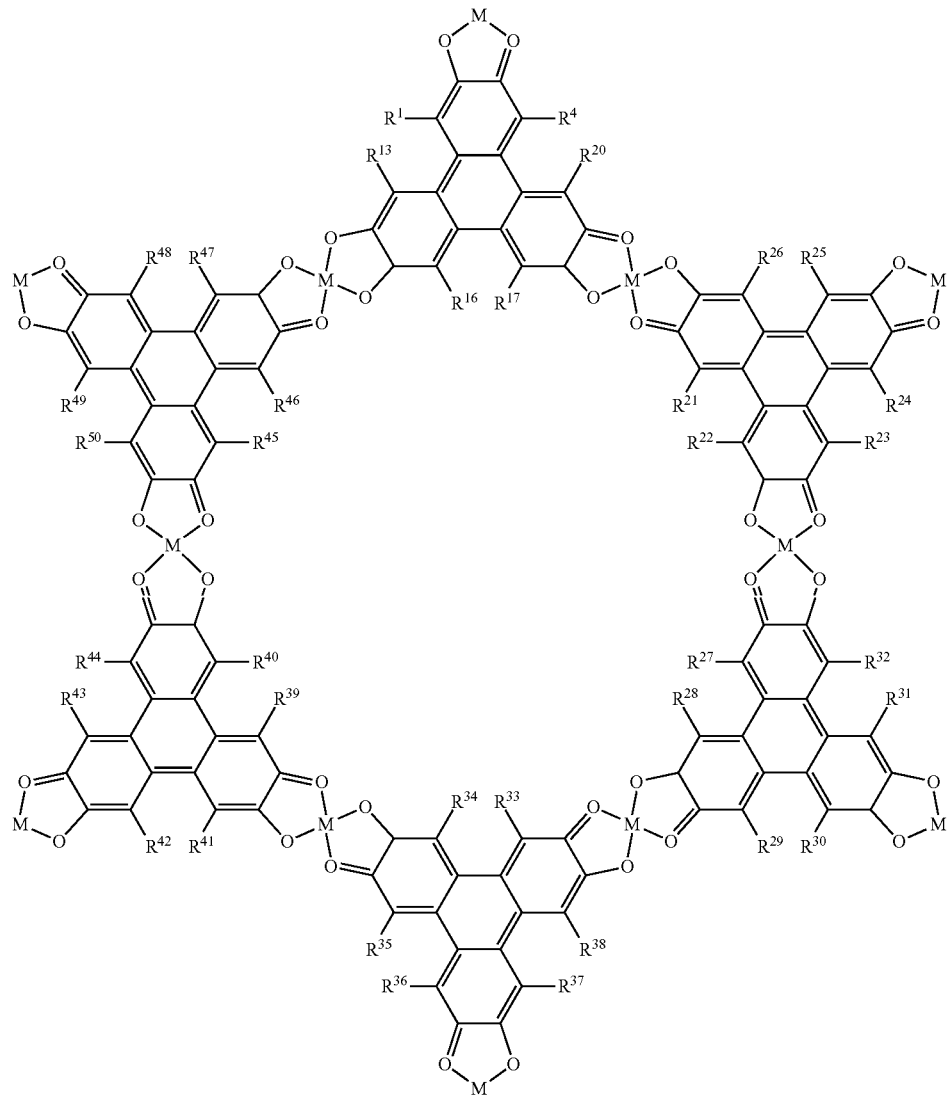

(V)

wherein M is each individually a metal, metal ion, or metal containing complex; $R^1$, $R^4$, $R^{13}$, $R^{16}$-$R^{17}$, and $R^{20}$-$R^{50}$ are independently selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, optionally substituted ($C_1$-$C_5$)heteroalkynyl, optionally substituted ($C_1$-$C_6$)cycloalkyl, optionally substituted ($C_1$-$C_6$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, $R^{13}$, $R^{16}$-$R^{17}$, and $R^{20}$-$R^{50}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 2 carbon atoms.

In another embodiment, the disclosure provides a framework comprising one or more cores having the general structure of Formula V(a):

V(a)

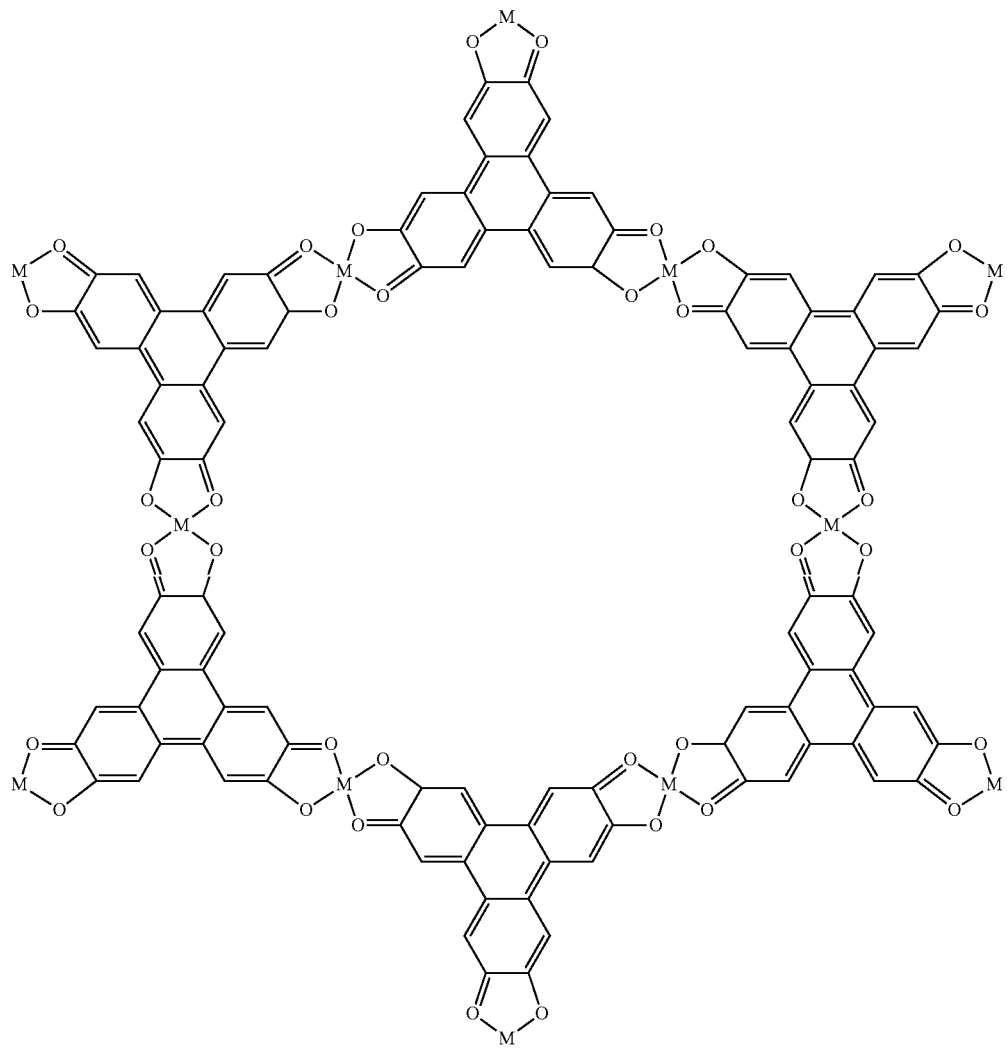

wherein, M is each individually a metal, metal ion, or metal containing complex.

In a further embodiment, the disclosure provides a framework comprising one or more cores having the general structure of Formula VI:

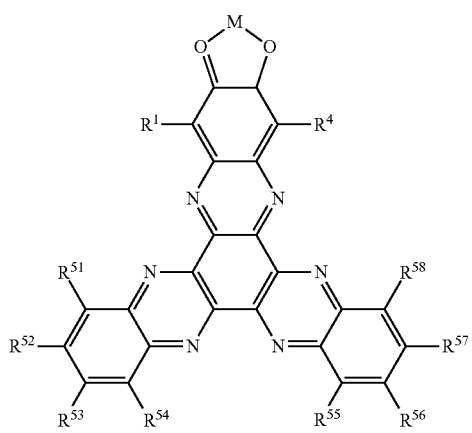

(VI)

wherein M is each individually a metal, metal ion, or metal containing complex; $R^1$, $R^4$, and $R^{51}$-$R^{58}$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, and optionally substituted ($C_1$-$C_5$)heteroalkynyl.

In another embodiment, the disclosure provides a framework comprising one or more cores having the general structure of Formula VI(a):

VI(a)

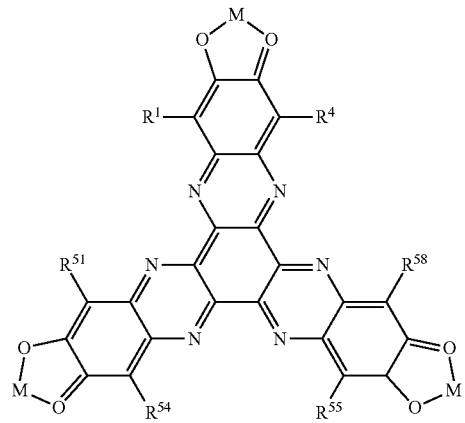

wherein M is each individually a metal, metal ion, or metal containing complex; $R^1$, $R^4$, $R^{51}$, $R^{54}$-$R^{55}$, and $R^{58}$ are each individually selected from the group comprising H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, and optionally substituted ($C_1$-$C_5$)heteroalkynyl.

In a further embodiment, the disclosure provides a framework comprising one or more cores having the general structure of Formula VI(b):

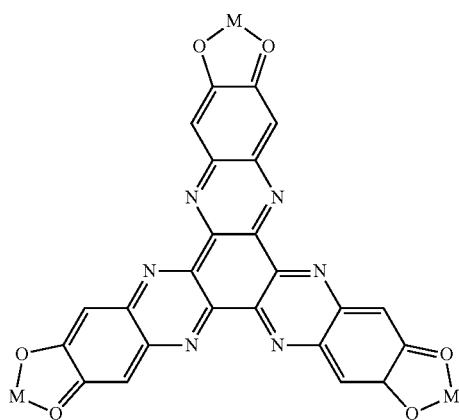

VI(b)

wherein, M is each individually a metal, metal ion, or metal containing complex.

In a certain embodiment, a CAT framework of the disclosure comprises the generalized core structure of:

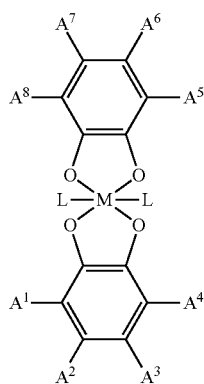

wherein, M is a metal that is linked to two linking moieties through catecholate-based linking clusters. Repeating cores above provide a CAT framework of the disclosure.

In a further embodiment, a CAT framework comprises one or more cores having the structure of:

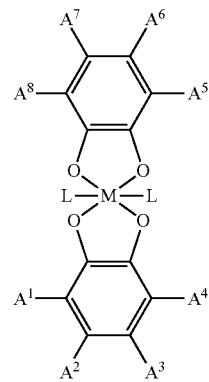

wherein, M is a metal, or metal ion; L is an auxiliary guest molecule or anion; $A^1$-$A^8$ are each individually selected from the group comprising a H, ($C_1$-$C_{20}$)alkyl, ($C_1$-$C_{20}$)cylcoalkyl, aryl, ($C_1$-$C_{19}$)heteroalkyl, and heterocycle group; and wherein a multidentate functional group can be covalently bound to one or more of $A^1$-$A^8$. Examples of such multidentate functional groups used to make the CAT frameworks described herein, include, but are not limited to, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(R_9SH)_2$, $C(R_9SH)_3$, $CH(R_9NH_2)_2$, $C(R_9NH_2)_3$, $CH(R_9OH)_2$, $C(R_9OH)_3$, $CH(R_9CN)_2$, and $C(R_9CN)_3$, wherein $R_9$ is an alkyl group having from 1 to 5 carbon atoms, or an aryl group consisting of 1 to 2 phenyl rings. It should also be further understood that the ligands possessing multidentate functional groups bring with them corresponding counter cations, such as $H^+$, $Na^+$, $K^+$, $Mg_2^+$, $Ca_2^+$, $Sr_2^+$, ammonium ion, alkyl substituted ammonium ions, and aryl substituted ammonium ions, or counter anions, such as $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^-$, $SO_3^-$, $PO_3^-$, $CO_3^-$, $PF_6^-$ and organic counter ions such as acetate $CH_3CO_2^-$, triflates, and $CF_3SO_3^-$.

In one particular embodiment, a CAT framework comprises one or more cores having the structure of:

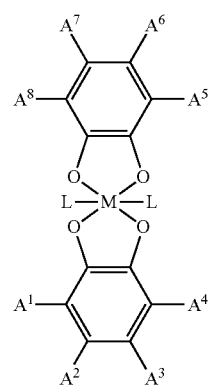

wherein, M is a metal, or metal ion; L is an auxiliary guest molecule or anion; $A^1$-$A^8$ comprise a non-sterically hindering electron donating group that does not interfere with M; and wherein a multidentate functional group can be covalently bound to one or more of $A^1$-$A^8$.

In yet another embodiment, a CAT framework comprises one or more cores having the structure of:

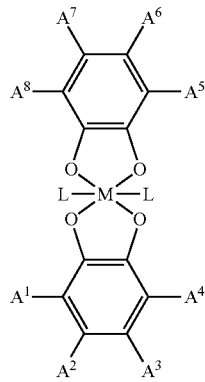

wherein, M is a metal, or metal ion; L is an auxiliary guest molecule or anion; $A^1$-$A^8$ are each individually selected from the group comprising a H, ($C_1$-$C_{20}$)alkyl, ($C_1$-$C_{20}$)cylcoalkyl, aryl, ($C_1$-$C_{19}$)heteroalkyl, and heterocycle group; wherein two multidentate functional groups can be covalently bound to one or more of $A^1$-$A^8$, and wherein at least one multidentate functional group is selected to interact with a particular gas or substrate.

Metals, their associated ions or complexes that can be used in the synthesis of CAT frameworks disclosed herein are selected from the group comprising alkali metals, alkaline earth metals, transition metals, lanthanides, actinoids, metalloids, and post transition metals. Metal, metal ions, and/or metal containing complexes can be introduced into open CAT frameworks of the disclosure, via forming complexes with one or more linking clusters in a framework or by simple ion exchange. Therefore, it is reasonable to assume that any metal, metal ions, and/or metal containing complexes disclosed herein can be introduced. Moreover, post synthesis of a CAT framework of the disclosure, metals, metal ions, and/or metal containing complexes may be exchanged by commonly known techniques, and/or additional metal ions can be added to a CAT framework disclosed herein by forming coordination complexes with linking clusters arising from post framework reactants.

In a particular embodiment, one or more metals, metal ions, and/or metal containing complexes that can be used in the (1) synthesis of a CAT framework of the disclosure, (2) exchanged post synthesis of a CAT framework disclosed herein, and/or (3) added to a CAT framework of the disclosure by forming coordination complexes with one or more post framework reactant linking clusters, including, but are not limited to, alkali metals, alkaline earth metals, transition metals, lanthanides, actinoids, metalloids, and post transition metals.

In a certain embodiment, one or more metals and/or metal ions, that can be used in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$, and any combination thereof, including any complexes which contain the metals or metal ions listed above, as well as any corresponding metal salt counter-anions.

In a further embodiment, one or more metal and/or metal ions that can be used in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, include, but are not limited to, $Li^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Ce^{4+}$, $Ce^{3+}$, $Ce^{2+}$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, and combinations thereof, including any complexes which contain the metals or metal ions listed above, as well as any corresponding metal salt counter-anions.

In yet a further embodiment, one or more metal ions that can be used in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, include, but are not limited to, $Li^+$, $Mg^{2+}$, $Ca^{2+}$, $Ba^{2+}$, $Zr^{4+}$, $Zr^{3+}$, $Zr^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $W^{6+}$, $W^{5+}$, $W^{4+}$, $W^{3+}$, $W^{2+}$, $W^+$, $V^{5+}$, $V^{4+}$, $V^{3+}$, $V^{2+}$, $Mn^{6+}$, $Mn^{5+}$, $Mn^{4+}$, $Mn^{3+}$, $Mn^{2+}$, $Mn^+$, $Fe^{6+}$, $Fe^{4+}$, $Fe^{3+}$, $Fe^{2+}$, $Fe^+$, $Fe$, $Co^{5+}$, $Co^{4+}$, $Co^{3+}$, $Co^{2+}$, $Co^+$, $Ni^{3+}$, $Ni^{2+}$, $Ni^+$, $Ni$, $Cu^{4+}$, $Cu^{3+}$, $Cu^{2+}$, $Cu^+$, $Zn^{2+}$, $Zn^+$, $Zn$, $Pd^{6+}$, $Pd^{4+}$, $Pd^{2+}$, $Pd^+$, $Cd^{2+}$, $Cd^+$, $Ce^{4+}$, $Ce^{3+}$, $Ce^{2+}$, and any combination thereof, including any complexes which contain the metal ions listed above, as well as any corresponding metal salt counter-anions.

In a certain embodiment, one or more metal ions used in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, include, but are not limited to, $Li^+$, $Mg^{2+}$, $Ca^{2+}$, $Ba^{2+}$, $Zr^{4+}$, $Zr^{3+}$, $Zr^{2+}$, $Mn^{3+}$, $Mn^{2+}$, $Mn^+$, $Fe^{3+}$, $Fe^{2+}$, $Fe^+$, $Ni^{3+}$, $Ni^{2+}$, $Ni^+$, $Ni$, $Cu^{4+}$, $Cu^{3+}$, $Cu^{2+}$, $Cu^+$, $V^{5+}$, $V^{4+}$, $V^{3+}$, $V^{2+}$, $Co^{3+}$, $Co^{2+}$, $Co^+$, $Zn^{2+}$, $Zn^+$, $Ce^{4+}$, $Ce^{3+}$, and $Ce^{2+}$.

In a further embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, are divalent metal ions.

In another embodiment, one or more metal ions in (1) synthesis of a CAT framework of the disclosure, (2) exchanged post synthesis of a CAT framework disclosed herein, and/or (3) added to a CAT framework of the disclosure by forming coordination complexes with post framework reactant linking clusters, is a divalent metal ion selected from the group comprising $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

In another embodiment, one or more metal ions in (1) synthesis of a CAT framework of the disclosure, (2) exchanged post synthesis of a CAT framework disclosed herein, and/or (3) added to a CAT framework of the disclosure by forming coordination complexes with post framework reactant linking clusters, is a divalent metal ion selected from the group comprising $Mg^{2+}$, $Ba^{2+}$, $Ca^{2+}$, $V^{2+}$, $Cu^{2+}$, $Ce^{2+}$, $Zr^{2+}$, $Ni^{2+}$, $Ce^{2+}$, and $Zn^{2+}$.

In a further embodiment, the metal ion used in the synthesis of a CAT framework of the disclosure is a divalent metal ion selected from the group comprising $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $B^{2+}$, $Al^{2+}$, $Ga^{2+}$, $Si^{2+}$, $Sn^{2+}$, $Pb^{2+}$, $Hg^{2+}$, $As^{2+}$, $Te^{2+}$, $La^{2+}$, $Ce^{2+}$, $Pr^{2+}$, $Sm^{2+}$, $Gd^{2+}$, $Nd^{2+}$, $Db^{2+}$, $Tb^{2+}$, $Tm^{2+}$ and $Yb^{2+}$.

In yet a further embodiment, the metal ion used in the synthesis of a CAT framework disclosed herein is a metal ion selected from the group comprising $Li^+$, $Mg^{2+}$, $Ca^{2+}$, $Sr^{2+}$, $Ba^{2+}$, $Zr^{2+}$, $V^{2+}$, $Sc^{2+}$, $Mn^{2+}$, $Fe^{2+}$, $Ni^{2+}$, $Pd^{2+}$, $Pt^{2+}$, $Cu^{2+}$, $Co^{2+}$, $Ag^{2+}$, $Hg^{2+}$, $Pb^{2+}$, $Zn^{2+}$, and $Cd^{2+}$.

In a certain embodiment, the metal ion used in the synthesis of a CAT framework of the disclosure is a metal ion selected from the group comprising $Li^+$, $Mg^{2+}$, $Mn^{2+}$, $Ba^{2+}$, $Ca^{2+}$, $V^{2+}$, $Cu^{2+}$, $Ce^{2+}$, $Zr^{2+}$, $Ni_{2+}$, $Co^{2+}$, and $Zn^{2+}$.

Linking moiety linking clusters and/or post frameworks reactants linking clusters can be selected based on Hard Soft Acid Base theory (HSAB) to optimize the interaction between the linking clusters and/or post framework reactants and a metal or metal ion disclosed herein. In certain cases linking clusters and/or metal or metal ions are selected to be a hard acid and hard base, wherein linking clusters, post frameworks reactants, and/or metals or metal ions will have the following characteristics: small atomic/ionic radius, high oxidation state, low polarizability, hard electronegativity (bases), highest-occupied molecular orbitals (HOMO) of the hard base is low in energy, and lowest unoccupied molecular orbitals (LUMO) of the hard acid are of high energy. Generally hard base linking clusters contain oxygen. Typical hard metal and metal ions include alkali metals, and transition metals such as Fe, Cr, and V in higher oxidation states. In other cases linking clusters and/or metal or metal ions are selected to be a soft acid and a soft base, wherein linking clusters and/or metal or metal ions will have the following characteristics: large atomic/ionic radius, low or zero oxidation state, high polarizability, low electronegativity, soft bases have HOMO of higher energy than hard bases, and soft acids have LUMO of lower energy than hard acids. Generally soft base linking clusters contain sulfur, phosphorous, and larger halides. In other cases linking clusters and/or metal or metal ions are selected to be a borderline acid and a borderline base. In certain cases, linking clusters and/or metal or metal ions are selected so that they are hard and soft, hard and borderline, or borderline and soft.

In one embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, and/or metal or metal ions, are HSAB hard metal and/or metal ions. In another embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, are HSAB soft metal and/or metal ions. In yet another embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, are HSAB borderline metal and/or metal ions. In the case that there is a plurality of metal and/or metal ions used in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, then there can be any combination of hard, soft and borderline metals and/or metal ions that can be used in or attached to a CAT framework disclose herein.

In a further embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, have a coordination number selected from the following: 2, 4, 6, and 8. In another embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, have a coordination number of either 4 or 6. In yet another embodiment, one or more metal ions in the (1) synthesis of a CAT framework of the disclosure, (2) exchanged post synthesis of a CAT framework disclosed herein, and/or (3) added to a CAT framework of the disclosure by forming coordination complexes with post framework reactant linking clusters, have a coordination number of 6.

In a further embodiment, one or more metal and/or metal ions used in the synthesis of a CAT framework disclosed herein can be coordinated with one or more linking clusters so that the coordination complex has a molecular geometry including, but not limited to, trigonal planar, tetrahedral, square planar, trigonal bipyramidal, square pyramidal, octahedral, trigonal prismatic, pentagonal bipyramidal, paddlewheel and square antiprismatic. In a further embodiment, a metal or metal ion used in the synthesis of a CAT framework disclosed herein can form a coordination complex that has a molecular geometry including, but not limited to, tetrahedral, paddle-wheel and octahedral molecular geometry. In a further embodiment, a metal and/or metal ion used in the synthesis of a CAT disclosed herein can form a coordination complex that has octahedral molecular geometry. In another embodiment, a coordination complex with octahedral geometry can exist as various isomers depending on whether two or more types of linking clusters are coordinated to a metal ion. Examples of such isomers that can result, include, but are not limited to, cis, trans, fac, mer, and any combination thereof for coordination complexes that have three or more different linking clusters. In a yet further embodiment, a coordination complex disclosed herein may have chirality. In another embodiment, a coordination complex disclosed herein may not have chirality.

It is understood that metal containing complexes bring with them corresponding counter cations, such as $H^+$, $Na^+$, $K^+$, $Mg_2^+$, $Ca_2^+$, $Sr_2^+$, ammonium ion, alkyl substituted ammonium ions, and aryl substituted ammonium ions, or counter anions, such as $F^-$, $Cr^-$, $Br^-$, $ClO^-$, $ClO_2^-$, $ClO_3^-$, $ClO_4^-$, $OH^-$, $NO_3^-$, $NO_2^-$, $SO_4^=$, $SO_3^=$, $PO_3^-$, $CO_3^=$, $PF_6^-$ and organic counter ions such as acetate $CH_3CO_2^-$, triflates, and $CF_3SO_3^-$.

In a certain embodiment, a CAT framework of the disclosure comprises one or more cores comprising one or more linking moieties of structural Formula VII:

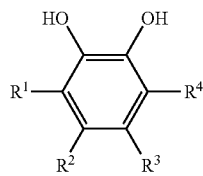

(VII)

$R^1$-$R^4$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$-$R^4$ comprises one or more covalently bound functional groups that have denticity.

In a certain embodiment, a CAT framework of the disclosure comprises one or more cores comprising one or more linking moieties of structural Formula VII:

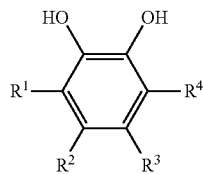

(VII)

wherein $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula VII:

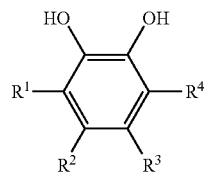

(VII)

wherein $R^1$-$R^4$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, mixed ring system, and catechol; wherein at least one of $R^1$-$R^4$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)^2$, $C(X^1OH)_3$, $CH_2(X^1(OH)^2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula VII(a):

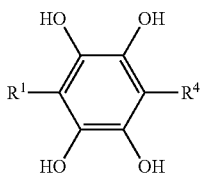

VII(a)

wherein R¹ and R⁴ are each individually selected from the group comprising H, D, optionally substituted FG, optionally substituted $(C_1-C_6)$alkyl, optionally substituted $(C_1-C_5)$heteroalkyl, optionally substituted $(C_1-C_6)$alkenyl, optionally substituted $(C_1-C_5)$heteroalkenyl, optionally substituted $(C_1-C_6)$alkynyl, and optionally substituted $(C_1-C_5)$heteroalkynyl.

In a certain embodiment, a CAT framework of the disclosure comprises one or more cores comprising one or more linking moieties of structural Formula VII(b):

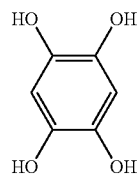

(VII(b))

In a certain embodiment, a CAT framework of the disclosure comprises one or more cores comprising one or more linking moieties of structural Formula VIII:

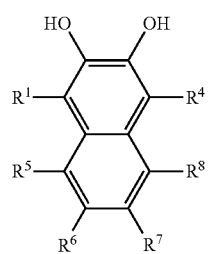

(VIII)

wherein R¹, R⁴, and R⁵-R⁸ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of R¹, R⁴, and R⁵-R⁸ comprises one or more covalently bound functional groups that have denticity.

In a certain embodiment, a CAT framework of the disclosure comprises one or more cores comprising one or more linking moieties of structural Formula VIII:

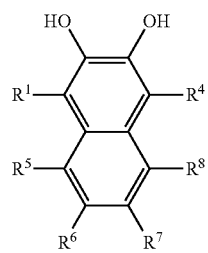

(VIII)

R¹, R⁴, and R⁵-R⁸ are independently selected from the group comprising H, D, optionally substituted FG, optionally substituted $(C_1-C_{20})$alkyl, optionally substituted $(C_1-C_{19})$heteroalkyl, optionally substituted $(C_1-C_{20})$alkenyl, optionally substituted $(C_1-C_{19})$heteroalkenyl, optionally substituted $(C_1-C_{20})$alkynyl, optionally substituted $(C_1-C_{19})$heteroalkynyl, optionally substituted $(C_1-C_{20})$cycloalkyl, optionally substituted $(C_1-C_{20})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of R¹, R⁴, and R⁵-R⁸ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula VIII(a):

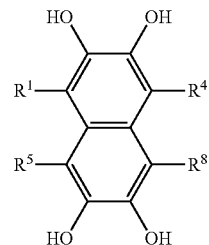

(VIII(a))

wherein R¹, R⁴-R⁵, and R⁸ are each individually selected from the group comprising H, D, optionally substituted FG, optionally substituted $(C_1-C_6)$alkyl, optionally substituted $(C_1-C_5)$heteroalkyl, optionally substituted $(C_1-C_6)$alkenyl, optionally substituted $(C_1-C_5)$heteroalkenyl, optionally substituted $(C_1-C_6)$alkynyl, and optionally substituted $(C_1-C_5)$heteroalkynyl.

In a certain embodiment, a CAT framework of the disclosure comprises one or more cores comprising one or more linking moieties of structural Formula VIII(b):

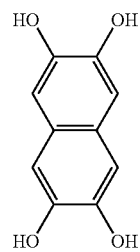

(VIII(b))

In a certain embodiment, a CAT framework of the disclosure comprises one or more cores comprising one or more linking moieties of structural Formula IX:

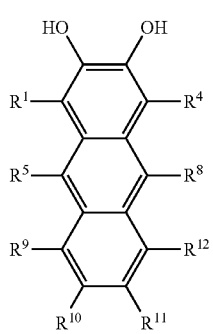

(IX)

wherein $R^1$, $R^4$-$R^5$, and $R^8$-$R^{12}$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$-$R^5$, and $R^8$-$R^{12}$ comprises one or more covalently bound functional groups that have denticity.

In a certain embodiment, a CAT framework of the disclosure comprises one or more cores comprising one or more linking moieties of structural Formula IX:

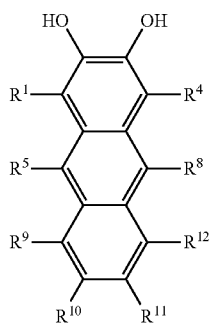

(IX)

wherein $R^1$, $R^4$-$R^5$, and $R^8$-$R^{12}$ are independently selected from the group comprising H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{20})$alkynyl, optionally substituted $(C_1$-$C_{19})$heteroalkynyl, optionally substituted $(C_1$-$C_{20})$cycloalkyl, optionally substituted $(C_1$-$C_{20})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$-$R^5$, and $R^8$-$R^{12}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula IX(a):

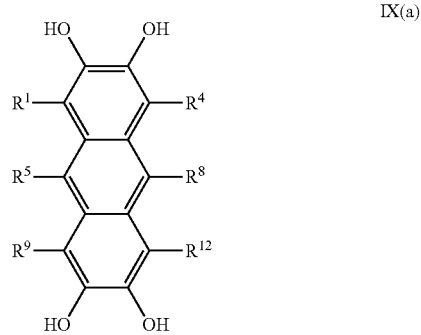

IX(a)

wherein $R^1$, $R^4$-$R^5$, and $R^8$-$R^9$, and $R^{12}$ are each individually selected from the group comprising H, D, optionally substituted FG, optionally substituted $(C_1$-$C_6)$alkyl, optionally substituted $(C_1$-$C_5)$heteroalkyl, optionally substituted $(C_1$-$C_6)$alkenyl, optionally substituted $(C_1$-$C_5)$heteroalkenyl, optionally substituted $(C_1$-$C_6)$alkynyl, and optionally substituted $(C_1$-$C_5)$heteroalkynyl.

In a certain embodiment, a CAT framework of the disclosure comprises one or more cores comprising one or more linking moieties of structural Formula IX(b):

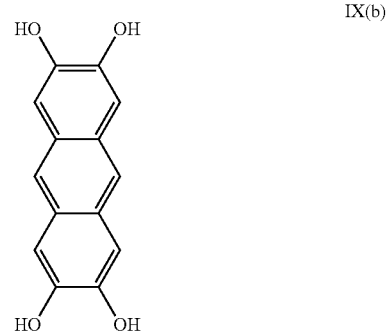 [SMILES: Oc1cc2cc3cc(O)c(O)cc3cc2cc1O]

IX(b)

In a certain embodiment, a CAT framework of the disclosure comprises one or more cores comprising one or more linking moieties of structural Formula X:

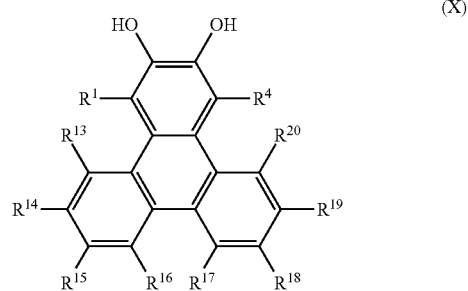

(X)

wherein $R^1$, $R^4$, and $R^{13}$-$R^{20}$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$, and $R^{13}$-$R^{20}$ comprises one or more covalently bound functional groups that have denticity.

In a certain embodiment, a CAT framework of the disclosure comprises one or more cores comprising one or more linking moieties of structural Formula X:

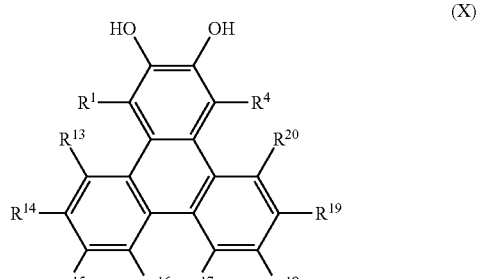

(X)

$R^1$, $R^4$, and $R^{13}$-$R^{20}$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$)cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, and $R^{13}$-$R^{20}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula X(a):

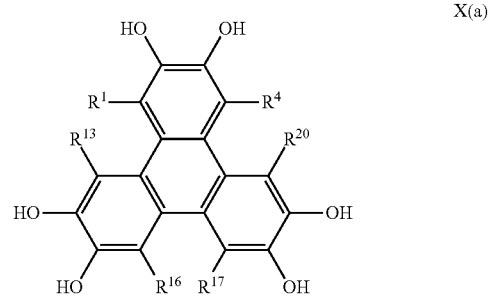

X(a)

wherein, $R^1$, $R^4$, $R^{13}$, $R^{16}$-$R^{17}$, and $R^{20}$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, and optionally substituted ($C_1$-$C_5$)heteroalkynyl.

In a certain embodiment, a CAT framework of the disclosure comprises one or more cores comprising one or more linking moieties of structural Formula X(b):

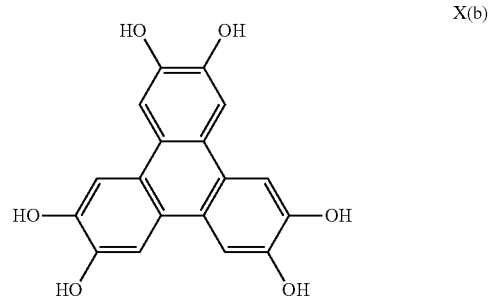 [SMILES: Oc1cc2c3cc(O)c(O)cc3c3cc(O)c(O)cc3c2cc1O]

X(b)

In a certain embodiment, a CAT framework of the disclosure comprises one or more cores comprising one or more linking moieties of structural Formula XI:

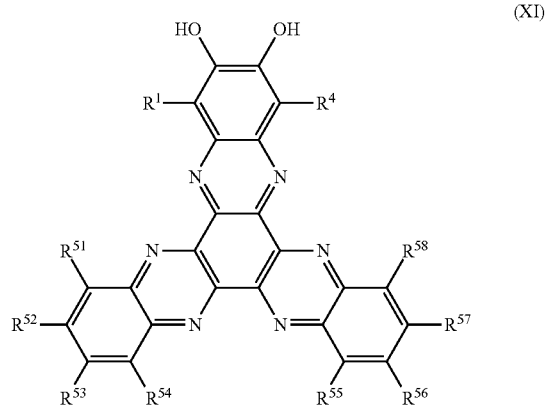

(XI)

wherein $R^1$, $R^4$, and $R^{51}$-$R^{58}$ are independently selected from the group comprising H, D, optionally substituted FG, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted or unsubstituted rings selected from the group comprising cycloalkyl, cycloalkenyl, heterocycle, aryl and mixed ring system; and wherein at least one of $R^1$, $R^4$, and $R^{13}$-$R^{20}$ comprises one or more covalently bound functional groups that have denticity.

In a certain embodiment, a CAT framework of the disclosure comprises one or more cores comprising one or more linking moieties of structural Formula XI:

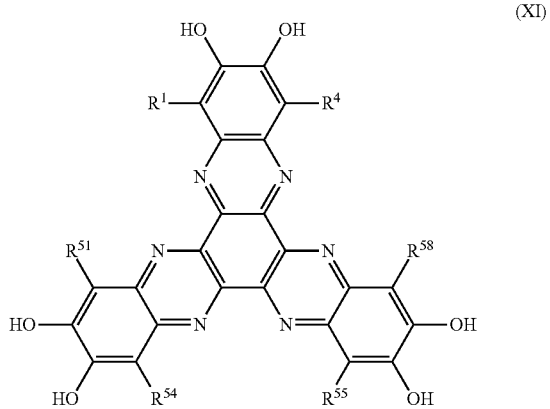

(XI)

wherein $R^1$, $R^4$, $R^{51}$, $R^{54}$-$R^{55}$, and $R^{58}$ are independently selected from the group comprising H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{20}$)alkynyl, optionally substituted ($C_1$-$C_{19}$)heteroalkynyl, optionally substituted ($C_1$-$C_{20}$) cycloalkyl, optionally substituted ($C_1$-$C_{20}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system; wherein at least one of $R^1$, $R^4$, $R^{51}$, $R^{54}$-$R^{55}$, and $R^{58}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 5 carbon atoms, or an aryl group consisting of 1 to 2 phenyl rings.

In a certain embodiment, a CAT framework of the disclosure comprises one or more cores comprising one or more linking moieties of structural Formula XI(b):

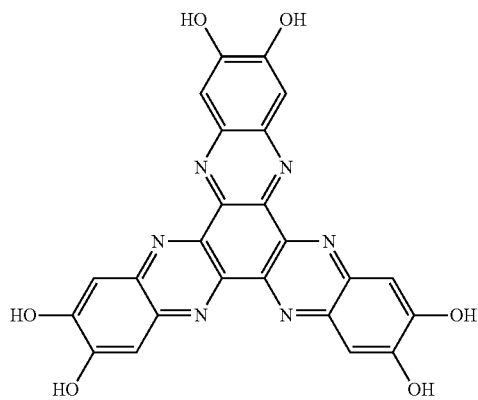

XI(b)

The preparation of CAT frameworks of the disclosure can be carried out in either an aqueous or non-aqueous solvent system. The solvent may be polar or non-polar, or a combination thereof, as the case may be. The reaction mixture or suspension comprises a solvent system, linking moiety or moieties, and a metal or a metal/salt complex. The reaction solution, mixture or suspension may further contain a templating agent, catalyst, or combination thereof. The reaction mixture may be heated at an elevated temperature or maintained at ambient temperature, depending on the reaction components.

Examples of non-aqueous solvents that can be used in a reaction to make a CAT framework disclosed herein and/or used as non-aqueous solvent for a post-synthesized CAT framework reaction, include, but are not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-petanol, and 2-pentanol; amide based solvents, such as, dimethylacetamide, dimethylformamide (DMF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, cholorbenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrchloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phosphorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; carboxylic acid based solvents, such as formic acid, acetic acid, chloracetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, an aqueous solvent used as the solvent system in synthesizing a CAT framework disclosed herein has a pH less than 7. In another embodiment, an aqueous solvent used as the solvent system in synthesizing a CAT framework disclosed herein has a pH greater than 7. In another embodiment, an aqueous solvent used as the solvent system in synthesizing a CAT framework disclosed herein has a pH at or about 7. In yet a further embodiment, a solvent system used to synthesize a CAT framework disclosed herein comprises water. In a certain embodiment, the aqueous solvent system used to synthesize a CAT framework disclosed herein further comprises a dipolar aprotic solvent. In a further embodiment, the aqueous solvent system used to synthesize a CAT framework disclosed herein further comprises 1-methyl-2-pyrrolidone (NMP).

Those skilled in the art will be readily able to determine an appropriate solvent or appropriate mixture of solvents based on the starting reactants and/or where the choice of a particular solvent(s) is not believed to be crucial in obtaining the materials of the disclosure.

Templating agents can be used in the methods of the disclosure. Templating agents employed in the disclosure are added to the reaction mixture for the purpose of occupying the pores in the resulting CAT frameworks disclosed herein. In some variations of the disclosure, space-filling agents, absorbed or adsorbed chemical species and guest species increase the surface area of a CAT framework disclosed herein. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

In certain embodiments templating agents are used with the methods disclosed herein, and in other embodiments templating agents are not used with the methods disclosed herein.

Crystallization of CAT frameworks of the disclosure can be carried out by maintaining the solution, mixture, or suspension at ambient temperature or by maintaining the solution, mixture, or suspension at an elevated temperature; adding a diluted base to the solution; diffusing the diluted base throughout the solution; and/or transferring the solution to a closed vessel and heating to a predetermined temperature.

In a certain embodiment, crystallization of CAT frameworks of the disclosure can be improved by adding an additive that promotes nucleation.

In another embodiment, the solution, mixture or suspension is maintained at ambient temperature to allow for crystallization. In yet another embodiment, the solution, mixture, or suspension is heated at an elevated temperature to allow for crystallization. In a certain embodiment, the solution, mixture, or suspension is heated at an elevated temperature up to 100° C. to allow for crystallization. In a yet further embodiment, crystallization of the frameworks can be achieved by heating the frameworks from 75° C. to 90° C. for 1 to 72 hours. In a further embodiment, activated frameworks can be generated by calcination or by heating under a dynamic vacuum atmosphere.

The CAT frameworks of the disclosure may be generated by first utilizing a plurality of linking moieties having different functional groups, wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups of CAT frameworks disclosed herein.

After CAT frameworks of the disclosure are synthesized, the CAT frameworks may be further modified by reacting with one or more post framework reactants that may or may not have denticity. In a certain embodiment, the CAT frameworks as-synthesized are not reacted with a post framework reactant. In another embodiment, the CAT frameworks as-synthesized are reacted with at least one post framework reactant. In yet another embodiment, the CAT frameworks as-synthesized are reacted with at least two post framework reactants. In a further embodiment, the CAT frameworks as-synthesized are reacted with at least one post framework reactant that will result in adding denticity to the framework.

The disclosure provides for chemical reactions that modify, substitute, or eliminate a functional group post-synthesis of a CAT framework disclosed herein with a post framework. These chemical reactions may use one or more similar or divergent chemical reaction mechanisms depending on the type of functional group and/or post framework reactant used in the reaction. Examples of chemical reaction include, but are not limited to, radical-based, unimolecular nuclephilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericyclic, electrocylic, rearrangement, carbene, carbenoid, cross coupling, and degradation.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, a post framework reactant adds at least one effect to a CAT framework of the disclosure including, but not limited to, modulating the gas storage ability of a CAT framework; modulating the sorption properties of a CAT framework; modulating the pore size of a CAT framework; modulating the catalytic activity of a CAT framework; modulating the conductivity of a CAT framework; and modulating the sensitivity of a CAT framework to the presence of an analyte of interest. In a further embodiment, a post framework reactant adds at least two effects to a CAT framework of the disclosure including, but not limited to, modulating the gas storage ability of a CAT framework; modulating the sorption properties of a CAT framework; modulating the pore size of a CAT framework; modulating the catalytic activity of a CAT framework; modulating the conductivity of a CAT framework; and modulating the sensitivity of a CAT framework to the presence of an analyte of interest.

In one embodiment, a post framework reactant can be a saturated or unsaturated heterocycle.

In another embodiment, a post framework reactant has 1-20 carbons with functional groups including atoms such as N, S, and O.

In yet another embodiment, a post framework reactant is selected to modulate the size of the pores of a CAT framework disclosed herein.

In another embodiment, a post framework reactant is selected to increase the hydrophobicity of a CAT framework disclosed herein.

In yet another embodiment, a post framework reactant is selected to modulate gas separation of a CAT framework disclosed herein. In a certain embodiment, a post framework reactant creates an electric dipole moment on the surface of a CAT framework of the disclosure when it chelates a metal ion.

In a further embodiment, a post framework reactant is selected to modulate the gas sorption properties of a CAT framework of the disclosure. In another embodiment, a post framework reactant is selected to promote or increase greenhouse gas sorption of a CAT framework disclosed herein. In another embodiment, a post framework reactant is selected to promote or increase hydrocarbon gas sorption of a CAT framework of the disclosure.

In yet a further embodiment, a post framework reactant is selected to increase or add catalytic efficiency to a CAT framework disclosed herein.

In another embodiment, a post framework reactant is selected so that organometallic complexes can be tethered to a CAT framework of the disclosure. Such tethered organometallic complexes can be used, for example, as heterogeneous catalysts.

In one embodiment of the disclosure, a gas storage or separation material comprising a CAT framework is provided. Advantageously, the CAT framework includes one or more sites for storing and/or separating gas molecules. Gases that may be stored in the gas storage material of the disclosure include gas molecules which have high electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

The disclosure provides an apparatus and method for separating one or more components from a multi-component gas using a separation system having a feed side and an effluent side separated by a CAT framework of the disclosure. The CAT framework may comprise a column separation format.

In an embodiment of the disclosure, a gas storage material comprising a CAT framework is provided. Gases that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising ammonia, argon, carbon dioxide, carbon monoxide, hydrogen, and combinations thereof. In particularly useful variation, the gas binding material is a carbon dioxide binding material that may be used to separate carbon dioxide from a gaseous mixture.

In an embodiment, a gas separation material comprising one or more CAT frameworks disclosed herein is provided. Advantageously, a CAT framework disclosed herein includes one or more sites for sorption of one or more select gas molecules resulting in separation of these gas molecules from a multicomponent gas. Furthermore, gases that may be separated by one or more CAT frameworks disclosed herein include gas molecules that have available electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising ammonia, argon, carbon dioxide, hydrogen sulfide, carbonyl sulfide, carbon disulfide, mercaptans, carbon monoxide, hydrogen, and combinations thereof. In a particular embodiment, one or more CAT frameworks disclosed herein, can be used to separate one or more component gases from a multi-component gas mixture. In a certain embodiment, one or more CAT frameworks disclosed herein can be used to separate one or more gases with high electron density from a gas mixture. In another embodiment, one or more CAT frameworks disclosed herein can be used to separate one or more gases with high electron density from one or more gases with low electron density.

In a particular embodiment, one or more CAT frameworks disclosed herein are part of a device. In another embodiment, a gas separation device comprises one or more CAT frameworks of the disclosure. In a further embodiment, a gas separation device used to separate one or more component gases from a multi-component gas mixture comprises one or more CAT frameworks disclosed herein. In a certain embodiment, a gas separation device used to separate one or more gases with high electron density from gas mixture comprises one or more CAT frameworks of the disclosure. In a further embodiment, a gas separation device used to separate one or more gases with high electron density from one or more low density gases comprises one or more CAT frameworks of the disclosure.

In a particular embodiment of the disclosure, a gas storage material comprises one more CAT frameworks disclosed herein. A gas that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising ammonia, argon, hydrogen sulfide, carbon dioxide, hydrogen sulfide, carbonyl sulfide, carbon disulfide, mercaptans, carbon monoxide, hydrogen, and combinations thereof. In particularly useful variation, a gas binding material is a carbon dioxide binding material that may be used to separate carbon dioxide from a gaseous mixture. In a particularly useful variation a gas storage material is a hydrogen storage material that is used to store hydrogen ($H_2$). In another particularly useful variation, a gas storage material is a carbon dioxide storage material that may be used to separate carbon dioxide from a gaseous mixture.

In yet a further embodiment, one or more CAT frameworks disclosed herein can be used to separate and/or store one or more gases selected from the group comprising carbon monoxide, carbon dioxide, hydrogen sulfide, carbonyl sulfide, carbon disulfide, mercaptans, nitrous oxide, and ozone.

In another embodiment, one or more CAT frameworks disclosed herein can be used to separate and/or store one or more gases selected from the group comprising carbon monoxide, carbon dioxide, hydrogen sulfide, carbonyl sulfide, carbon disulfide, and mercaptans.

In yet another embodiment, one or more CAT frameworks disclosed herein can be used to separate and/or store carbon monoxide or carbon dioxide.

In a certain embodiment, one or more CAT frameworks disclosed herein can be used to separate and/or store carbon dioxide.

In an embodiment, one or more CAT frameworks disclosed herein can be used to separate and/or store hydrogen.

In another embodiment, a gas storage device comprises one or more CAT frameworks disclosed herein. In a further embodiment, a gas storage device used to adsorb and/or absorb one or more component gases from a multi-component gas mixture comprises one or more CAT frameworks disclosed herein. In a certain embodiment, a gas storage device used to adsorb and/or absorb one or more gases with high electron density from gas mixture comprises one or more CAT frameworks disclosed herein. In a further embodiment, a gas storage device used to adsorb and/or absorb one or more gases with high electron density from one or more low density gases comprises one or more CAT frameworks disclosed herein.

The disclosure also provides methods using CAT frameworks disclosed herein. In a certain embodiment, a method to separate or store one or more gases comprises contacting one or more gases with one or more CAT frameworks disclosed herein. In a further embodiment, a method to separate or store one or more gases from a mixed gas mixture comprises contacting the gas mixture with one or more CAT frameworks disclosed herein. In yet a further embodiment, a method to separate or store one or more high electron density gases from a mixed gas mixture comprises contacting the gas mixture with one or more CAT frameworks disclosed herein. In a certain embodiment, a method to separate or store one or more gases from a fuel gas stream comprises contacting the fuel gas stream with one or more CAT frameworks disclosed herein. In a further embodiment, a method to separate or store one or more acid gases from a natural gas stream comprises contacting the natural gas stream with one or more CAT frameworks disclosed herein. In yet another embodiment, a method to separate or store one or more gases from the exhaust of a combustion engine comprises contacting the exhaust with one or more CAT frameworks disclosed herein. In a certain embodiment, a method to separate or store one or more gases from flue-gas comprises contacting the flue-gas with one or more CAT frameworks disclosed herein.

One or more CAT frameworks of the disclosure can also comprise part of a gas separation and/or a gas storage device. These devices for gas separation and/or gas storage can be used for industrial or nonindustrial purposes, or a combination thereof. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In a particular embodiment, gas separation and/or gas storage devices comprising one or more CAT frameworks of the disclosure can be used to purify fuel gas streams, air, flue-gas emissions, and/or waste emissions from combustion engines. In another embodiment, one or more CAT frameworks disclosed herein can comprise gas separation and/or gas storage devices designed to remove and/or store greenhouse gases, such as carbon dioxide, ozone, nitrous oxide, and fluorocarbons. In a certain embodiment, one or more CAT frameworks disclosed herein can comprise gas separation and/or gas storage devices designed to remove and/or store environmental pollutants, such as formaldehyde, diisocyanates, trichloroethylene, and benzene.

In a certain embodiment, an air purification device comprises one or more CAT frameworks disclosed herein. In a further embodiment, a device used to remove and/or store contaminants from fuel gas comprises one or more CAT frameworks disclosed herein. In yet a further embodiment, a device used to remove and/or store environmentally harmful gases from flue gas emissions comprises one or more CAT frameworks disclosed herein. In a certain embodiment, a device used to remove and/or store environmentally harmful gases or gaseous vapors from air comprises one or more CAT frameworks disclosed herein. In a further embodiment, a device used to remove and/or store greenhouse gases comprises one or more CAT frameworks disclosed herein. In yet a further embodiment, a device for use to prevent buildups of one or more hazardous gases in mining comprises one or more CAT frameworks disclosed herein. In yet a further embodiment, a device for use to remove and/or store one or more gases from emissions of a combustion engine comprises one or more CAT frameworks disclosed herein.

The disclosure provides an apparatus and method for separating one or more components from a multi-component gas using a separation system having a feed side and an effluent side separated by one or more CAT frameworks of the disclosure. The CAT framework may comprise a column separation format.

"Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

The disclosure is particularly suitable for treatment of natural gas streams containing one or more contaminants such as carbon dioxide, hydrogen sulfide, and water vapor. However, the disclosure is not limited to treatment of natural gas. The inventive device and method can be used to separate multi-component gas.

In a certain embodiment, one or more CAT frameworks disclosed herein can be used to separate and/or store one or more gases from a natural gas stream. In another embodiment, one or more CAT frameworks disclosed herein can be used to separate and/or store one or more acid gases from a natural gas stream. In yet another embodiment, one or more CAT frameworks disclosed herein can be used to separate and/or store one or more gases from a town gas stream. In yet another embodiment, one or more CAT frameworks disclosed herein can be used to separate and/or store one or more gases of a biogas stream. In a certain embodiment, one or more CAT frameworks disclosed herein can be used to separate and/or store one or more gases from a syngas stream.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

These materials would be used as standard compounds for sorption instruments, and obtained results would be helpful to improve various industrial plants (i.e. separation or recovery of chemical substance).

In a variation of this embodiment, the gaseous storage site comprises a pore in a CAT framework functionalized with a group having a desired size or charge. In a refinement, this activation involves removing one or more chemical moieties (guest molecules) from the CAT framework. Typically, such guest molecules include species such as water, solvent molecules contained within the CAT framework, and other chemical moieties having electron density available for attachment.

The CAT frameworks used in the embodiments of the disclosure include a plurality of pores for gas adsorption. In one variation, the plurality of pores has a unimodal size distribution. In another variation, the plurality of pores have a multimodal (e.g., bimodal) size distribution.

The disclosure also provides chemical sensors (e.g. resistometric sensors) capable of sensing the presence of an analyte of interest. There is considerable interest in developing sensors that act as analogs of the mammalian olfactory system. However, may such sensor systems are easily contaminated. The porous structures of the disclosure provide a defined interaction area that limits the ability of contaminate to contact a sensor material the passes through the porous structure of the CAT framework of the disclosure. For example, various polymers are used in sensor systems including conductive polymers (e.g., poly(anilines) and polythiophenes), composites of conductive polymers and non-conductive polymers and composites of conductive materials and non-conductive materials. In resistometric systems conductive leads are separated by the conductive material such that a current traverse between the leads and through the sensor material. Upon binding to an analyte, the resistance in the material changes and detectable signal is thus generated. Using the CAT framework of the disclosure, the area surrounding the sensor material is limited and serves as a "filter" to limit contaminants from contacting the sensor material, thus increasing sensor specificity.

The disclosure further provides CAT framework catalyst comprising a CAT framework of the disclosure. The CAT framework of the disclosure, as crystalline material or as molding, can be used in the catalytic conversion of organic molecules. Reactions of this type are, for example, oxidations, the epoxidation of olefins, e.g. the preparation of propylene oxide from propylene and $H_2O_2$ the hydroxylation of aromatics, e.g. the preparation of hydroquinone from phenol and $H_2O_2$ or the conversion of toluene into cresol, the conversion of alkanes into alcohols, aldehydes and acids, isomerization, reactions, for example the conversion of epoxides into aldehydes.

The disclosure further provides CAT framework tunable conductor comprising a CAT framework of the disclosure. With society's insatiable demand for electronics, there is considerable interest to develop low cost and/or high density electronic components. Research has focused on replacing existing inorganic conductors, with three new materials to: 1) organic conductors, 2) organic/inorganic hybrid conductors, and 3) metallic nanoparticles. While organic conductors are very "tunable" they have high resistivities. Organic/inorganic hybrid conductors, while tunable due to the conjugated organic backbone, they also have lower resistivities due to better electron transfer and potentials of their inorganic portions of compound. The disclosure provides for an organic/inorganic hybrid conductors. Specifically, the CATS compounds disclosed herein contain highly conjugated catecholate backbones which allow for electron current transmission across the pi-bond system, as well as metals for efficient electron transfer and potentials. Furthermore the disclosure allows for tuning the conductivities of such CAT compounds by providing the opportunity to prepare materials with different combinations of metals, linking moieties, and multidentate functional groups.

In a certain embodiment, a carbon monoxide detector comprises one or more CAT frameworks of the disclosure. In another embodiment, a combustible gas detector comprises one or more CAT frameworks disclosed herein. In a further embodiment, a device used to measure vehicle emissions comprises one or more CAT frameworks of the disclosure.

The disclosure also provides for supercapacitor device comprising a metal catecholate framework of the disclosure. A supercapacitor typically comprises a pair of electrodes separated by non-conductive porous separator. The space between the electrodes is filled with a liquid electrolyte, which can either be aqueous or non aqueous. One key ways to improve the energy storage of supercapacitors is to optimize the interactions between the electrodes and electrolyte. Double-layer supercapacitors typically consist of high surface area carbon structures that store energy in a polarized liquid layer. The larger the area of solid/liquid interface, the more energy that can be stored. One of the key ways to maximize the area of solid/liquid interface is to optimize pore size. Currently, one of the major drawbacks of carbon frameworks now used in double-layer supercapacitors is poor capacitance. This poor capacitance results from pores in the carbon framework being too large. The disclosure allows for porous CAT (carbon) frameworks that allow for fine tuning of pore size by changing the metal or metal ion. By being able to optimize the pore size, the disclosure allows for an increased wetted carbon surface, while improving volumetric capacitance.

The invention is illustrated in the following examples, which are provided by way of illustration and are not intended to be limiting.

EXAMPLES

The disclosure demonstrates the synthesis, structure and porosity of CATs in which metals Ni, Co, Zn, Zr, Cu, Mn, V, Mg, Ca, Ba, and Ce are linked with catecholate to make porous isoreticular MOFs. The variation in the size of metal ions across the series provides for precise control of pore apertures to a fraction of an angstrom.

The CAT compounds disclosed herein can be prepared by combining catechol or derivative thereof, with a salt of the metal. The preparation of the CAT compounds disclosed herein can be carried out in either an aqueous or non-aqueous system. The solvent may be polar or nonpolar as the case may be. The solvent itself may act as the templating agent, or an additional ligand containing a monodentate functional group can be added. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,2,-dichloroethane, methylene chloride, chloroform, carbon tetrachloride, tetrahydrofuran, dimethylformamide, dimethylsulfoxide, N-methylpyrollidone, dimethylacetamide, diethylformamide, thiophene, pyridine, ethanolamine, triethylamine, ethylenediamine, and the like. Those skilled in the art will be readily able to determine an appropriate solvent based on the starting reactants, and the choice of solvent is not believed to be critical in obtaining the microporous materials of this invention. The crystallizing step is carried out by: leaving the solution at room temperature or in isothermal oven for up to 100° C.; adding a diluted base to the solution to initiate the crystallization; diffusing a diluted base into the solution to initiate the crystallization; and/or transferring the solution to a closed vessel and heating to a predetermined temperature.

The design and synthesis of new porous crystalline materials has been accomplished based on a strategy of assembling metal ions with an organic tri-catecholate link. Solvothermal reactions of 2,3,6,7,10,11-hexahydroxytriphenylene (HHTP) with various metal ions resulted in the formation of novel metal catecholate (CAT) frameworks. The synthesized CAT frameworks exhibited high chemical stability, permanent porosity, remarkable conductivity, and exhibit promising charge storage properties. The discovery of these novel materials pave the way for exploiting future energy and power storage devices based on the novel CAT frameworks disclosed herein.

Scheme II provides an exemplary scheme to make CAT frameworks of the disclosure.

Scheme II

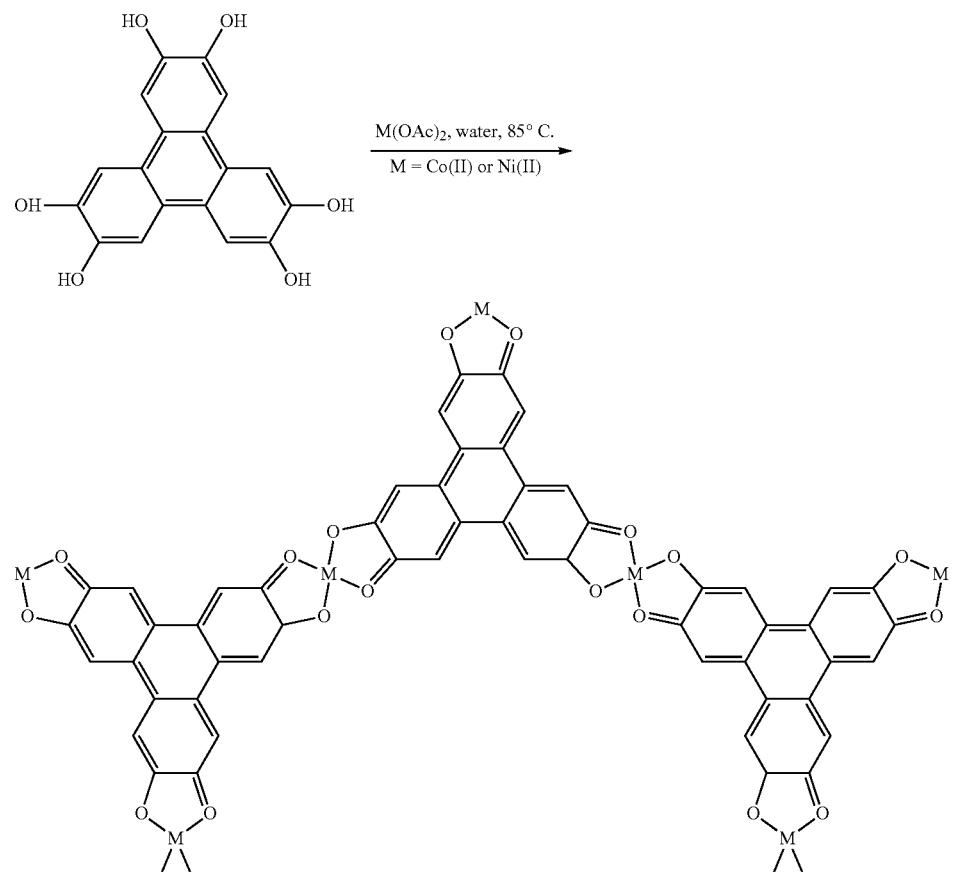

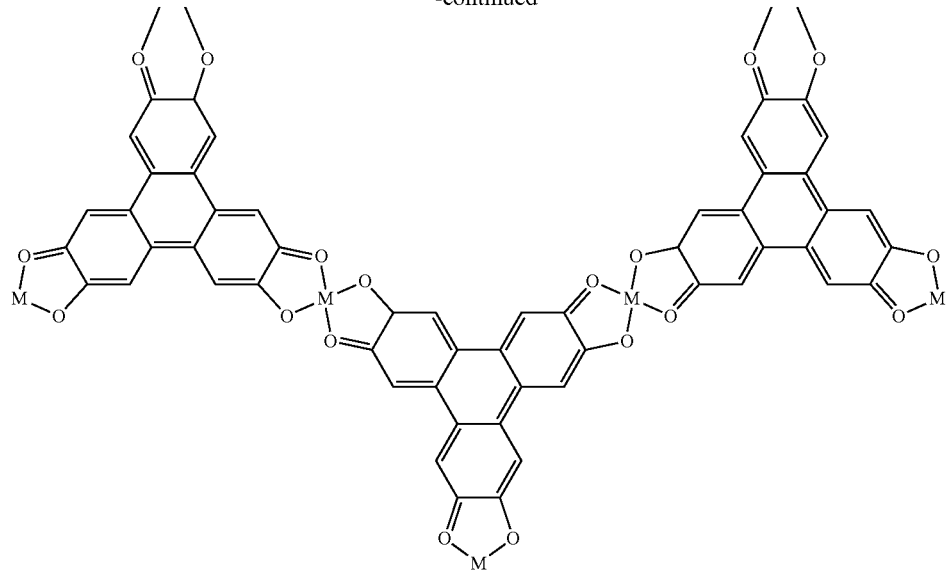

Metal catecholate (CAT) frameworks were prepared by combining 1 equivalent of HHTP with 2 equivalents of the respective metal acetate salt (i.e. $Co(OAc)_2$ and $Ni(OAc)_2$) in an aqueous solution heated at 85° C. for 24 hours. Needle-shaped crystals were obtained and washed with water and solvent-exchanged with acetone for one week. The original size of these crystals was too small to be measured by single crystal x-ray diffractometry; however, by slightly varying the conditions for synthesizing Co-CAT-1 through the addition of 10% of 1-methyl-2-pyrrolidone (NMP), larger crystals suitable for x-ray crystallography were obtained. Based on the obtained data, a space filing model is presented for the synthesized Co-CAT-1 framework in FIG. 1.

Reagents. 2,3,5,6,10,11-Hexahydroxytriphylene (HHTP) was purchased from TCI (9211 N. Harborgate Street, Portland, Oreg. 97203). All metal salts were purchased from Sigma-Aldrich (3050 Spruce St., St. Louis, Mo. 63103). The chemicals were used as received without any further purification.

Synthesis of Ni-CAT-1. In a 20 mL vial, a solid mixture of HHTP (7 mg) and $Ni(OAc)_2 \cdot 4H_2O$ (10 mg) was suspended in deionized water (4.0 mL). The resulting mixture was sonicated for about 2 minutes, capped, and put into an 85° C. oven for 12 hours and then removed to cool slowly at ambient temperature. The resulting dark blue crystals were filtered, washed with water three times (3×4 mL), washed with acetone three times (3×4 mL), and then air dried. (Yield=60% (based on HHTP)). Elemental analysis [$Ni_3(C_{18}H_6O_6)_2 \cdot 6H_2O$]: calc. C, 46.97; H, 2.63; Ni, 19.13. Found C, 41.25; H, 2.60; Ni, 16.43. FTIR (KBr): ν ($cm^{-1}$) 1637.3, 1474.4 (C=O), 1316.5, 1219.8, 1000.8, 848.1, 812.4, 695.3.

Synthesis of Co-CAT-1. In a 4 mL vial, a solid mixture of HHTP (7 mg) and $Co(OAc)_2 \cdot 4H_2O$ (10 mg) was dissolved in 1.5 ml of deionized water. The vial was sealed and sonicated for 30 minutes until the solid was dissolved. To this solution, 0.165 mL of 1-methyl-2-pyrrolidone (NMP) was added dropwise. The vial was then vigorously swirled and sonicated for a short period of time. The resulting dark solution was heated in an isothermal oven at 85° C. for 24 h resulting in dark blue crystals. The reaction mixture was removed to slowly cool at ambient temperature. The resulting crystals were washed with deionized water (3×3 mL), and then, acetone (3×3 mL). Yield: 65% based on HHTP. Elemental analysis [$Co_3(C_{18}H_6O_6)_2 \cdot 11H_2O$]: calc. C, 42.75; H, 3.39; Co, 17.48. Found C, 39.53; H, 3.33; Co, 17.35. FTIR (KBr): ν ($cm^{-1}$) 1637.3, 1474.4 (C=O), 1306.4, 1219.8, 1000.8, 817.5, 690.2, 629.1, 552.8.

Synthesis of Zn-CAT-1. The procedure to make Ni-CAT-1 was followed but substituting a zinc containing salt for the nickel containing salt. (Yield=60% (based on HHTP)). FTIR (KBr): ν($cm^{-1}$) 1637.3, 1464.2 (C=O), 1362.4, 1296.2, 1219.8, 1000.8, 868.5, 812.4, 695.3, 639.3, 557.9.

Synthesis of Zr-CAT-1. The procedure to make Ni-CAT-1 was followed but substituting a zirconium containing salt for the nickel containing salt. (Yield=50% (based on HHTP). FTIR (KBr): ν ($cm^{-1}$) 1627.2, 1454.0 (C=O), 1367.5, 1301.3, 1219.8, 990.7, 868.5, 827.7, 644.4, 547.7.

Synthesis of Cu-CAT-1. The procedure to make Ni-CAT-1 was followed but substituting a copper containing salt for the nickel containing salt. (Yield=55% (based on HHTP)). FTIR (KBr): ν ($cm^{-1}$) 1647.5, 1459.1 (C=O), 1321.6, 1224.9, 990.7, 863.4, 822.6, 695.3, 578.2.

Synthesis of Mn-CAT-1. The procedure to make Ni-CAT-1 was followed but substituting a manganese containing salt for the nickel containing salt. (Yield=20% (based on HHTP)). FTIR (KBr): ν ($cm^{-1}$) 1622.1, 1479.5 (C=O), 1382.7, 1230.0, 868.5.

Synthesis of V-CAT-1. The procedure to make Ni-CAT-1 was followed but substituting a vanadium containing salt for the nickel containing salt. (Yield=22% (based on HHTP)). FTIR (KBr): ν ($cm^{-1}$) 1749.4, 1632.2, 1566.1, 1459.1 (C=O), 1382.7, 1265.6, 1179.1, 985.6, 863.4, 705.5, 644.4, 578.2

Synthesis of Mg-CAT-1. The procedure to make Ni-CAT-1 was followed but substituting a magnesium containing salt for the nickel containing salt. (Yield=50% (based on HHTP)).

Synthesis of Ca-CAT-1. The procedure to make Ni-CAT-1 was followed but substituting a calcium containing salt for the nickel containing salt. (Yield=45% (based on HHTP)).

Synthesis of Ba-CaT-1. The procedure to make Ni-CAT-1 was followed but substituting a barium containing salt for the nickel containing salt. (Yield=42% (based on HHTP)).

Synthesis of Ce-CAT-1. The procedure to make Ni-CAT-1 was followed but substituting a cerium containing salt for the nickel containing salt. (Yield=30% (based on HHTP)).

Solvent Exchange Procedure. The as-synthesized CAT compounds were soaked in water for 1-2 days followed by solvent-exchange with acetone for one week.

Thermal Gravimetric Analysis (TGA). Thermal gravimetric analyses of the CAT frameworks were run on a TA Instruments Q-500 series thermal gravimetric analyzer with samples held in platinum pans under a continuous flow nitrogen atmosphere. Samples were heated at a constant rate of 5° C. min$^{-1}$ during all TGA experiments.

Figure 2:
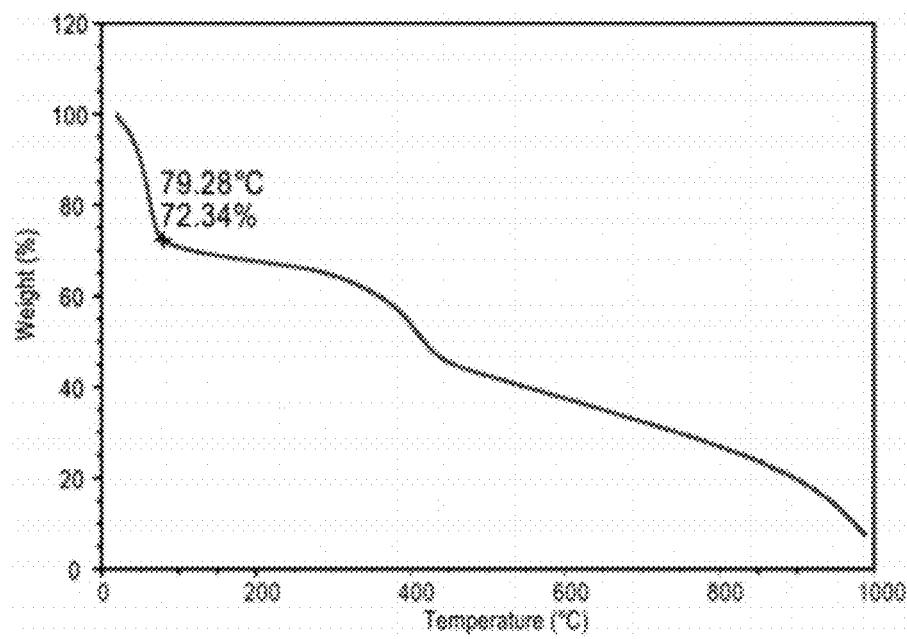
FIG. 2 presents a Thermal Gavimetric analysis plot of Ni-CAT-1 heated at a constant rate of 5° C. $min^{-1}$ under a continuous flow nitrogen atmosphere.

The CAT frameworks thermal stability was probed by thermal gravimetric analysis, which demonstrated a slight weight loss from ambient temperature to 100° C. confirming the hygroscopic nature of these compounds. Above 100° C., no weight loss was observed until 250° C., confirming the high thermal stability of the CAT frameworks. The TGA graph of Ni-CAT-1 is shown in FIG. 2.

Fourier transform infrared spectroscopy. FT-IR spectra were collected on a Nicolate Impact 400 FT-IR Spectrometer. The CATs were mixed with dry potassium bromide and grinded into a solid mixture, and then pressed into a pellet. Data was collected from 96 scans.

Successful removal of unreacted starting materials and organic solvent was further confirmed by $^{13}$C cross-polarization/magic angle spinning nuclear magnetic resonance and Fourier transform infrared spectroscopy.

Powder X-ray diffraction (PXRD) Procedure. PXRD data were collected for the various CAT compounds using a Bruker D8-Discover θ-2θ diffractometer in reflectance Bragg-Brentano geometry. Cu_Kα radiation (λ=1.5406 Å; 1,600 W, 40 kV, 40 mA) was focused using a planar Gobel Mirror riding the Kα line. A 0.6 mm divergence slit was used for all measurements. Diffracted radiation was detected using a Vantec line detector (Bruker AXS) (6° 2θ sampling width) equipped with a Ni monochromator. All samples were ground to ensure mono dispersity in the bulk, and then mounted onto a zero background quartz plate fixed on a sample holder by dropping powders and then leveling the sample surface with a wide-blade spatula. The best counting statistics were achieved by using a 0.02° 2θ step scan from 2-50° or 2-90° with an exposure time of 0.4 s per step. PXRD data collected for metal-CAT-1 complexes are summarized in Table 1, and the tracings are presented in the indicated Figures.

TABLE 1

Summary of PXRD data

Figure 3:
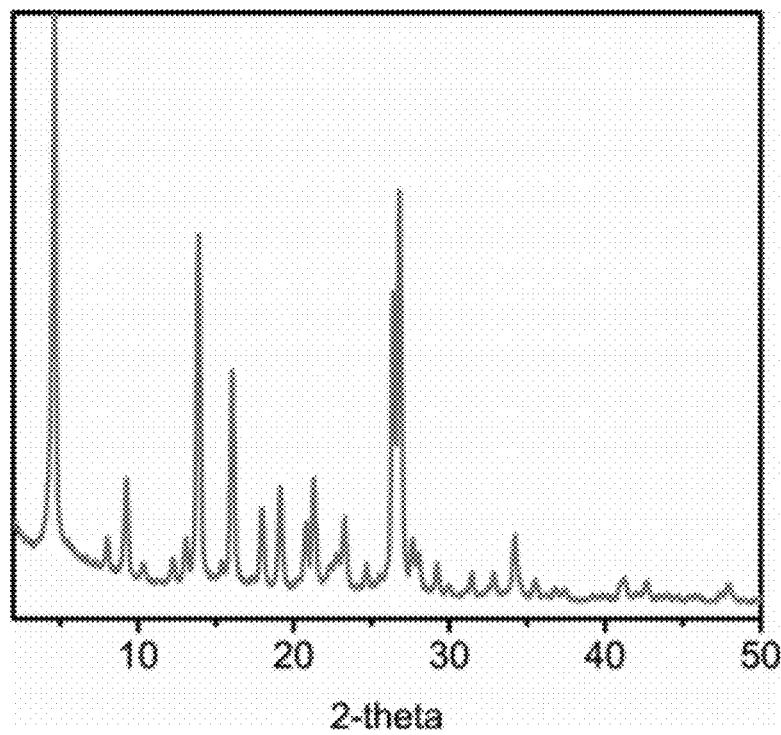
FIG. 3 presents a Powder X-Ray Diffraction Pattern of Ni-CAT-1 using a Bruker D8-Discover θ-20 θ diffractometer in reflectance Bragg-Brentano geometry.
Figure 4:
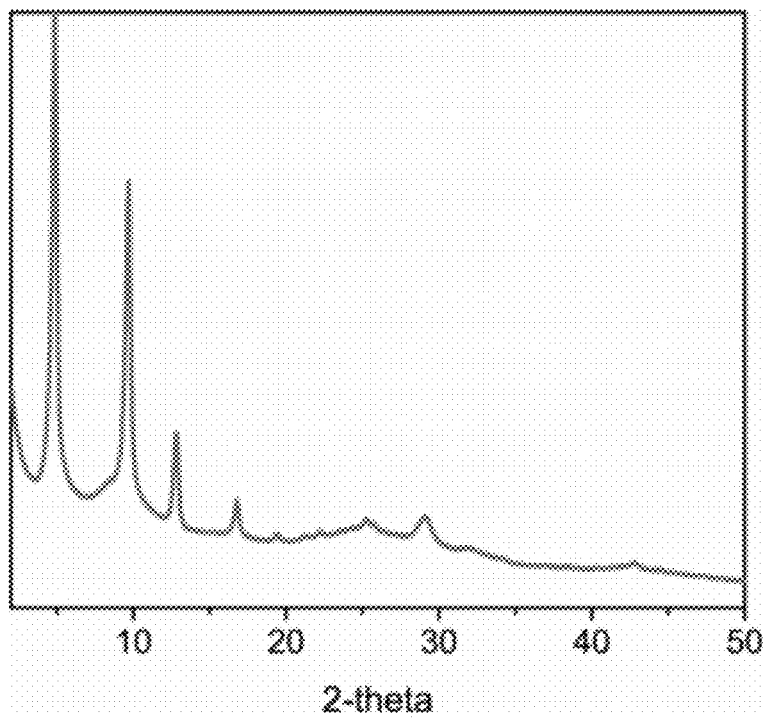
FIG. 4 presents a Powder X-Ray Diffraction Pattern of Zn-CAT-1 using a Bruker D8-Discover θ-20 θ diffractometer in reflectance Bragg-Brentano geometry.
Figure 5:
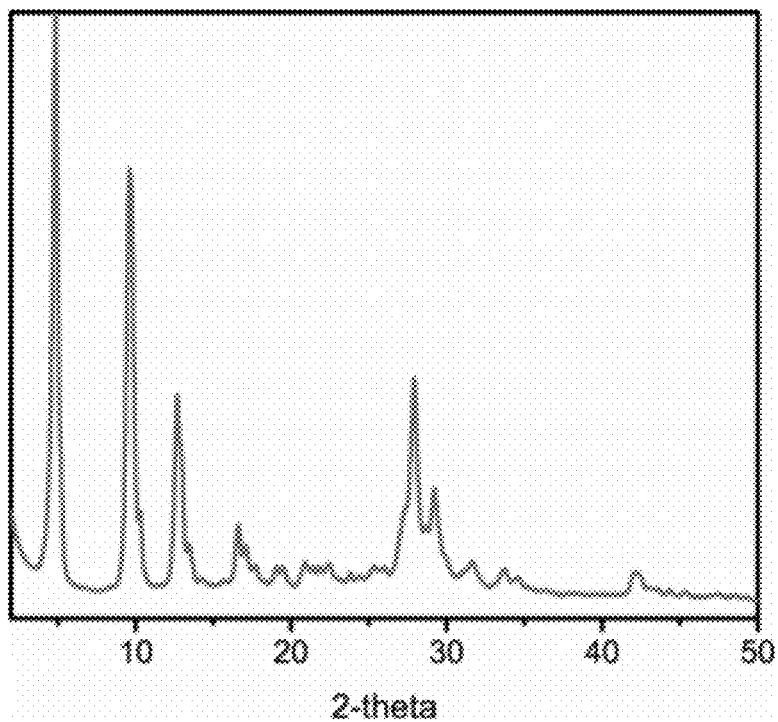
FIG. 5 presents a Powder X-Ray Diffraction Pattern of Cu-CAT-1 using a Bruker D8-Discover θ-20 θ diffractometer in reflectance Bragg-Brentano geometry.
Figure 6:
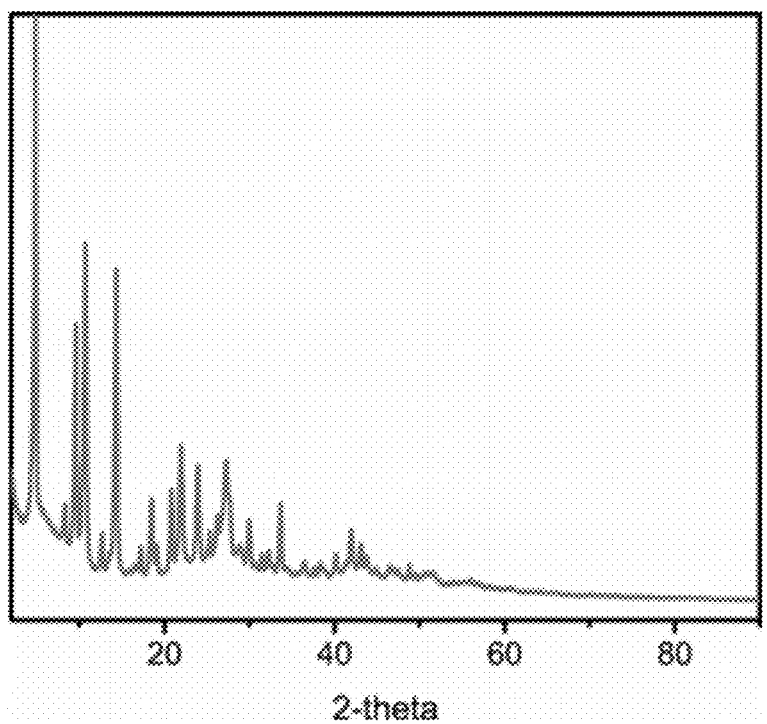
FIG. 6 presents a Powder X-Ray Diffraction Pattern of Zr-CAT-1 using a Bruker D8-Discover θ-20 θ diffractometer in reflectance Bragg-Brentano geometry.
Figure 7:
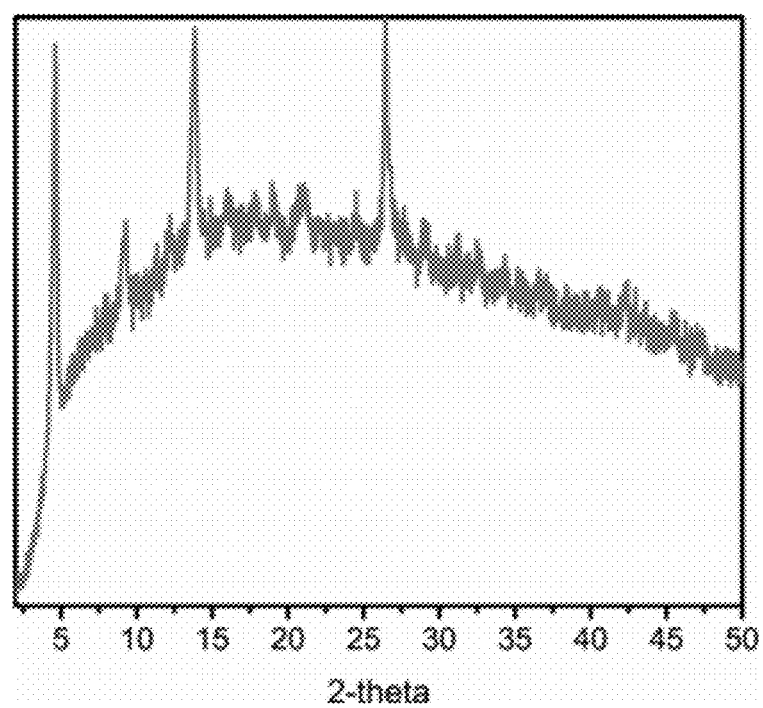
FIG. 7 presents a Powder X-Ray Diffraction Pattern of Co-CAT-1 using a Bruker D8-Discover θ-20 θ diffractometer in reflectance Bragg-Brentano geometry.
Figure 8:
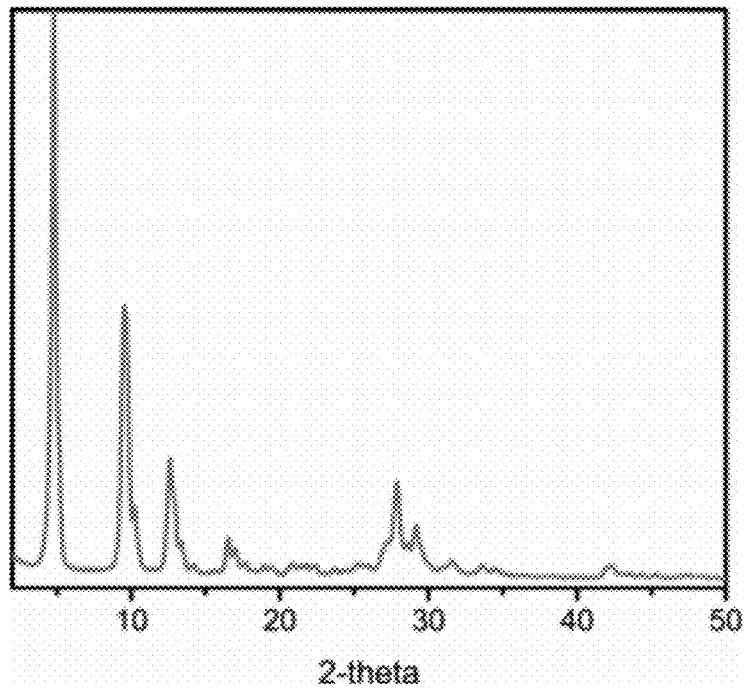
FIG. 8 presents a Powder X-Ray Diffraction Pattern of Mg-CAT-1 using a Bruker D8-Discover θ-20 θ diffractometer in reflectance Bragg-Brentano geometry.
Figure 9:
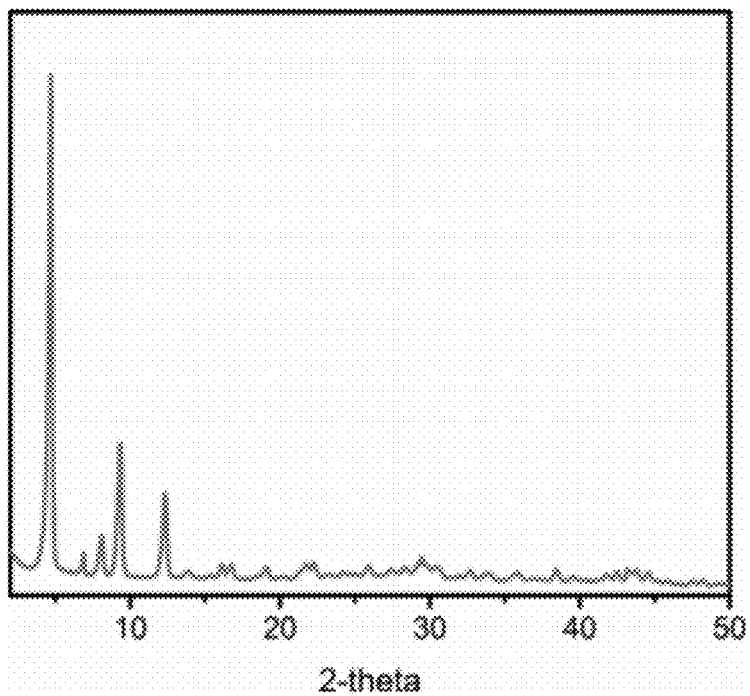
FIG. 9 presents a Powder X-Ray Diffraction Pattern of Ca-CAT-1 using a Bruker D8-Discover θ-20 θ diffractometer in reflectance Bragg-Brentano geometry.
Figure 10:
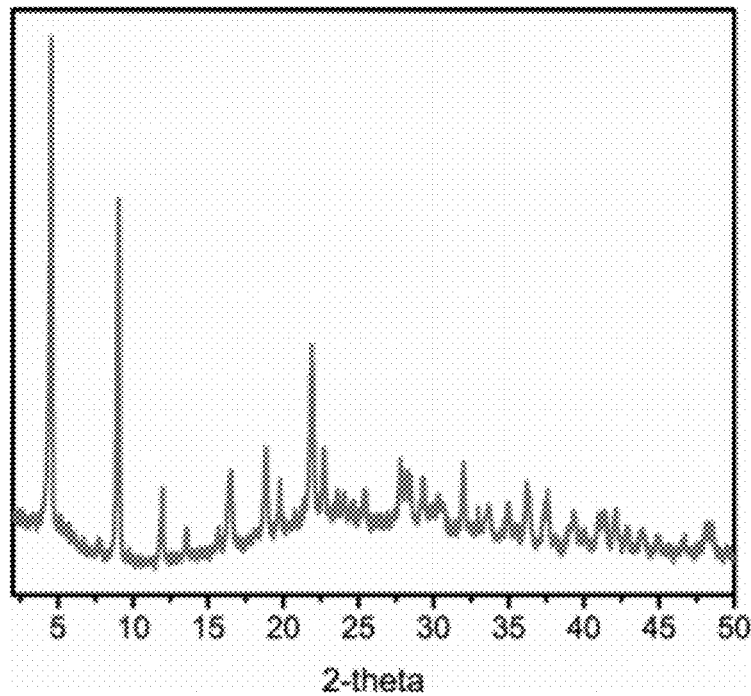
FIG. 10 presents a Powder X-Ray Diffraction Pattern of Ba-CaT-1 using a Bruker D8-Discover θ-20 θ diffractometer in reflectance Bragg-Brentano geometry.
Figure 11:
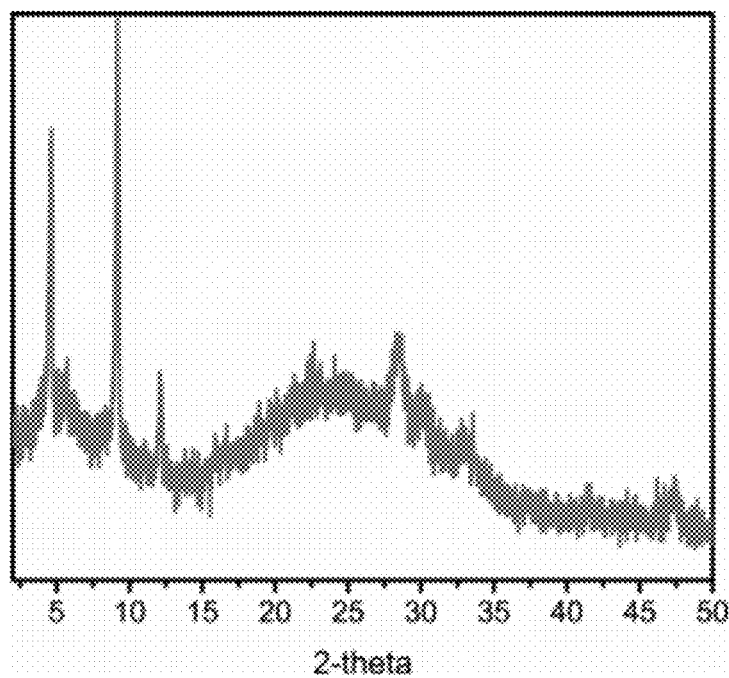
FIG. 11 presents a Powder X-Ray Diffraction Pattern of Ce-CAT-1 using a Bruker D8-Discover θ-20 θ diffractometer in reflectance Bragg-Brentano geometry.
Figure 12:
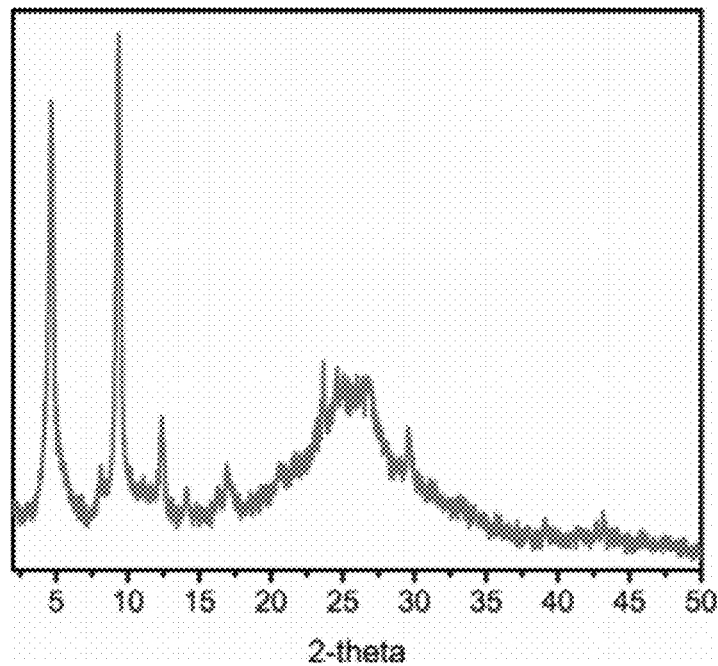
FIG. 12 presents a Powder X-Ray Diffraction Pattern of V-CAT-1 using a Bruker D8-Discover θ-20 θ diffractometer in reflectance Bragg-Brentano geometry.
Figure 13:
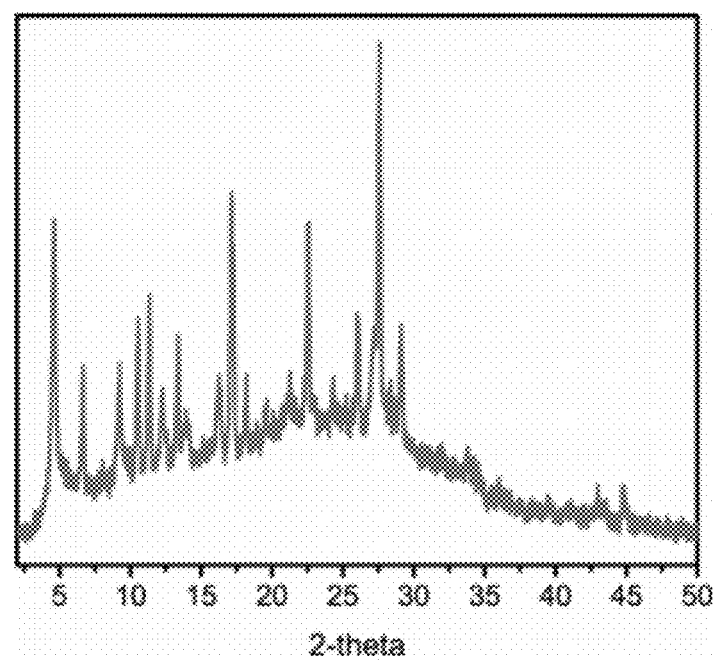
FIG. 13 presents a Powder X-Ray Diffraction Pattern of Mn-CAT-1 using a Bruker D8-Discover θ-20 θ diffractometer in reflectance Bragg-Brentano geometry.
Figure 14:
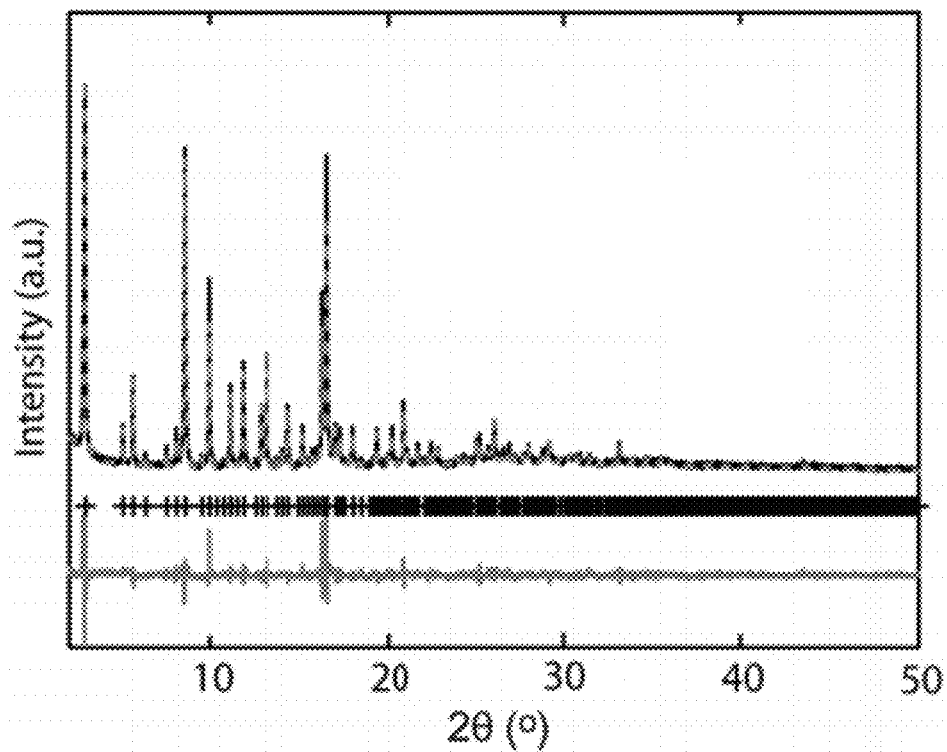
FIG. 14 presents a Powder X-Ray Diffraction Pattern of Ni-CAT-1 in black, the refined profile presented as the top line in light gray, and the difference plot presented as the bottom gray line (observed minus refined profiles).

| Compound | Metal | See Figure number |
|---|---|---|
| Ni-CAT-1 | nickel | FIGS. 3, and 14 |
| Zn-CAT-1 | zinc | FIG. 4 |
| Cu-CAT-1 | copper | FIG. 5 |
| Zr-CAT-1 | zirconium | FIG. 6 |
| Co-CAT-1 | cobalt | FIG. 7 |
| Mg-CAT-1 | magnesium | FIG. 8 |
| Ca-CAT-1 | calcium | FIG. 9 |
| Ba-CAT-1 | barium | FIG. 10 |
| Ce-CAT-1 | cerium | FIG. 11 |
| V-CAT-1 | vanadium | FIG. 12 |
| Mn-CAT-1 | manganese | FIG. 13 |

Figure 15:
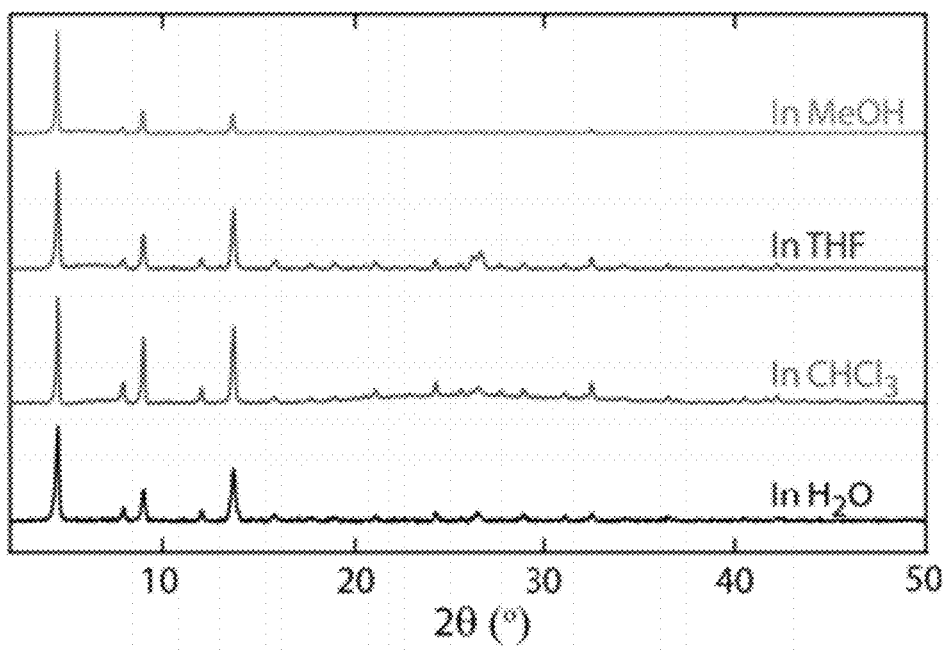
FIG. 15 presents Powder X-Ray Diffraction Patterns of Co-CAT-1 after immersing in different solvents for one week.
Figure 16:
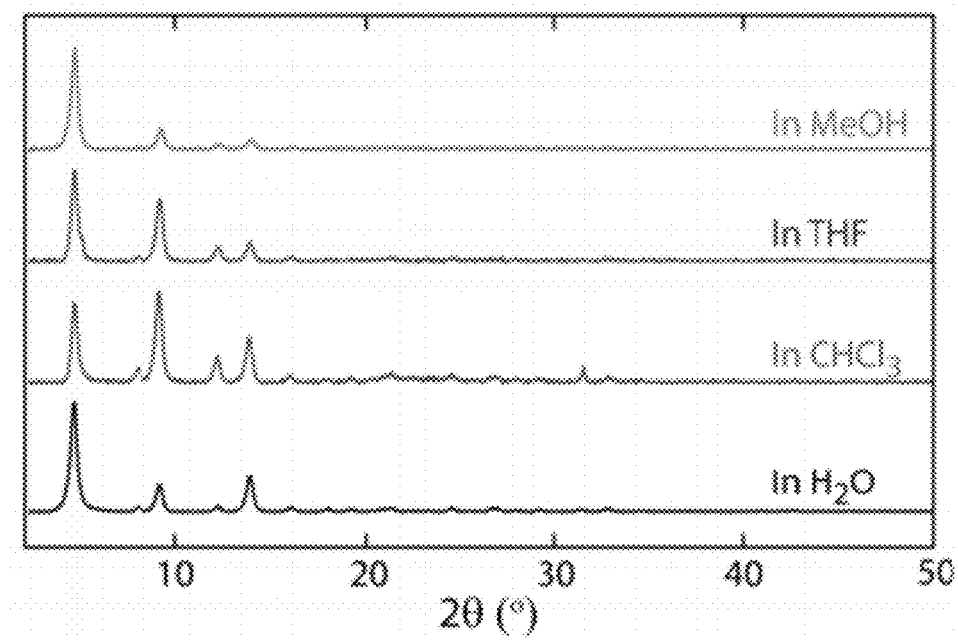
FIG. 16 presents Powder X-Ray Diffraction Patterns of Ni-CAT-1 after immersing in different solvents for one week.

The chemical stability of Ni- and Co-CATs was further examined by suspending samples of Co and Ni-CATs in water, methanol, tetrahydrofuran, and chloroform for 10 days. PXRD pattern collected for each sample showed that the solid samples of CATs series retain their crystallinity (see FIGS. 15-16).

Electron Paramagnetic Spectroscopy (EPR). EPR studies of CATs were conducted on an EMX electron paramagnetic resonance spectrometer under ambient temperature using a Bruker EMX/X band 9.776 GHz spectrometer, equipped with a standard mode cavity. All spectra were collected at room temperature with the following settings: sweep width=1600 G, center field=3200 G, modulation amplitude=4 G, microwave frequency=9.78 GHz, and microwave power=1 mW. Samples of CATs were transferred to an EPR tube.

Figure 17:
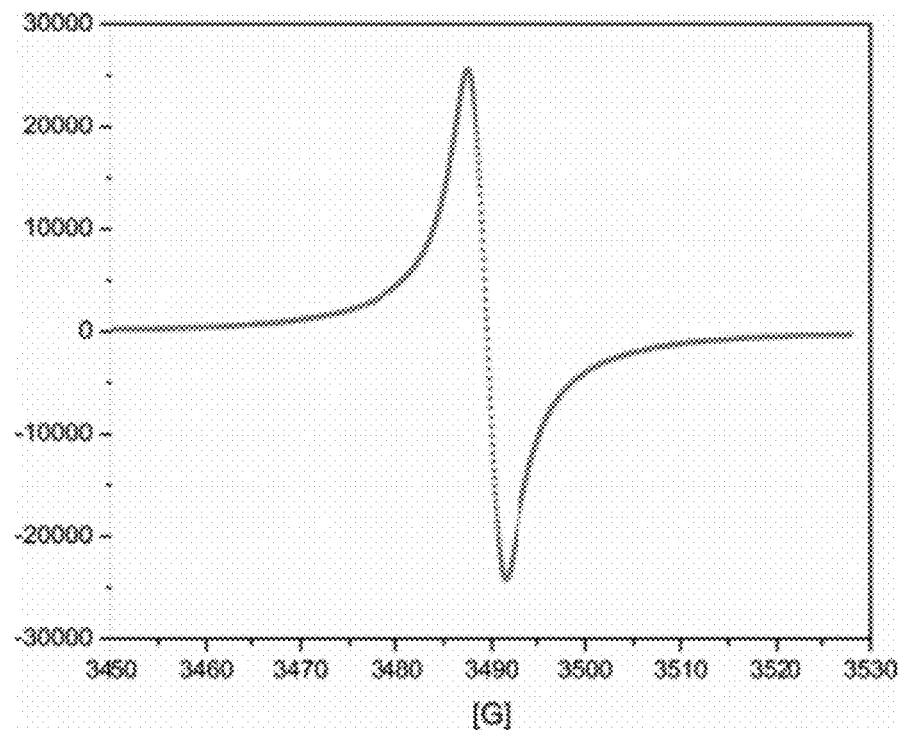
FIG. 17 presents an Electron Paramagnetic Spectroscopy plot of Zr-CAT-1 at ambient temperature.
Figure 18:
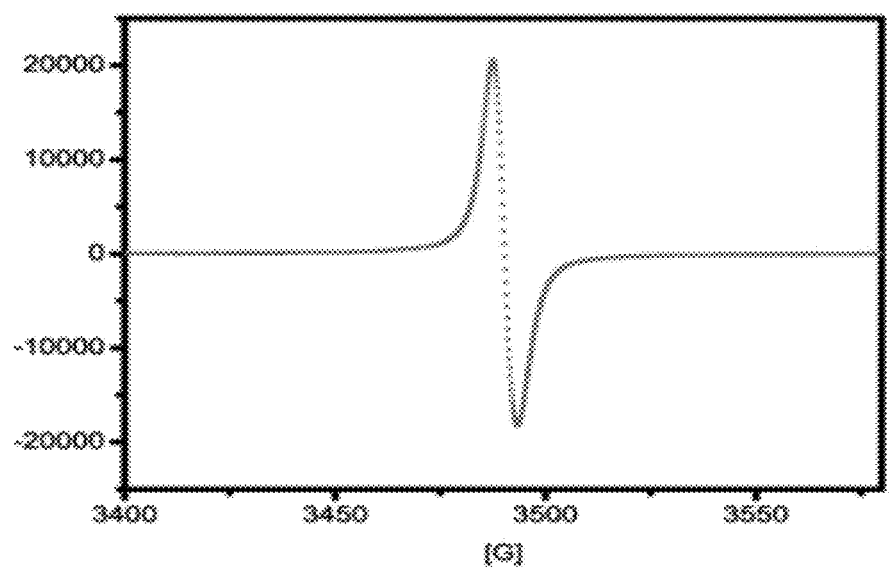
FIG. 18 presents an Electron Paramagnetic Spectroscopy plot of Zn-CAT-1 at ambient temperature.

Diamagnetic metal Zr(IV) and Zn(II) were tested under ambient temperature to avoid interference. The EPR plot of Zr-CAT-1 is presented in FIG. 17, while the EPR plot of Zn-CAT-1 is presented in FIG. 18.

Since the deprotonated HHTP has up to seven different oxidation states, room temperature EPR studies of HHTP and of the Co-CAT-1 were performed to investigate the oxidation state of HHTP. The semi-quinone form was confirmed by a near-symmetric signal at g=2.017, indicative of the presence of organic monoradical (see FIG. 19).

Single Crystal X-ray Diffraction Analyses. X-ray structural analysis of Co-CAT-1 revealed expanded porous layers, in which metals are octahedrally coordinated by two catecholates units and capped by two water molecules. Interestingly, discrete trinuclear complexes composed of one HHTP link coordinated to three metals ions were formed within the interlayer space.

The single crystal x-ray diffraction study of the Co-CAT-1 was carried out using synchrotron radiation in the beamline 24-ID-C at NECAT, in the Advanced Photon Source (APS) at Argonne National Laboratory. The crystal was solved in the trigonal space group, P-3c1.

There are two independent, crystallographic metal atoms, both in an octahedral coordination environment. One of these metal atoms is coordinated to two adjacent deprotonated HHTP ligands and two water molecules to complete the octahedral coordination sphere, resulting in the formation of an extended 2D framework. Conversely, the second metal atom is coordinated to only one HHTP ligand and to four water molecules giving rise to discrete complexes composed of $Co_3HHTP(H_2O)_{12}$. As a result, the structure of CATs is comprised of two distinct types of alternatively stacked layers. The first layer is an extended honeycomb structure with hexagonal pores (FIG. 1B), and the second layer is formed by the discrete units (FIG. 1C) described above. The two axial water molecules participating in the formation of these discrete complexes are hydrogen bonded to oxygen atoms of the HHTP in the adjacent layers. These hydrogen bonds, accompanied by π-π interactions, create a distortion of the overall structure, leading to corrugated hexagonal layers (FIG. 1D). Hexagonal pores are thus created running along the c axis. These pores are lined with the coordinated water molecules of the complexes, producing a highly hydrophilic pore environment (FIG. 1A).

Figure 19:
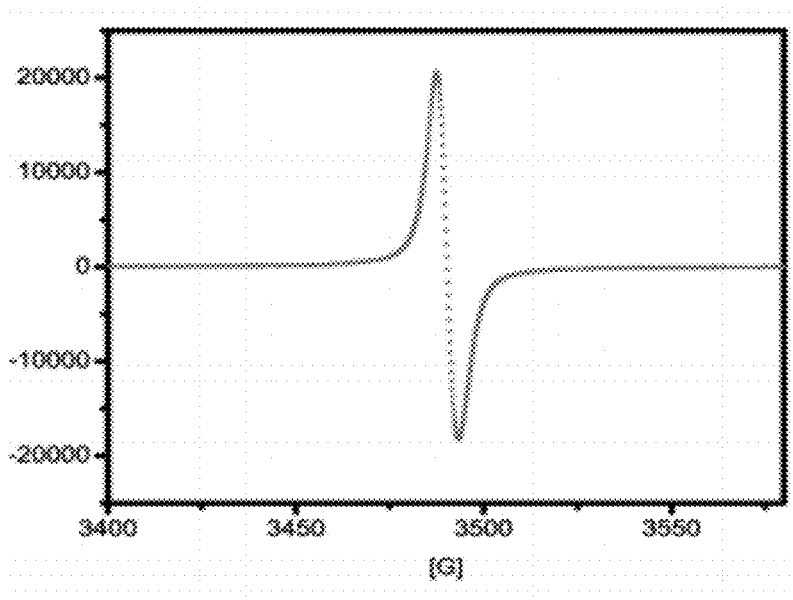
FIG. 19 presents an Electron Paramagnetic Spectroscopy plot of Co-CAT-1 at ambient temperature.

When considering charge balance, the deprotonated HHTP must be in the −3 oxidation state when present in the covalently extended first type of layer, indicating a presence of the semiquinonate version of the link. This oxidation state was confirmed by electron paramagnetic resonance (EPR)

analyses performed on CATs (FIG. 19). For the discrete complexes, $Co_3HHTP(H_2O)_{12}$, a −6 oxidation state is required for HTTP in order to compensate the respective charges.

Figure 22:
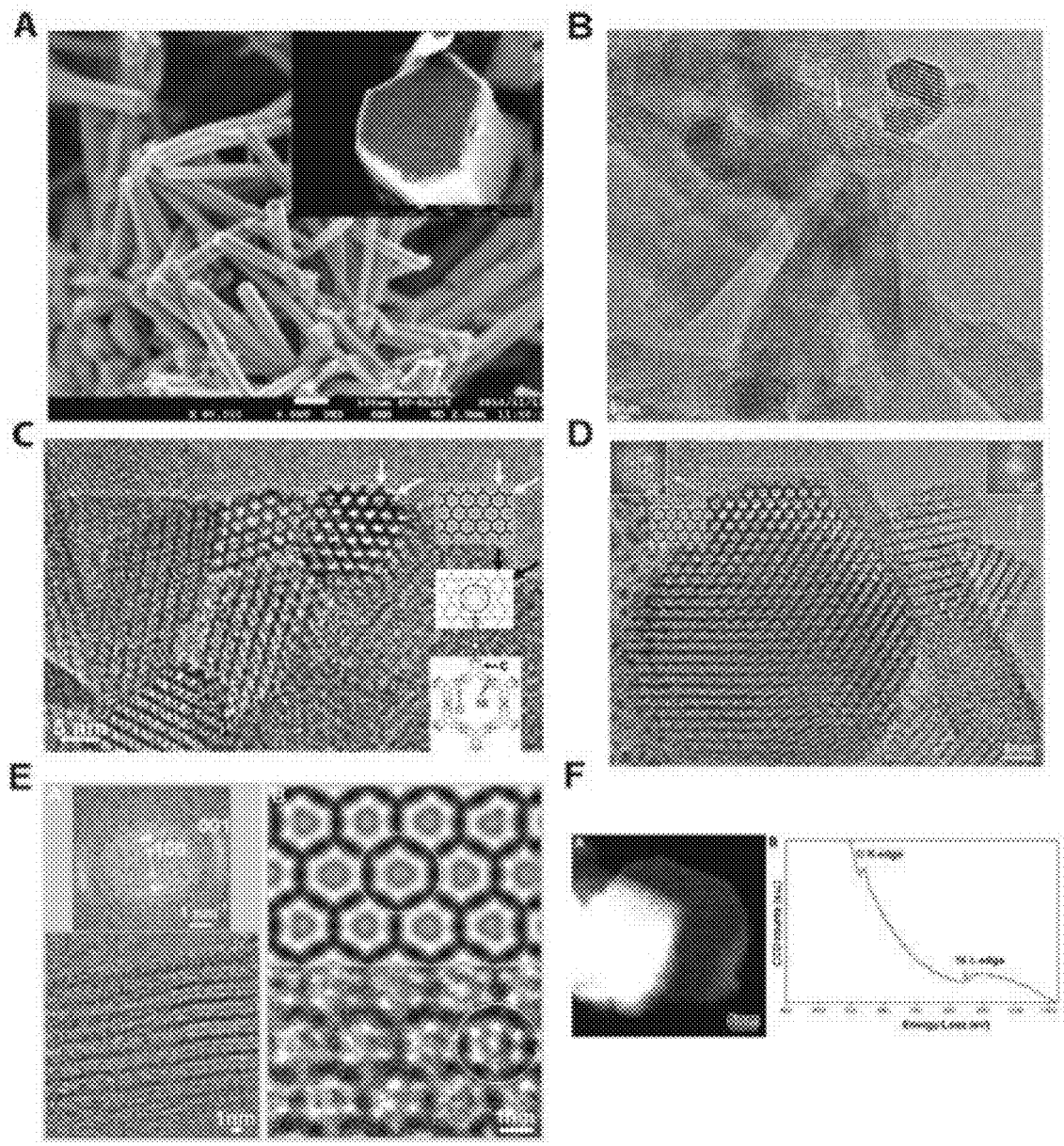
FIG. 22A-F provides (A) an FE SEM image of Ni-CAT-1 showing uniform rod; inset: zoom in showing hexagonal shape surface; (B) low magnification HR-TEM image of the activated Ni-CAT-1 taken at 120 kV; (C) High magnification HR-TEM image showing the terminal structure of activated Ni-CAT-1 as indicated by arrows; (D) High magnification HR-TEM image of Ni-CAT-1 taken at 120 kV, the inserted images are the fast Fourier transform (FFT) analysis of the corresponding areas indicated by arrows; (E) FFT image demonstrating the wavy characterization of the edges perpendicular to the pore walls and comparison between the HR-TEM and stimulated images looking through the [001] direction; and (F) annular dark-field scanning transmission electron microscopy (ADF-STEM) image taken under 60 kV and electron energy loss spectroscopy (EELS) spectrum.

Synthesized crystals of Ni-CAT-1 were not of suitable size for single crystal x-ray analysis. Nevertheless, a Rietveld refinement of Ni-CAT-1 was performed against the powder diffraction pattern collected with synchrotron radiation, employing the atomic coordinates obtained from the single crystal data of Co-CAT (FIG. 22). The refinement converged with excellent residual values, demonstrating that Co and Ni-CAT possess the same structure (FIG. 14). Table 2 presents the crystal data and structure refinement for Co-CAT-1 obtained from the Single Crystal X-ray Diffraction Analyses.

TABLE 2

| | |
|---|---|
| Identification code | Co-CAT-1 |
| Empirical formula | $C_{144}H_{48}Co_{18}O_{160}$ |
| Formula weight | 5398.56 |
| Temperature | 293(2) K |
| Wavelength | 0.92017 Å |
| Crystal system | Trigonal |
| Space group | P-3c1 |
| Unit cell dimensions | a = 22.130(3) Å, α = 90° |
| | b = 22.130(3) Å, β = 90° |
| | c = 13.310(3) Å, γ = 120° |
| Volume | 5645.1(16) Å$^3$ |
| Z | 1 |
| Density (calculated) | 1.588 Mg/m$^3$ |
| Absorption coefficient | 1.401 mm$^{-1}$ |
| F(000) | 2678 |
| Theta range for data collection | 1.84 to 20.08° |
| Index ranges | −20 <= h <= 20, −21 <= k <= 21, |
| | −11 <= l <= 12 |
| Reflections collected | 17423 |
| Independent reflections | 1717 [R(int) = 0.0387] |
| Completeness to theta | = 20.08° 96.1% |
| Absorption correction | None |
| Refinement method | Full-matrix least-squares on F$^2$ |
| Data/restraints/parameters | 1717/0/240 |
| Goodness-of-fit on F$^2$ | 1.118 |
| Final R indices [I > 2sigma(I)] | R1 = 0.0734, wR2 = 0.2048 |
| R indices (all data) | R1 = 0.0844, wR2 = 0.2136 |
| Largest diff. peak and hole | 0.556 and −0.672 e · Å$^{-3}$ |

Figure 20:
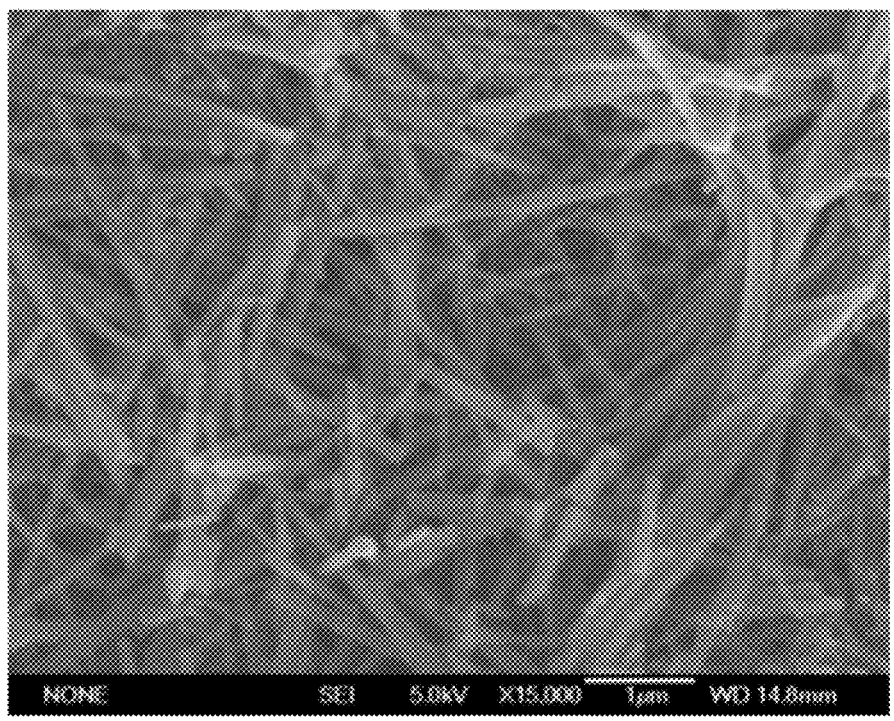
FIG. 20 provides a Scanning Electron Microscope image of Ni-CAT-1.
Figure 21:
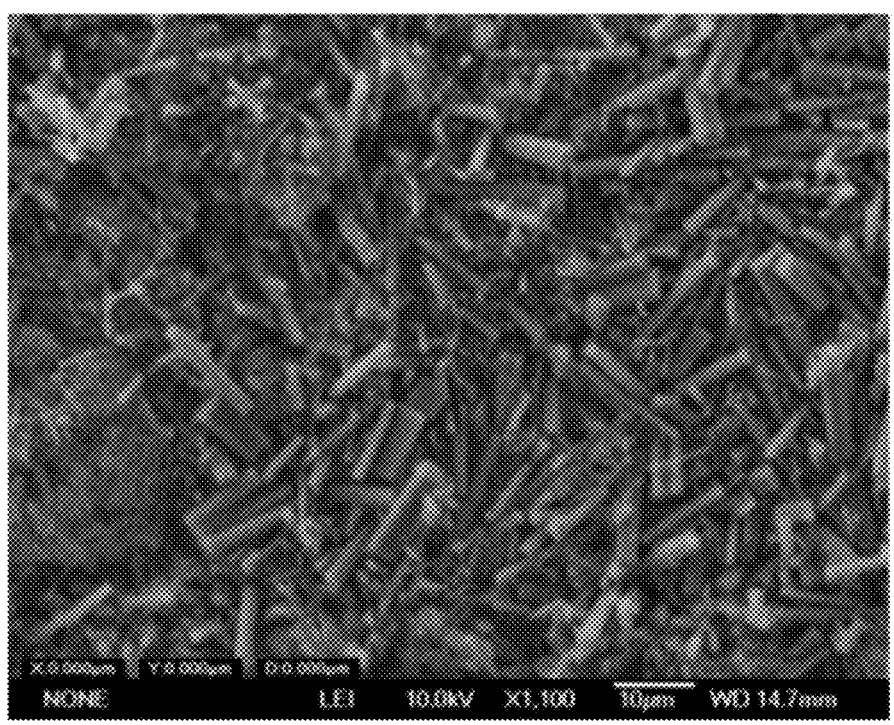
FIG. 21 provides a Scanning Electron Microscope image of Zn-CAT-1.

Scanning Electron Microscopy (SEM) images. Samples of CATs were prepared by dispersing the material onto a sticky carbon surface attached to a flat aluminum sample holder. Images of the samples were taken directly without any coating. Samples were analyzed on a JOEL JSM-6700 Scanning Electron Microscope using both the SEI and LEI detectors with accelerating voltages ranging from 1 kV to 15 kV. The SEM image of Ni-CAT-1 is provided in FIG. 20, while the SEM image of Zn-CAT-1 is provided in FIG. 21.

High-resolution transmission electron microscopy observation: A JEM-2010F field emission TEM equipped with a CEOS post-specimen spherical aberration corrector ($C_s$ corrector) was operated at 120 kV for HRTEM imaging. Also, a JEM-2100F with a cold field-emission gun equipped with a DELTA $C_s$ corrector was operated at 60 kV and 30 kV in order to compare beam damage effects. A Gatan GIF Quantum equipped on the above JEM-2100F was used for performing electron energy loss spectroscopy (EELS) analysis in STEM mode at 60 kV. Since MOF materials are electron beam sensitive, the electron beam damage to the specimen was minimized as much as possible (in this study, the beam density during the observations was from 50 to 150 electrons/(nm$^2$·s)). A single HRTEM image with an exposure time of 2 seconds or a sequence of images (10 frames) was recorded, with a 0.5 second exposure time for each and after drift compensation, some frames can be superimposed to increase the signal-to-noise (SN) ratio for display. It was found that ordered structure was destroyed more rapidly under 30 KV than 60 kV or 120 KV. This is due to the radiation damage caused by radiolysis; therefore, an operating voltage of 120 kV is more suitable as the observation condition in this case (FIGS. 23 and 24A-B).

The crystal structure of Ni-CAT-1 was clarified through the use of high-resolution transmission electron microscopy (HR-TEM). A high-resolution field emission scanning electron microscope (FE-SEM) image of the activated Ni-CAT-1 sample was collected. The image revealed that Ni-CAT-1 had singular morphology of hexagonal rods whose lengths were on the micrometer scale, whereas the widths were only ~100 nm (FIG. 22A). The low magnification HR-TEM image of the activated Ni-CAT was processed at 120 kV (FIG. 22B). In this image, both the channel direction (incident electron beam perpendicular to the channels) and the channel arrangement of a uniform honeycomb structure (incident electron beam parallel to the channels) were observed with some defects identified as indicated by the arrow.

Although HR-TEM has been used as a powerful method to determine surface structures in porous zeolites, this is the first instance of using HR-TEM to observe the terminal structure of a crystalline MOF. The surprisingly clear image of the terminal structure of activated Ni-CAT-1 can be clearly observed (FIG. 22C). The HR-TEM image is also in good agreement with the simulated image of the proposed structure of Ni-CAT-1 (FIG. 22C). However, it is not clear with respect to elucidating the actual termination of the metal organic molecules, as the images were taken in an under-focus manner so as to have better contrast. The HR-TEM images were processed using fast Fourier transform (FFT) analysis. This processing allowed for the determination of the unit cell lattice parameter of a=2.02 nm (FIG. 22D). This finding is in good agreement with the value obtained from the single crystal data analysis using Co-CAT-1. The arc line labeled by the (001) reflection shown in the FFT image, in the inset of FIG. 22E, shows that the fringes perpendicular to the pore walls have a wave-like characteristic. This wave-like characteristic indicates that the Ni atoms are fluctuating in and out on the fringes. The spacing between these wavy fringes, calculated from the FFT images, is about 0.32 nm, which corresponds well with the distance between layers. The comparison between the HR-TEM images and the simulated images looking through the (001) direction is presented in FIG. 22E. The characteristic six black dots and the small circle inside, which are labeled by the white circles in both HR-TEM and simulated images, are in agreement with each other, which further validate the proposed structure (FIG. 22E).

It is often a challenge to observe MOFs by using scanning transmission electron microscopy (STEM) due to a having to use a focused beam that has a higher beam density than what is typically used in the transmission electron microscopy (TEM) mode. Generally, zeolite and mesoporous silica are damaged at a much faster rate when using the STEM mode instead of the TEM mode. Remarkably, using the STEM mode, the first instance of imaging a crystalline MOF material has been generated. The honeycomb structure of Ni- CAT-1 is clearly observed in the STEM image, albeit at the expense of structural stability, which collapsed after the whole scan was finished. The analytical result of the electron energy loss spectroscopy (EELS) showed that the Ni (L-edge) and O (K-edge) can be identified (FIG. 22F). Table 3 presents the d spacing as measured from the HRTEM images, along with calculations made from a hexagonal based structure. The numbers are in good agreement with each other.

TABLE 3

| observed | calculated | index |
|---|---|---|
| 1.75 | 1.75 | 100 |
| 1.01 | 1.01 | 110 |
| 0.88 | 0.88 | 200 |
| 0.67 | 0.66 | 210 |
| 0.59 | 0.58 | 300 |
| 0.50 | 0.51 | 220 |
| 0.32 | 0.32 | 001 |

$N_2$ or Argon Isotherm Curves. $N_2$ or Argon isotherm curves of CAT complexes were obtained using a Quantachrome Nova or Autosorb. The surface area of the compounds was calculated according to the Brunauer-Emmet-Teller (BET) method.

Figure 25:
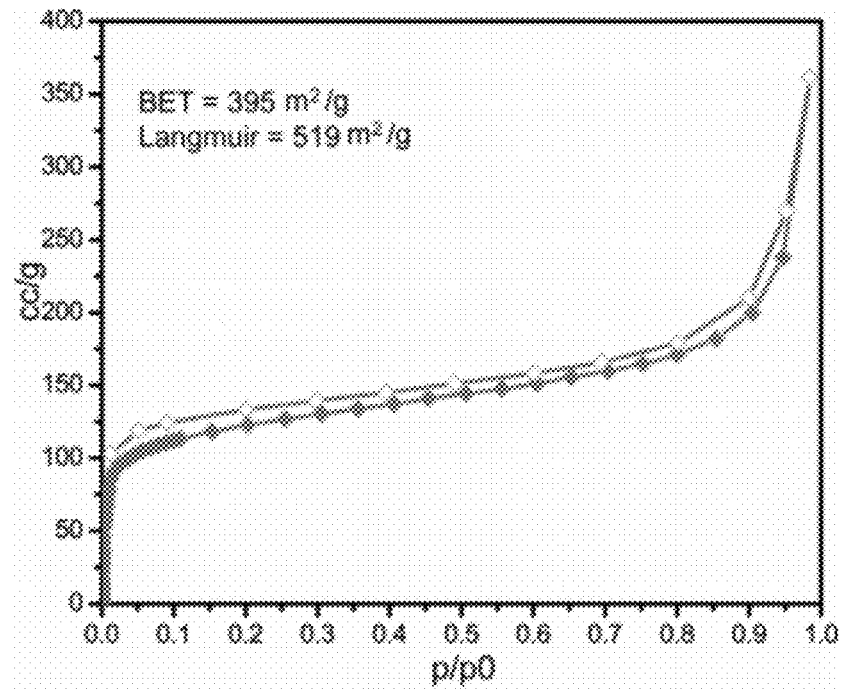
FIG. 25 presents an argon adsorption isotherm for Ni-CAT-1 measured at 87 K. Adsorption and desorption points are represented by filled and empty circles, respectively.
Figure 26:
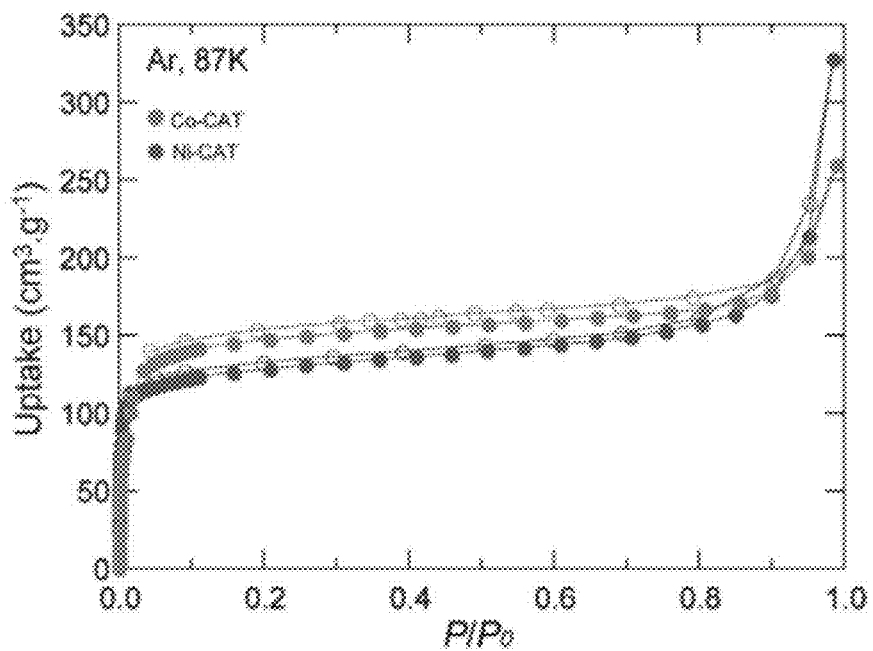
FIG. 26 presents an argon adsorption isotherm for Ni and Co-CAT-1 measured at 87 K. Adsorption and desorption points are represented by filled and empty circles, respectively.
Figure 27:
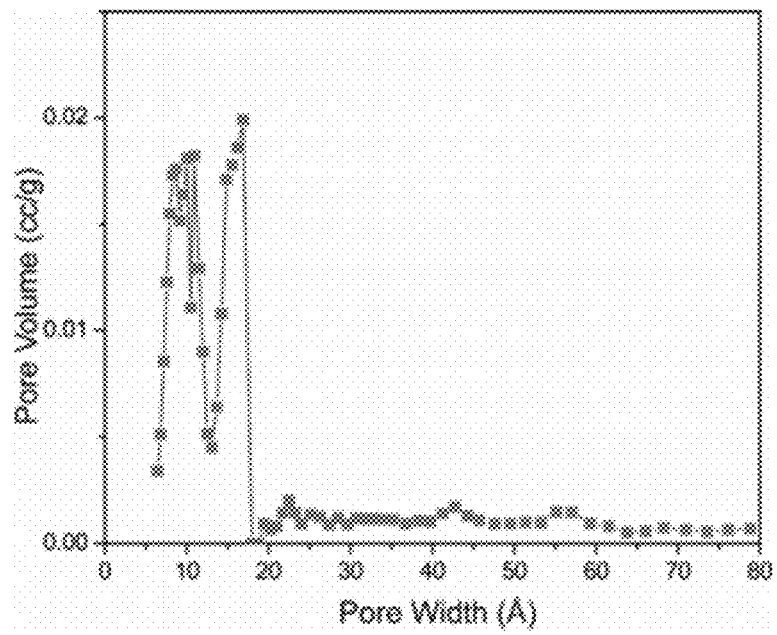
FIG. 27 presents a graph of pore size distribution of Ni-CAT-1 using a cylindrical pore model.
Figure 28:
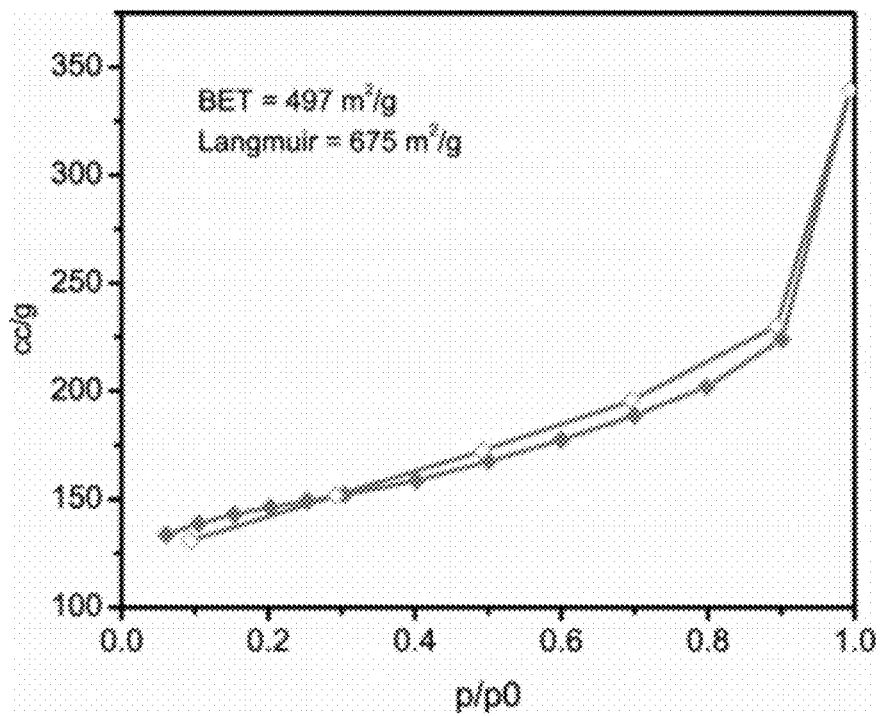
FIG. 28 presents a $N_2$ isotherm curve of Zn-CAT-1. Adsorption and desorption points are represented by filled and empty circles, respectively.

In order to assess the porosity and the architectural stability of the CATs, Ar gas adsorption measurements at 87 K were performed. Initially, we carried out the activation procedures, in which as-synthesized CATs were subjected to solvent exchange followed by pore evacuation under dynamic vacuum at 85° C., to ensure that the pores are free of any guest molecules. The Ar isotherms for Ni-CAT-1 and Co-CAT-1 display significant uptake in the low-pressure region ($P/P_0$<0.1), an observation which is indicative of the microporous character (FIGS. 25-26). The BET (Brunauer-Emmett-Teller) surface areas for Ni and Co-CAT-1 were calculated to be 500 and 540 $m^2 \cdot g^{-1}$, respectively. Estimated micropore volumes based on a Dubinin-Raduskavich-plot method for Co and Ni-CAT are 0.18 and 0.20 $cm^3 \cdot g^{-1}$, respectively. The resulting Ni-CAT-1 pore size distribution determined by a cylindrical pore model is presented in FIG. 27. The porous structures of the CATs were further corroborated by fitting non-local density functional theory models to the isotherm data in order to provide pore size distributions that are centered at 12 Å, a value, identical to the pore diameters obtained from the crystal structures (12 Å). The 77 K $N_2$ isotherm curve of Zn-CAT-1 is presented in FIG. 28, while the 77 K $N_2$ isotherm curve of Zr-CAT-1 is presented in FIG. 29.

Conductivity Measurements. To determine the conductivity of the CATs, a CAT crystal was positioned so that only the ends of crystal were touching two electrodes, a current was then provided, and the resistance was measured. Conductivity of Cu-CAT-1 was found to be comparable to that of organic conductors. An image of a Cu-CAT-1 crystal touching and located between the two electrodes is presented in FIG. 30A. The resulting plot of Cu-CAT-1 conductivity is presented in FIG. 30B.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A metal catecholate (CAT) framework, comprising one or more cores comprising Formula IV(a):

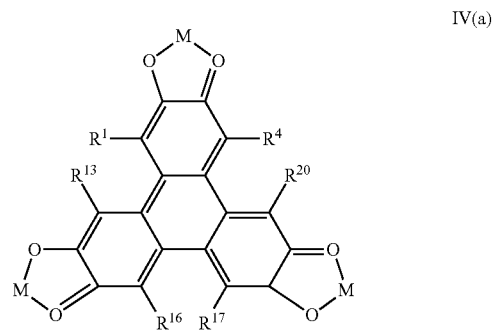

IV(a)

wherein,

M is each individually a metal, metal ion, or metal containing complex;

$R^1$, $R^4$, $R^{13}$, $R^{16}$-$R^{17}$, and $R^{20}$ are each individually selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$) alkynyl, and optionally substituted ($C_1$-$C_5$)heteroalkynyl.

2. The CAT framework of claim 1, comprising one or more core units comprising Formula IV(b):

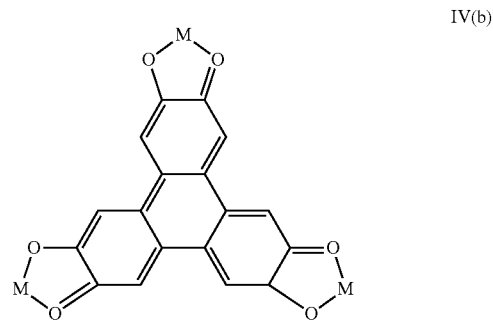

IV(b)

wherein, M is each individually a metal, metal ion, or metal containing complex.

3. The CAT framework of claim 1, comprising one or more core units comprising Formula V:

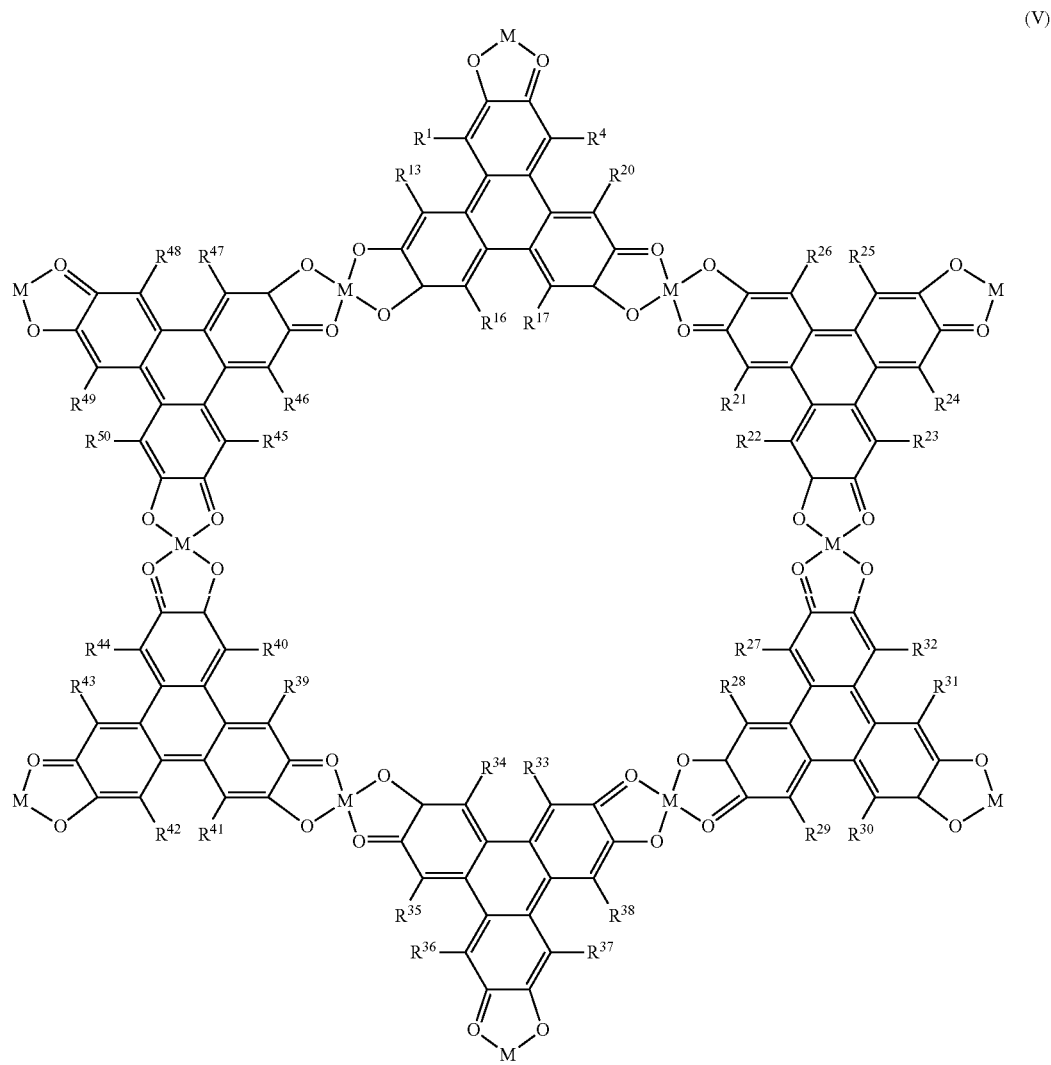

(V)

wherein,
M is each individually a metal, metal ion, or metal containing complex;

$R^1$, $R^4$, $R^{13}$, $R^{16}$-$R^{17}$ and $R^{20}$-$R^{50}$ are independently selected from the group comprising H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$) alkynyl, optionally substituted ($C_1$-$C_5$)heteroalkynyl, optionally substituted ($C_1$-$C_6$)cycloalkyl, optionally substituted ($C_1$-$C_6$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, catechol and mixed ring system;

wherein at least one of $R^1$, $R^4$, $R^{13}$, $R^{16}$-$R^{17}$, and $R^{20}$-$R^{50}$ comprises a covalently bound hydroxyl, catechol, triazole, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, POSH, $AsO_3H$, $AsO_4H$, $P(SH)_3$, $As(SH)_3$, $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(X^1SH)_2$, $C(X^1SH)_3$, $CH(X^1NH_2)_2$, $C(X^1NH_2)_3$, $CH_2(X^1OH)_2$, $C(X^1OH)_3$, $CH_2(X^1(OH)_2)_2$, $C(X^1(OH)_2)_3$, $CH(X^1CN)_2$, and $C(X^1CN)_3$; and $X^1$ is an alkyl group having from 1 to 2 carbon atoms.

4. The CAT framework of claim 3, comprising one or more core units comprising Formula V(a):

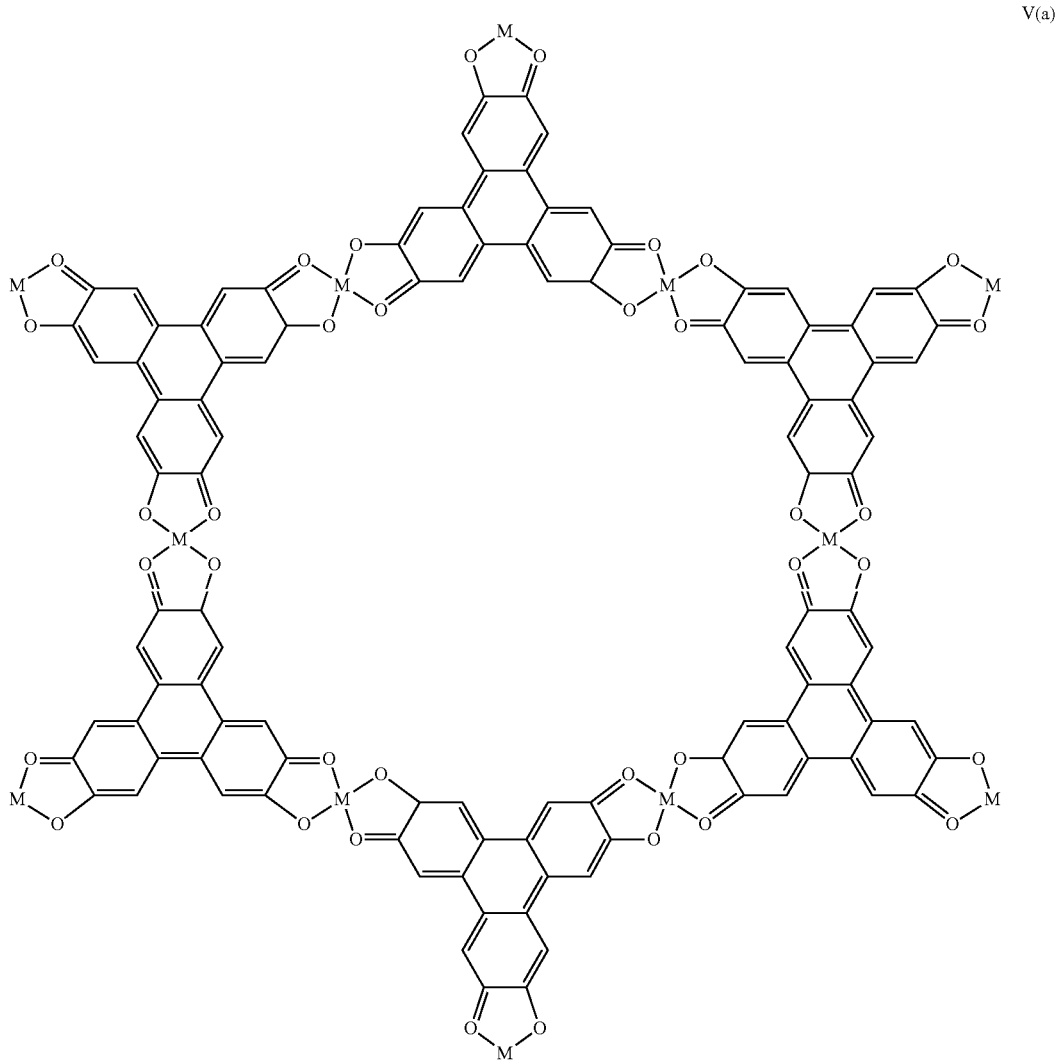

V(a)

wherein, M is each individually a metal, metal ion, or metal containing complex.

5. The CAT framework of claim 1, wherein the metal or metal ion is each individually selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pr$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, and $Lu^{3+}$.

6. The CAT framework of claim 5, wherein the metal ion is $Ni^{2+}$, $Cu^{2+}$, or $Co^{2+}$.

7. The CAT framework of claim 1, wherein the pores of the framework is activated by being substantially free of any guest molecules.

8. The CAT framework of claim 1, wherein the CAT framework is reacted with one or more post framework reactants.

9. The CAT framework of claim 1, further comprising one or more absorbed or adsorbed chemical species.

10. The CAT framework of claim 9, wherein the adsorbed or absorbed chemical species is selected from the group consisting of gases, optionally substituted ($C_1$-$C_{25}$) organic molecules, inorganic molecules, and combinations thereof.

11. The CAT framework of claim 10, wherein the adsorbed or absorbed chemical species is selected from the group consisting of argon, ammonia, carbon dioxide, carbon monoxide, hydrogen, amines, oxygen, ozone, nitrogen, nitrous oxide, organic dyes, polycyclic organic molecules, hydrogen sulfide, carbonyl sulfide, carbon disulfide, mercaptans, hydrocarbons, formaldehyde, diisocyanates, trichloroethylene, fluorocarbons, and combinations thereof.

* * * * *

UNITED STATES PATENT AND TRADEMARK OFFICE
CERTIFICATE OF CORRECTION

PATENT NO.       : 8,742,152 B2                                                Page 1 of 1
APPLICATION NO.  : 13/363792
DATED            : June 3, 2014
INVENTOR(S)      : Omar M. Yaghi et al.

It is certified that error appears in the above-identified patent and that said Letters Patent is hereby corrected as shown below:

IN THE SPECIFICATION

In Column 1, please replace lines 8-11 with the following:

--This invention was made with Government support under DE-FG36-08GO18141 and DE-SC0001342 awarded by the Department of Energy. The Government has certain rights in the invention.--

Signed and Sealed this
Second Day of August, 2016

Michelle K. Lee
*Director of the United States Patent and Trademark Office*